US009845290B2

(12) United States Patent
Balasubramanian et al.

(10) Patent No.: US 9,845,290 B2
(45) Date of Patent: Dec. 19, 2017

(54) METHODS FOR FORMING PEROXYFORMIC ACID AND USES THEREOF

(71) Applicant: Ecolab USA Inc., St. Paul, MN (US)

(72) Inventors: Ramakrishnan Balasubramanian, Sugarland, TX (US); Junzhong Li, Eagan, MN (US); Richard Staub, Lakeville, MN (US); Victor Keasler, Sugarland, TX (US); Brian Bennett, Sugarland, TX (US); Allison Brewster, Eagan, MN (US)

(73) Assignee: Ecolab USA Inc., Saint Paul, MN (US)

( * ) Notice: Subject to any disclaimer, the term of this patent is extended or adjusted under 35 U.S.C. 154(b) by 0 days.

(21) Appl. No.: 14/972,308

(22) Filed: Dec. 17, 2015

(65) Prior Publication Data

US 2016/0176814 A1 Jun. 23, 2016

Related U.S. Application Data

(60) Provisional application No. 62/094,056, filed on Dec. 18, 2014.

(51) Int. Cl.
| | | |
|---|---|---|
| *C07C 409/24* | (2006.01) | |
| *A01N 37/16* | (2006.01) | |
| *A23L 3/3463* | (2006.01) | |
| *C07C 407/00* | (2006.01) | |
| *A23L 3/3508* | (2006.01) | |

(52) U.S. Cl.
CPC ............ *C07C 409/24* (2013.01); *A01N 37/16* (2013.01); *A23L 3/34635* (2013.01); *A23L 3/3508* (2013.01); *C07C 407/00* (2013.01); *C07C 407/006* (2013.01); *A23V 2002/00* (2013.01)

(58) Field of Classification Search
CPC . C07C 407/00; C07C 407/006; C07C 409/24; A01N 37/16; A23L 3/34635; A23L 3/3508; A23V 2002/00
See application file for complete search history.

(56) References Cited

U.S. PATENT DOCUMENTS

| | | | |
|---|---|---|---|
| 2,955,905 A | 10/1960 | Davies et al. | |
| 2,995,524 A | 8/1961 | Wylie et al. | |
| 3,169,986 A * | 2/1965 | Webb .................. | C07C 407/003 562/4 |
| 3,256,198 A | 6/1966 | Matzner | |
| 3,272,750 A | 9/1966 | Chase | |
| 3,432,546 A | 3/1969 | Oringer et al. | |
| 3,470,959 A | 10/1969 | Kreuz et al. | |
| 3,480,557 A * | 11/1969 | Shiraeff ............... | C01B 15/037 252/186.29 |
| 3,847,830 A | 11/1974 | Williams et al. | |
| 3,925,234 A | 12/1975 | Hachmann et al. | |
| 4,003,841 A | 1/1977 | Hachmann et al. | |
| 4,051,058 A | 9/1977 | Bowing et al. | |
| 4,126,573 A | 11/1978 | Johnston | |
| 4,170,453 A | 10/1979 | Kitko | |
| 4,233,235 A | 11/1980 | Camden et al. | |
| 4,370,251 A | 1/1983 | Liao et al. | |
| 4,412,934 A | 11/1983 | Chung et al. | |
| 4,483,778 A | 11/1984 | Thompson et al. | |
| 4,486,327 A | 12/1984 | Murphy et al. | |
| 4,617,090 A | 10/1986 | Chum et al. | |
| 4,655,781 A | 4/1987 | Hsieh et al. | |
| 4,778,618 A | 10/1988 | Fong et al. | |
| 4,964,870 A | 10/1990 | Fong et al. | |
| 5,030,240 A | 7/1991 | Wiersema et al. | |
| 5,143,641 A | 9/1992 | Nunn | |

(Continued)

FOREIGN PATENT DOCUMENTS

| | | |
|---|---|---|
| CA | 2475361 A1 | 8/2003 |
| EP | 0231632 * | 8/1987 |
| EP | 0231632 A2 | 8/1987 |
| EP | 0233731 A2 | 8/1987 |
| EP | 0267047 A2 | 5/1988 |
| EP | 0751933 B1 | 8/1997 |
| EP | 0863098 B1 | 2/1998 |
| EP | 1022946 B1 | 9/1998 |
| EP | 1131016 B1 | 11/1999 |
| EP | 1125497 A2 | 2/2001 |

(Continued)

OTHER PUBLICATIONS

International Searching Authority, "International Search Report," issued in connection with International Patent Application No. PCT/US2015/066438, dated Apr. 6, 2016, 5 pages.
International Searching Authority, "Written Opinion," issued in connection with International Patent Application No. PCT/US2015/066438, dated Apr. 6, 2016, 9 pages.

(Continued)

*Primary Examiner* — Paul A Zucker
*Assistant Examiner* — Mark Luderer
(74) *Attorney, Agent, or Firm* — McKee, Voorhees & Sease, PLC

(57) ABSTRACT

The present invention relates generally to methods for forming peroxyformic acid, comprising contacting formic acid with hydrogen peroxide. The methods for forming peroxyformic acid can include adding formic acid with a relatively lower concentration of hydrogen peroxide, or adding formic acid to a peroxycarboxylic acid composition or forming composition to react with hydrogen peroxide in the compositions. The present invention also relates to peroxyformic acid formed by the above methods. The present invention further relates to the uses of peroxyformic acid for treating a variety of targets, e.g., target water, including target water used in connection with oil- and gas-field operations. The present invention further relates to methods for reducing or removing $H_2S$ or iron sulfide in the treated water source, improving clarity of the treated water source, or reducing the total dissolved oxygen or corrosion in the treated water source, using peroxyformic acid, including peroxyformic acid generated in situ.

35 Claims, 17 Drawing Sheets

(56) References Cited

U.S. PATENT DOCUMENTS

| | | |
|---|---|---|
| 5,200,189 A | 4/1993 | Oakes et al. |
| 5,314,687 A | 5/1994 | Oakes et al. |
| 5,431,849 A | 7/1995 | Damhus et al. |
| 5,503,765 A | 4/1996 | Schepers et al. |
| 5,505,740 A | 4/1996 | Kong et al. |
| 5,616,335 A | 4/1997 | Nicolle et al. |
| 5,635,195 A | 6/1997 | Hall, II et al. |
| 5,637,755 A | 6/1997 | Nagumo et al. |
| 5,681,805 A | 10/1997 | Scheuing et al. |
| 5,716,923 A | 2/1998 | MacBeath |
| 5,718,910 A | 2/1998 | Oakes et al. |
| 5,827,447 A | 10/1998 | Tamura et al. |
| 5,827,808 A | 10/1998 | Appleby et al. |
| 5,840,343 A | 11/1998 | Hall, II et al. |
| 5,977,403 A | 11/1999 | Byers |
| 5,998,350 A | 12/1999 | Burns et al. |
| 6,022,381 A | 2/2000 | Dias et al. |
| 6,068,815 A | 5/2000 | Oberleitner et al. |
| 6,156,156 A | 12/2000 | Rousu et al. |
| 6,177,393 B1 | 1/2001 | McGregor et al. |
| 6,207,632 B1 | 3/2001 | Brooker et al. |
| 6,211,237 B1 * | 4/2001 | Huss ................ C02F 1/722 514/557 |
| 6,221,341 B1 | 4/2001 | Montgomery |
| 6,254,801 B1 | 7/2001 | Reinold et al. |
| 6,284,719 B1 | 9/2001 | Simms |
| 6,284,793 B1 | 9/2001 | Fuchs et al. |
| 6,399,564 B1 | 6/2002 | Speed et al. |
| 6,569,286 B1 | 5/2003 | Withenshaw et al. |
| 6,585,934 B1 | 7/2003 | Oberleitner et al. |
| 6,599,871 B2 | 7/2003 | Smith |
| 6,602,845 B2 | 8/2003 | Connor et al. |
| 6,649,140 B2 | 11/2003 | Paparatto et al. |
| 6,689,732 B1 | 2/2004 | Guedira et al. |
| 7,012,154 B2 | 3/2006 | Vineyard et al. |
| 7,061,597 B2 | 6/2006 | Oberleitner et al. |
| 7,189,385 B2 | 3/2007 | Montgomery |
| 7,217,295 B2 | 5/2007 | Samain et al. |
| 7,569,232 B2 | 8/2009 | Man et al. |
| 7,598,218 B2 | 10/2009 | Stolte et al. |
| 7,915,445 B2 | 3/2011 | Maata et al. |
| 7,919,122 B2 | 4/2011 | Okano et al. |
| 8,802,061 B2 | 8/2014 | Tichy et al. |
| 8,828,910 B2 | 9/2014 | Aksela et al. |
| 8,841,098 B2 | 9/2014 | Payne et al. |
| 8,865,436 B2 | 10/2014 | Payne et al. |
| 8,877,354 B2 | 11/2014 | Horiuchi et al. |
| 9,044,403 B2 | 6/2015 | Schultz |
| 9,192,909 B2 | 11/2015 | Kraus et al. |
| 2003/0100469 A1 | 5/2003 | Connor et al. |
| 2004/0035537 A1 | 2/2004 | Delmas et al. |
| 2004/0097410 A1 | 5/2004 | Zheng et al. |
| 2004/0200619 A1 | 10/2004 | Rae et al. |
| 2005/0008526 A1 | 1/2005 | Bianchetti et al. |
| 2005/0109981 A1 | 5/2005 | Tucker et al. |
| 2006/0177518 A1 | 8/2006 | Stevenson et al. |
| 2007/0100204 A1 | 5/2007 | Feld et al. |
| 2007/0249712 A1 | 10/2007 | Dee et al. |
| 2007/0274857 A1 | 11/2007 | Okano et al. |
| 2008/0176784 A1 | 7/2008 | Clowes et al. |
| 2009/0018049 A1 | 1/2009 | Stolte et al. |
| 2010/0084603 A1 | 4/2010 | Narayan et al. |
| 2010/0159028 A1 | 6/2010 | Shultz |
| 2010/0222242 A1 | 9/2010 | Huang et al. |
| 2010/0286017 A1 | 11/2010 | Righetto |
| 2011/0168567 A1 | 7/2011 | Smith et al. |
| 2011/0169270 A1 | 7/2011 | Todorof |
| 2011/0171062 A1 | 7/2011 | Wolfe |
| 2011/0173897 A1 | 7/2011 | Schneider |
| 2011/0177145 A1 | 7/2011 | Erkenbrecher, Jr. et al. |
| 2012/0136588 A1 | 5/2012 | Kubach |
| 2013/0203849 A1 | 8/2013 | Ben Yehuda |
| 2013/0303844 A1 | 11/2013 | Grudo et al. |
| 2015/0018319 A1 | 1/2015 | Larson et al. |

FOREIGN PATENT DOCUMENTS

| | | |
|---|---|---|
| EP | 2470666 B1 | 7/2014 |
| JP | 62155203 | 7/1987 |
| JP | 6305920 | 11/1994 |
| WO | 9115474 | 10/1991 |
| WO | 9403395 | 2/1994 |
| WO | 9420424 A1 | 9/1994 |
| WO | 9424869 | 11/1994 |
| WO | 9524388 A1 | 9/1995 |
| WO | 9614384 | 5/1996 |
| WO | 9616148 | 5/1996 |
| WO | 9803513 | 1/1998 |
| WO | 9931215 | 6/1999 |
| WO | 0045639 A1 | 8/2000 |
| WO | WO03/006581 * | 1/2003 |
| WO | 2007031596 A2 | 3/2007 |
| WO | 2008088873 A1 | 7/2008 |
| WO | 2010050634 A1 | 5/2010 |
| WO | 2011089313 A2 | 7/2011 |
| WO | 2011159859 A3 | 12/2011 |
| WO | 2013148200 A1 | 10/2013 |
| WO | WO2013/148200 * | 10/2013 |

OTHER PUBLICATIONS

Ebrahimi et al., "Heterogeneously Catalyzed Synthesis of Performic Acid in a Microstructured Reactor," Chemical Engineering Journal 179 (2012) 312-317.

Carboni-Oerlemans, Chiara, et al., "Hydrolase-catalysed synthesis of peroxycarboxylic acids: Biocatalytic promiscuity for practical applications", ScienceDirect, Jounral of Biotechnology 126, p. 140-151. Apr. 7, 2006.

Dannacher, Josef J., "Catalytic bleach: Most valuable applications for smart oxidation chemistry", Journal of Molecular Catalysis A: Chemical 251, p. 159-176. Mar. 20, 2006.

Leveneur, et al., "Synthesis of peroxypropionic acid from propionic acid and hydrogen peroxide over heterogeneous catalysts", Chemical Engineering Journal 147, p. 323-329. Dec. 31, 2009.

Effkemann, et al., "Peroxide analysis in laundry detergents using liquid chromatography", Analytica Chimica Acta 363, p. 97-103. Jan. 2, 1998.

Maeda, et al., Assessment of Acyl Groups and Reaction Conditions in the Competition between Perhydrolysis and Hydrolysis of Acyl Resorufins for Developing an Indicator Reaction for Fluorometric Analysis of Hydrogen Peroxide Feb. 28, 2002.

Muurinen, et al., "Organosolv Pulping: A review and distillation study related to peroxyacid pulping", Department of Proces Engineering, University of Oulu, 75 pages. May 16, 2000.

Ogata, et al., "The Formation of Peracids by the Perhydrolysis With Alkaline Hydrogen Peroxide", Tetrochem., vol. 23, p. 3327-3332. Dec. 31, 1967.

Rusch, et al., "Biocatalytic peroxy acid formation for disinfection", Journal of Molecular Catalysis B: Enzymatic 19-20, p. 499-505. May 16, 2002.

Rusch, et al., "Lipase-catalyzed conversions of trimethylsilyl ethers: deprotection, acetylation, epoxidation and one-pot-multi-step reactions", Journal of Molecular Catalysis B: Enzymatic 7, p. 283-289. Feb. 26, 1999.

Rusch, et al., "Lipase-catalyzed preparation of peroxy acids and their use for epoxidation", Journal of Molecular Catalysis A: Chemical 117, p. 311-319. Dec. 31, 1997.

Tsunokawa, et al., "A Versatile Method for Preparation of O-Alkylperoxycarbonic Acids: Epoxidation With Alkyloxycarbonylimidazoles and Hydrogen Peroxide", Tetrahedron Letters, vol. 23, No. 20. p. 2113-2116. Dec. 31, 1982.

Yin, et al., "Switching Catalysis from Hydrolysis to Perhydrolysis in Pseudomonas fluorescens Esterase", Biochemistry, 49, p. 1931-1942. Dec. 31, 2010.

ECOLAB USA Inc., PCT/IB2011/055830 filed Dec. 20, 2011, "The International Search Report and the Written Opinion of the International Searching Authority, or the Declaration", dated Aug. 24, 2012.

(56) References Cited

OTHER PUBLICATIONS

ECOLAB USA Inc., PCT/IB2011/055832 filed Dec. 20, 2011, "The International Search Report and the Written Opinion of the International Searching Authority, or the Declaration", dated Aug. 14, 2012.
Kramer, J. F., "Peracetic Acid: A New Biocide for Industrial Water Applications", Corrosion 97, Paper No. 404, 16 pages (1997).

\* cited by examiner

METHODS FOR FORMING PEROXYFORMIC ACID AND USES THEREOF

CROSS-REFERENCE TO RELATED APPLICATIONS

This application claims priority under 35 U.S.C. §119 to U.S. Provisional Application Ser. No. 62/094,056 filed Dec. 18, 2014. The entire contents of these patent applications are hereby expressly incorporated herein by reference including, without limitation, the specification, claims, and abstract, as well as any figures, tables, or drawings thereof.

FIELD OF THE INVENTION

The present invention relates generally to methods for forming peroxyformic acid, comprising contacting formic acid with a relatively lower concentration of hydrogen peroxide. The present invention further relates to co-formulations for reaction of formic acid (and optionally other components, such as corrosion inhibitors) with hydrogen peroxide. The present invention also relates to peroxyformic acid formed by these methods. The present invention further relates to the uses of peroxyformic acid for treating a target, e.g., target water, including target water used in connection with oil- and gas-field operations. Other exemplary targets include target water, surface(s) and/or other items used in papermaking, textiles, food, or pharmaceutical industry. The present invention further relates to methods for reducing or removing hydrogen sulfide ($H_2S$) or iron sulfide in a water source, improving clarity of a water source, or reducing the total dissolved oxygen or corrosion in a water source, using peroxyformic acid, including peroxyformic acid generated in situ.

BACKGROUND OF THE INVENTION

An increase in both conventional and unconventional oil and gas exploration has created a necessity for technologies that promote water reuse. Produced water reuse poses numerous challenges that include treatments for iron sulfide, hydrogen sulfide and microbial reduction among others.

Peracid use in the oil and gas industry is gaining wide acceptance because of the versatility, environmental profile and selectiveness of the chemistry. The most commonly used peracid formulation contains peracetic acid ($CH_3COOOH$) and hydrogen peroxide in equilibrium. However one of the caveats of any peracetic acid, hydrogen peroxide formulation is the formation of oxygen in the treatment vessel. Oxygen production increases the risk of corrosion significantly. Therefore, the use of such formulations has been limited to onshore as well as open systems. Thus there is a need to seek alternative ways to treat the water in oil and gas industry that has the same or better performance as peracetic acid systems, but reduce or minimize oxygen related corrosion issues. The present disclosure addresses this and the related needs using, inter alia, performic acid.

BRIEF SUMMARY OF THE INVENTION

The present invention relates generally to methods for forming peroxyformic acid, comprising contacting formic acid with hydrogen peroxide. In an aspect the contracting of formic acid is with a relatively lower concentration of hydrogen peroxide. In another aspect, the formic acid is formulated with a corrosion inhibitor or other additional functional ingredient. In another aspect, the formic acid contacts a peroxycarboxylic acid composition containing hydrogen peroxide. In an aspect, the contacting step forms a peroxyformic acid within a desired time frame and can be treated or contacted under various conditions, such as treated with a cation exchange resin such as a strong acid resin column, heated to a desired temperature, or passing through a micro reactor under specific conditions.

In one aspect, the present invention is directed to a method for forming peroxyformic acid comprising contacting formic acid with hydrogen peroxide to form a resulting aqueous composition that comprises a peracid that comprises peroxyformic acid, wherein before said contacting, the ratio between the concentration of said formic acid (w/v) and the concentration of said hydrogen peroxide (w/v) is about 2 or higher, and the ratio between the concentration of said peracid (w/w) and the concentration of hydrogen peroxide (w/w) in said formed resulting aqueous composition reaches about 2 or higher at least within 4 hours, or preferably 2 hours of said contacting.

In another aspect, the present invention is directed to peroxyformic acid formed using the above method.

In still another aspect, the present invention is directed to a method for treating a target, which method comprises contacting a target with an effective amount of peroxyformic acid formed using the above method to form a treated target composition, wherein said treated target composition comprises from about 0.1 ppm to about 1,000 ppm of said peroxyformic acid, and preferably, said contacting lasts for sufficient time to stabilize or reduce microbial population in and/or on said target or said treated target composition. The present invention further relates to the uses of peroxyformic acid for treating a target, e.g., target water, including target water used in connection with oil- and gas-field operations. The present invention further relates to methods for reducing or removing hydrogen sulfide ($H_2S$) or iron sulfide in a water source, improving clarity of a water source, or reducing the total dissolved oxygen or corrosion in a water source, using peroxyformic acid, including peroxy formic acid generated in situ.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
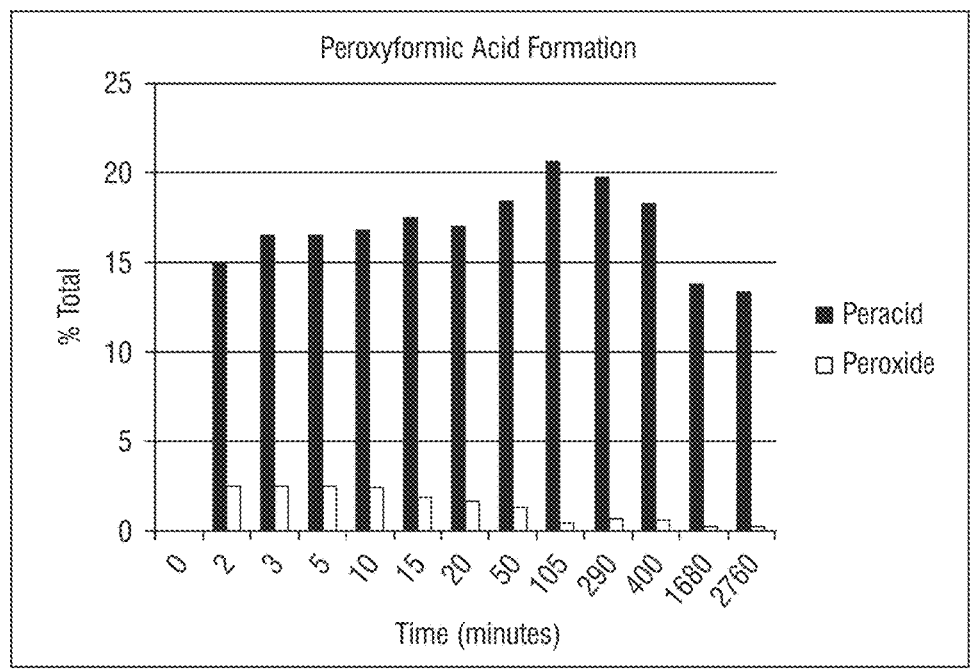
FIG. 1 illustrates formation of peroxyformic acid via addition of formic acid to a peracetic acid/hydrogen peroxide system according to embodiments of the invention.

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE INVENTION

The embodiments of this invention are not limited to particular peroxyformic acid forming compositions, methods for forming peroxyformic acid, the formed peroxyformic acid and methods for using the same, which can vary and are understood by skilled artisans. It is further to be understood that all terminology used herein is for the purpose of describing particular embodiments only, and is not intended to be limiting in any manner or scope. For example, all units, prefixes, and symbols may be denoted in its SI accepted form. Numeric ranges recited within the specification are inclusive of the numbers defining the range and include each integer within the defined range.

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference. So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

It should be noted that, as used in this specification and the appended claims, the singular forms "a," "an," and "the" include plural referents unless the content clearly dictates otherwise. Thus, for example, reference to a composition containing "a compound" includes a composition having two or more compounds. It should also be noted that the term "or" is generally employed in its sense including "and/or" unless the content clearly dictates otherwise.

As used herein, the term "about" refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "actives" or "percent actives" or "percent by weight actives" or "actives concentration" are used interchangeably herein and refers to the concentration of those ingredients involved in cleaning expressed as a percentage minus inert ingredients such as water or salts.

As used herein, the phrase "brewery surface" refers to a surface of a tool, a machine, equipment, a structure, a building, or the like that is employed as part of a brewing, making, distilling, preparation, bottling, canning, and storage, etc. of beer, wine, liquor, and spirits. Brewery surface is intended to encompass all surfaces used in brewing (including beer brewing and preparation of liquors and spirits) and winemaking processes. Examples of brewery surfaces include fermentation vessels, bright beer tanks and lines, mash tuns, bottling equipment, pipes, storage vessels, bottling and canning equipment, etc.

As used herein, the phrases "CIP equipment" and "CIP tank" or any variations thereof, refer to tanks, vessels, apparatuses, lines, pumps, and other process equipment used for processing typically liquid product streams such as beverages, milk, juices, etc. used in CIP cleaning techniques for removing soils from the internal components. It encompasses any CIP food processing surfaces and CIP brewery surfaces.

The term "cleaning," as used herein, means to perform or aid in soil removal, bleaching, microbial population reduction, or combination thereof. For the purpose of this patent application, successful microbial reduction is achieved when the microbial populations are reduced by at least about 50%, or by significantly more than is achieved by a wash with water. Larger reductions in microbial population provide greater levels of protection.

As used herein, "consisting essentially of" means that the methods and compositions may include additional steps, components, ingredients or the like, but only if the additional steps, components and/or ingredients do not materially alter the basic and novel characteristics of the claimed methods and compositions.

As used herein, the term "disinfectant" refers to an agent that kills all vegetative cells including most recognized pathogenic microorganisms, using the procedure described in *A.O.A.C. Use Dilution Methods*, Official Methods of Analysis of the Association of Official Analytical Chemists, paragraph 955.14 and applicable sections, 15th Edition, 1990 (EPA Guideline 91-2). As used herein, the term "high level disinfection" or "high level disinfectant" refers to a compound or composition that kills substantially all organisms, except high levels of bacterial spores, and is effected with a chemical germicide cleared for marketing as a sterilant by the Food and Drug Administration. As used herein, the term "intermediate-level disinfection" or "intermediate level disinfectant" refers to a compound or composition that kills mycobacteria, most viruses, and bacteria with a chemical germicide registered as a tuberculocide by the Environmental Protection Agency (EPA).

As used herein, the term "low-level disinfection" or "low level disinfectant" refers to a compound or composition that kills some viruses and bacteria with a chemical germicide registered as a hospital disinfectant by the EPA.

As used herein, the phrase "food processing surface" refers to a surface of a tool, a machine, equipment, a structure, a building, or the like that is employed as part of a food or beverage processing, preparation, or storage activity. Food processing surface is intended to encompass all surfaces used in brewing (including beer brewing and preparation of liquors and spirits) and winemaking processes (e.g., bright beer tanks and lines, fermentation vessels, mash tuns, bottling equipment, pipes, and storage vessels). Examples of food processing surfaces include surfaces of food processing or preparation equipment (e.g., boiling, fermenting, slicing, canning, or transport equipment, including flumes), of food processing wares (e.g., utensils, dishware, wash ware, and bar glasses), and of floors, walls, or fixtures of structures in which food processing occurs. Food processing surfaces are found and employed in food anti-spoilage air circulation systems, aseptic packaging sanitizing, food refrigeration and cooler cleaners and sanitizers, ware washing sanitizing, blancher cleaning and sanitizing, food packaging materials, cutting board additives, third-sink sanitizing, beverage chillers and warmers, meat chilling or scalding waters, autodish sanitizers, sanitizing gels, cooling towers, food processing antimicrobial garment sprays, and non-to-low-aqueous food preparation lubricants, oils, and rinse additives.

As used herein, the phrase "food product" includes any food substance that might require treatment with an antimicrobial agent or composition and that is edible with or without further preparation. Food products include meat (e.g. red meat and pork), seafood, poultry, produce (e.g., fruits and vegetables), eggs, living eggs, egg products, ready to eat food, wheat, seeds, roots, tubers, leafs, stems, corns, flowers, sprouts, seasonings, or a combination thereof. The term "produce" refers to food products such as fruits and vegetables and plants or plant-derived materials that are typically sold uncooked and, often, unpackaged, and that can sometimes be eaten raw.

As used herein, the term "free," "no," "substantially no" or "substantially free" refers to a composition, mixture, or ingredient that does not contain a particular compound or to which a particular compound or a particular compound-containing compound has not been added. In some embodiments, the reduction and/or elimination of hydrogen peroxide according to embodiments provide hydrogen peroxide-free or substantially-free compositions. Should the particular compound be present through contamination and/or use in a minimal amount of a composition, mixture, or ingredients, the amount of the compound shall be less than about 3 wt-%. More preferably, the amount of the compound is less than 2 wt-%, less than 1 wt-%, and most preferably the amount of the compound is less than 0.5 wt-%.

The term "hard surface" refers to a solid, substantially non-flexible surface such as a counter top, tile, floor, wall, panel, window, plumbing fixture, kitchen and bathroom furniture, appliance, engine, circuit board, and dish. Hard surfaces may include for example, health care surfaces and food processing surfaces.

As used herein, the term "microorganism" refers to any noncellular or unicellular (including colonial) organism Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

As used herein, the terms "mixed" or "mixture" when used relating to "percarboxylic acid composition," "percarboxylic acids," "peroxycarboxylic acid composition" or "peroxycarboxylic acids" refer to a composition or mixture including more than one percarboxylic acid or peroxycarboxylic acid.

As used herein, the term "sanitizer" refers to an agent that reduces the number of bacterial contaminants to safe levels as judged by public health requirements. In an embodiment, sanitizers for use in this invention will provide at least a 99.999% reduction (5-log order reduction). These reductions can be evaluated using a procedure set out in *Germicidal and Detergent Sanitizing Action of Disinfectants*, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 25+2° C., against several test organisms.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic. A sanitizer and a disinfectant are, by definition, agents which provide antimicrobial or microbiocidal activity. In contrast, a preservative is generally described as an inhibitor or microbistatic composition.

As used herein, the term "water" for treatment according to the invention includes a variety of sources, such as freshwater, pond water, sea water, salt water or brine source, brackish water, recycled water, or the like. Waters are also understood to optionally include both fresh and recycled water sources (e.g. "produced waters"), as well as any combination of waters for treatment according to the invention. In some embodiments, produced water (or reuse water) refers to a mixture of water that comprises both water recycled from previous or concurrent oil- and gas-field operations, e.g., fracking, and water that has not been used in oil- and gas-field operations, e.g., fresh water, pond water, sea water, etc.

As used herein, "weight percent," "wt-%," "percent by weight," "% by weight," and variations thereof refer to the concentration of a substance as the weight of that substance divided by the total weight of the composition and multiplied by 100. It is understood that, as used here, "percent," "%," and the like are intended to be synonymous with "weight percent," "wt-%," etc.

It is understood that aspects and embodiments of the invention described herein include "consisting" and/or "consisting essentially of" aspects and embodiments.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Methods for forming peroxyformic acid

In one aspect, the present invention is directed to a method for forming peroxyformic acid comprising contacting formic acid with hydrogen peroxide to form a resulting aqueous composition that comprises a peracid that comprises peroxyformic acid, wherein before said contacting, the ratio between the concentration of said formic acid (w/v) and the concentration of said hydrogen peroxide (w/v) is about 2 or higher, and the ratio between the concentration of said peracid (w/w) and the concentration of hydrogen peroxide (w/w) in said formed resulting aqueous composition reaches about 2 or higher at least within 4 hours, or preferably 2 hours of said contacting.

The formic acid used in the present methods can be provided in any suitable way. In some embodiments, before the contacting step, the formic acid can be provided in a composition that comprises formic acid, e.g., an aqueous solution that comprises formic acid. In other embodiments, before the contacting step, the formic acid can be provided in a composition that comprises a substance that generates formic acid upon contact with an aqueous composition. Any suitable substance that generates formic acid can be used in the present methods. The substance can be a salt of formate, e.g., a sodium or ammonium salt of formate, or an ester of formate. Exemplary esters of formate include glycerol formates, pentaerythritol formates, mannitol formates, propylene glycol formates, sorbitol formates and sugar formates. Exemplary sugar formates include sucrose formates, dextrin formates, maltodextrin formates, and starch formates. In some embodiments the formates may be provided in a solid composition, such as a starch formate.

The hydrogen peroxide used in the present methods can be provided in any suitable way. In some embodiments, before the contacting step, the hydrogen peroxide can be provided in a composition that comprises hydrogen peroxide, e.g., an aqueous solution that comprises hydrogen peroxide. In other embodiments, before the contacting step, the hydrogen peroxide can be provided in a composition that comprises a substance that generates hydrogen peroxide upon contact with an aqueous composition. Any suitable substance that generates hydrogen peroxide can be sued in the present methods. The substance can comprise a precursor of hydrogen peroxide. Any suitable precursor of hydrogen peroxide can be used in the present methods. For example, the precursor of hydrogen peroxide can be sodium percarbonate, sodium perborate, urea hydrogen peroxide, or PVP-hydrogen peroxide.

In some embodiments, formic acid provided in a first aqueous composition is contacted with hydrogen peroxide provided in a second aqueous composition to form peroxyformic acid in the resulting aqueous composition. In other embodiments, formic acid provided in a first aqueous composition is contacted with a substance that generates hydrogen peroxide upon contact with an aqueous composition provided in a second solid composition to form peroxyformic acid in the resulting aqueous composition. In still other embodiments, a substance that generates formic acid upon contact with an aqueous composition provided in a first solid composition is contacted with hydrogen peroxide provided in a second aqueous composition to form peroxyformic acid in the resulting aqueous composition. In yet other embodiments, a substance that generates formic acid upon contact with an aqueous composition provided in a first solid composition and a substance that generates hydrogen peroxide upon contact with an aqueous composition provided in a second solid composition are contacted with a third aqueous composition to form peroxyformic acid in the resulting aqueous composition. In yet other embodiments, a substance that generates formic acid upon contact with an aqueous composition and a substance that generates hydrogen peroxide upon contact with an aqueous composition are provided in a first solid composition, and the first solid composition is contacted with a second aqueous composition to form peroxyformic acid in the resulting aqueous composition.

The resulting aqueous composition that comprises a peracid that comprises peroxyformic acid can be any suitable types of aqueous compositions. For example, the resulting aqueous composition can be an aqueous solution. In another example, the resulting aqueous composition can be an aqueous suspension.

Before the contacting step, the ratio between the concentration of the formic acid (w/v) and the concentration of the hydrogen peroxide (w/v) can be in any suitable range. In some embodiments, before the contacting, the ratio between the concentration of the formic acid (w/v) and the concentration of the hydrogen peroxide (w/v) can be from about 2 to about 100, e.g., about 2-3, 3-4, 4-5, 5-6, 6-7, 7-8, 8-9, 9-10, 10-15, 15-20, 20-25, 25-30, 30-35, 35-40, 40-45 or 45-50 or greater from about 50-100.

The ratio between the concentration of the peracid (w/w) and the concentration of hydrogen peroxide (w/w) in the formed aqueous composition can reach any suitable range. In some embodiments, the ratio between the concentration of the peracid (w/w) and the concentration of hydrogen peroxide (w/w) in the formed aqueous composition can reach, within about 4 hours, or preferably 2 hours of the contacting, from about 2 to about 1,500, e.g., about 2-3, 3-4, 4-5, 5-6, 6-7, 7-8, 8-9, 9-10, 10-15, 15-20, 20-25, 25-30, 30-35, 35-40, 40-45, 45-50, 50-60, 60-70, 70-80, 80-90, 90-100, 100-200, 200-300, 300-400, 400-500, 500-600, 600-700, 700-800, 800-900, 900-1,000, 1,000-1,100, 1,100-1,200, 1,200-1,300, 1,300-1,400, or 1,400-1,500. In other embodiments, the ratio between the concentration of the peracid (w/w) and the concentration of hydrogen peroxide (w/w) in the formed aqueous composition reaches at least about 10 within about 30 minutes of the contacting, preferably at least about 10-40 within about 30 minutes of the contacting.

The formed aqueous composition can comprise any suitable concentration of hydrogen peroxide. In some embodiments, the formed aqueous composition can comprise about 5% (w/w) or less hydrogen peroxide, e.g., about 5% (w/w), 4.5% (w/w), 4% (w/w), 3.5% (w/w), 3% (w/w), 2.5% (w/w), 2% (w/w), 1.5% (w/w), 1% (w/w), 0.9% (w/w), 0.8% (w/w), 0.7% (w/w), 0.6% (w/w), 0.5% (w/w), 0.4% (w/w), 0.3% (w/w), 0.2% (w/w), 0.1% (w/w), 0.05% (w/w), 0.01% (w/w), 0.005% (w/w), or 0.001% (w/w) of hydrogen peroxide. In other embodiments, the formed aqueous composition reaches about 2% (w/w) or less hydrogen peroxide within at least about 4 hours, or preferably 2 hours of the contacting. In still other embodiments, the formed aqueous composition reaches about 1% (w/w) or less hydrogen peroxide within at least about 1 hour of the contacting. In yet other embodiments, the formed aqueous composition reaches about 0% (w/w) to about 0.001% (w/w) hydrogen peroxide and maintains about 0% (w/w) to about 0.001% (w/w) hydrogen peroxide for at least 1 hour.

The formic acid and the hydrogen peroxide can be contacted in the absence of a $C_2$-$C_{22}$ carboxylic acid and/or a $C_2$-$C_{22}$ percarboxylic acid and the peracid in the formed aqueous composition comprises peroxyformic acid only.

The formic acid and hydrogen peroxide can be contacted in the presence of a $C_2$-$C_{22}$ carboxylic acid and the peracid in the formed aqueous composition comprises peroxyformic acid and the $C_2$-$C_{22}$ percarboxylic acid. Any suitable $C_2$-$C_{22}$ carboxylic acid can be used in the present methods. In some embodiments, the $C_2$-$C_{22}$ carboxylic acid is acetic acid, octanoic acid and/or sulfonated oleic acid, and the peracid in the formed aqueous composition comprises peroxyformic acid and one or more of peroxyacetic acid, peroxyoctanoic acid and peroxysulfonated oleic acid.

The formic acid and the hydrogen peroxide can be contacted in the presence of a $C_2$-$C_{22}$ percarboxylic acid and the peracid in the formed aqueous composition comprises peroxyformic acid and the $C_2$-$C_{22}$ percarboxylic acid. Any suitable $C_2$-$C_{22}$ percarboxylic acid can be used in the present methods. In some embodiments, the $C_2$-$C_{22}$ percarboxylic acid can be peroxyacetic acid, peroxyoctanoic acid and/or peroxysulfonated oleic acid.

The present methods can be conducted at any suitable temperature. In some embodiments, the present methods can be conducted at a temperature ranging from about −2° C. to about 70° C., about 10° C. to about 70° C., e.g., about 10° C.-15° C., 15° C.-20° C., 20° C.-25° C., 25° C.-30° C., 30° C.-35° C., 35° C.-40° C., 40° C.-45° C., 45° C.-50° C., 50° C.-55° C., 55° C.-60° C., 60° C.-65° C., or 65° C.-70° C. In other embodiments, the present methods can be conducted under ambient conditions. In still other embodiments, the present methods can be conducted under heating, e.g., at a temperature ranging from about 30° C.-35° C., 35° C.-40° C., 40° C.-45° C., 45° C.-50° C., 50° C.-55° C., 55° C.-60° C., 60° C.-65° C., or 65° C.-70° C.

The present methods can be conducted in the presence of a catalyst. Any suitable catalyst can be used in the present methods. In some embodiments, the catalyst can be a mineral acid, e.g., sulfuric acid, methanesulfonic acid, nitric acid, phosphoric acid, pyrophosphoric acid, polyphosphoric acid or phosphonic acid.

The present methods can be conducted in the presence of a cation acid exchange resin system. Any suitable cation acid exchange resin system can be used in the present methods. In some embodiments, the cation acid exchange resin system is a strong cation acid exchange resin system. In other embodiments, the acid exchange resin system is sulfonic acid exchange resin, e.g., commercially-available as Dowex M-31 or Nafion.

The formic acid provided in a first aqueous composition can be contacted with the hydrogen peroxide provided in a second aqueous composition that also comprises peroxyacetic acid to form a resulting aqueous composition that comprises a total peracid that comprises peroxyformic acid and peroxyacetic acid. Before the contacting step, the ratio between the concentration of the formic acid (w/v) and the concentration of the hydrogen peroxide (w/v) can be at any suitable range. The ratio between the concentration of total peracid (w/w) and the concentration of hydrogen peroxide (w/w) in the resulting aqueous composition can also reach any suitable range. In some embodiments, before the contacting, the ratio between the concentration of the formic acid (w/v) and the concentration of the hydrogen peroxide (w/v) can be about 5 or higher and the ratio between the concentration of total peracid (w/w) and the concentration of hydrogen peroxide (w/w) in the resulting aqueous composition reaches at least about 5 within about 2 minutes of the contacting. In other embodiments, the ratio between the concentration of total peracid (w/w) and the concentration of hydrogen peroxide (w/w) in the resulting aqueous composition can reach at least about 10 within about 20 minutes of the contacting. In still other embodiments, the ratio between the concentration of total peracid (w/w) and the concentration of hydrogen peroxide (w/w) in the resulting aqueous composition can reach at least about 50 within about 30 hours of the contacting. In yet other embodiments, before the contacting, the ratio between the concentration of the formic acid (w/v) and the concentration of the hydrogen peroxide (w/v) can be about 20 or higher and the ratio between the concentration of total peracid (w/w) and the concentration of hydrogen peroxide (w/w) in the resulting aqueous composition can reach at least about 10 within at least about 1 minute of the contacting. The concentration of hydrogen peroxide (w/w) in the resulting aqueous composition can reach any suitable concentration. In some embodiments, the concentration of hydrogen peroxide (w/w) in the resulting aqueous composition can reach about 0% (w/w) to about 0.001% (w/w) hydrogen peroxide within at least about 4 hours, or preferably 2 hours of the contacting. In other embodiments, the concentration of hydrogen peroxide (w/w) in the resulting aqueous composition can remain at about 0% (w/w) to about 0.001% (w/w) for least 1 hour.

The formic acid provided in a first aqueous composition can be contacted with the hydrogen peroxide provided in a second aqueous composition that also comprises peroxyoctanoic acid to form a resulting aqueous composition that comprises a total peracid that comprises peroxyformic acid and peroxyoctanoic acid. Before the contacting step, the ratio between the concentration of the formic acid (w/v) and the concentration of the hydrogen peroxide (w/v) can be at any suitable range. The ratio between the concentration of total peracid (w/w) and the concentration of hydrogen peroxide (w/w) in the resulting aqueous composition can also reach any suitable range. In some embodiments, the ratio between the concentration of the formic acid (w/v) and the concentration of the hydrogen peroxide (w/v) can be about 5 or higher and the ratio between the concentration of total peracid (w/w) and the concentration of hydrogen peroxide (w/w) in the resulting aqueous composition can reach at least about 5 within at least about 30 minutes of the contacting.

In some embodiments, a salt of formate or an ester of formate in a first composition, e.g., a first solid or liquid composition, can be contacted with hydrogen peroxide and a $C_2$-$C_{22}$ percarboxylic acid provided in a second aqueous composition to form a resulting aqueous composition that comprises peroxyformic acid and the $C_2$-$C_{22}$ percarboxylic acid. Before the contacting, the second aqueous composition can comprise any suitable concentration of the $C_2$-$C_{22}$ percarboxylic acid, and the salt of formate or ester of formate can be added to the second aqueous composition so that the aqueous composition comprises any suitable concentration of the salt of formate or ester of formate. The ratio between the concentration of total peracid (w/w) and the concentration of hydrogen peroxide (w/w) in the resulting aqueous composition can reach any suitable range. For example, before the contacting, the second aqueous composition comprises from about 1 (w/v) to about 40 (w/v) of the $C_2$-$C_{22}$ percarboxylic acid, the salt of formate or ester of formate is added to the second aqueous composition so that the aqueous composition comprises from about 5 (w/v) to about 30 (w/v) of the salt of formate or ester of formate, and the ratio between the concentration of total peracid (w/w) and the concentration of hydrogen peroxide (w/w) in the resulting aqueous composition reaches at least about 2 within at least about 3 hours of the contacting. In another example, the concentration of hydrogen peroxide (w/w) in the resulting aqueous composition can reach about 0.001% (w/w) to about 10% (w/w) within at least about 3 hours of the contacting.

The resulting aqueous composition can comprise a stabilizing agent for the peracid. Any suitable stabilizing agents can be used in the present methods. Exemplary stabilizing agents include a phosphonate salt(s) and/or a heterocyclic dicarboxylic acid, e.g., dipicolinic acid.

The present methods can further comprise a step of reducing the concentration of the hydrogen peroxide in the resulting aqueous composition. The concentration of the hydrogen peroxide in the resulting aqueous composition can be reduced using any suitable methods. For example, the concentration of the hydrogen peroxide in the resulting aqueous composition can be reduced using a catalase or a peroxidase.

The resulting aqueous composition can comprise any suitable concentration of peroxyformic acid. In some embodiments, the resulting aqueous composition comprises from about 0.001% (w/w) to about 20% (w/w) peroxyformic acid, e.g., about 0.001%-0.005% (w/w), 0.005%-0.01% (w/w), 0.01%-0.05% (w/w), 0.05%-0.1% (w/w), 0.1%-0.5% (w/w), 0.5%-1% (w/w), 1%-2% (w/w), 2%-3% (w/w), 3%-4% (w/w), 4%-5% (w/w), 5%-6% (w/w), 6%-7% (w/w), 7%-8% (w/w), 8%-9% (w/w), 9%-10% (w/w), 10%-11% (w/w), 11%-12% (w/w) 12%-13% (w/w) 13%-14% (w/w) 14%-15% (w/w) 15%-16% (w/w) 16%-17% (w/w) 17%-18% (w/w) 18%-19% (w/w) 19%-20% (w/w) peroxyformic acid.

The present methods can further comprise adding a corrosion inhibitor so that the formed resulting aqueous composition comprises the corrosion inhibitor. Any suitable corrosion inhibitor can be used. In some embodiments, the corrosion inhibitor can be a phosphate ester, a derivative of the phosphate ester, a diacid, a derivative of the diacid, a quat amine, a derivative of the quat amine, an imidazoline, a derivative of the imidazoline, an alkyl pyridine, a derivative of the alkyl pyridine, a phosphonium salt, a derivative of the phosphonium salt, or a combination thereof.

The corrosion inhibitor can be used at any suitable concentration. In some embodiments, the formed resulting aqueous composition can comprise from about 0.1 ppm to about 50,000 ppm of the corrosion inhibitor, e.g., about 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm, 1,000-1,500 ppm, 1,500-2,000 ppm, 2,000-2,500 ppm, 2,500-3,000 ppm, 3,000-3,500 ppm, 3,500-4,000 ppm, 4,000-4,500 ppm, or 4,500-5,000 ppm, 5,000-5,500 ppm, 5,500-6,000 ppm, 6,000-6,500 ppm, 6,500-7,000 ppm, 7,000-7,500 ppm, 7,500-8,000, 8,000-8,500 ppm, 8,500-9,000 ppm, 9,000-9,500 ppm, or 9,500-10,000 ppm. In other embodiments, the ratio between the concentration of the peroxyformic acid (w/v) and the concentration of the corrosion inhibitor (w/v) in the formed resulting aqueous composition can be from about 0.01 to about 100, e.g., about 0.01-0.05, 0.05-0.1, 0.1-0.5, 0.5-1, 1-2, 2-3, 3-4, 4-5, 5-6, 6-7, 7-8, 8-9, 9-10, 10-15, 15-20, 20-25, 25-30, 30-35, 35-40, 40-45, 45-50, 50-60, 60-70, 70-80, 80-90, 90-100.

The corrosion inhibitor can be added at any suitable time. In some embodiments, the corrosion inhibitor can be added before the formic acid is contacted with the hydrogen peroxide. In other embodiments, the corrosion inhibitor can be added concurrently when the formic acid is contacted with the hydrogen peroxide. In still other embodiments, the corrosion inhibitor can be added after the formic acid is contacted with the hydrogen peroxide.

The present methods can be used to generate peroxyformic acid in any suitable manner or at any suitable location. In some embodiments, the present methods can be used to generate peroxyformic acid in situ for the application of the formed peroxyformic acid.

In another aspect, the present invention is directed to peroxyformic acid formed using the present methods, e.g., peroxyformic acid formed in situ for the application of the formed peroxyformic acid, and a peroxyformic acid formed composition formed using the present methods in the presence of a corrosion inhibitor.

The peroxyformic acid formed using the present methods (present composition) can further comprise other percarboxylic acids. Various embodiments of the invention referring to peroxyformic acid compositions and/or peroxyformic acid solutions are further understood to optionally comprise additional percarboxylic acids. As used herein, the term "peracid" may also be referred to as a "percarboxylic acid" or "peroxyacid." Sulfoperoxycarboxvlic acids, sulfonated peracids and sulfonated peroxycarboxylic acids are also included within the term "peracid" as used herein. The terms "sulfoperoxycarboxylic acid," "sulfonated peracid," or "sulfonated peroxycarboxylic acid" refers to the peroxycarboxylic acid form of a sulfonated carboxylic acid as disclosed in U.S. Patent Publication Nos. 2010/0021557, 2010/0048730 and 2012/0052134 which are incorporated herein by reference in their entireties. A peracid refers to an acid having the hydrogen of the hydroxyl group in carboxylic acid replaced by a hydroxy group. Oxidizing peracids may also be referred to herein as peroxycarboxylic acids.

In some embodiments, peroxyformic acid with other peroxycarboxylic acids can be generated by mixing an ester of a polyhydric alcohol with a composition comprising peroxycaboxylic acid(s) and hydrogen peroxide to form a composition that comprises both peroxyformic acid and other peroxycarboxylic acids. Examples of commercially-available compositions comprising both peroxycarboxylic acid and hydrogen peroxide include peroxyacetic acid compositions, peroxyoctanoic acid compositions, etc. all commercially available from Ecolab Inc. In use, an ester of a polyhydric alcohol can be contacted, e.g., mixed, with such peroxyacetic acid compositions, peroxyoctanoic acid compositions, etc., to form a composition that comprises both peroxyformic acid and other desired peroxycarboxylic acids.

A peracid includes any compound of the formula R—(COOOH)$_n$ in which R can be hydrogen, alkyl, alkenyl, alkyne, acylic, alicyclic group, aryl, heteroaryl, or heterocyclic group, and n is 1, 2, or 3, and named by prefixing the parent acid with peroxy. Preferably R includes hydrogen, alkyl, or alkenyl. The terms "alkyl," "alkenyl," "alkyne," "acylic," "alicyclic group," "aryl," "heteroaryl," and "heterocyclic group" are as defined herein.

As used herein, the term "alkyl" includes a straight or branched saturated aliphatic hydrocarbon chain having from 1 to 22 carbon atoms, such as, for example, methyl, ethyl, propyl, isopropyl (1-methylethyl), butyl, tert-butyl (1,1-dimethylethyl), and the like. The term "alkyl" or "alkyl groups" also refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkvylsulfinyl, sulfonates, sulfamoyl, sulfonamido, nitro, trifluoromethyl, cyano, azido, heterocyclic, alkylaryl, or aromatic (including heteroaromatic) groups.

The term "alkenyl" includes an unsaturated aliphatic hydrocarbon chain having from 2 to 12 carbon atoms, such as, for example, ethenyl, 1-propenyl, 2-propenyl, 1-butenyl, 2-methyl-1-propenyl, and the like. The alkyl or alkenyl can be terminally substituted with a heteroatom, such as, for example, a nitrogen, sulfur, or oxygen atom, forming an aminoalkyl, oxyalkyl, or thioalkyl, for example, aminomethyl, thioethyl, oxypropyl, and the like. Similarly, the above alkyl or alkenyl can be interrupted in the chain by a heteroatom forming an alkylaminoalkyl, alkylthioalkyl, or alkoxyalkyl, for example, methylaminoethyl, ethylthiopropyl, methoxymethyl, and the like.

Further, as used herein the term "alicyclic" includes any cyclic hydrocarbyl containing from 3 to 8 carbon atoms. Examples of suitable alicyclic groups include cyclopropanyl, cyclobutanyl, cyclopentanyl, etc. The term "heterocyclic" includes any closed ring structures analogous to carbocyclic groups in which one or more of the carbon atoms in the ring is an element other than carbon (heteroatom), for example, a nitrogen, sulfur, or oxygen atom. Heterocyclic groups may be saturated or unsaturated. Examples of suitable heterocyclic groups include for example, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan. Additional examples of suitable heterocyclic groups include groups derived from tetrahydrofurans, furans, thiophenes, pyrrolidines, piperidines, pyridines, pyrrols, picoline, coumaline, etc.

In some embodiments, alkyl, alkenyl, alicyclic groups, and heterocyclic groups can be unsubstituted or substituted by, for example, aryl, heteroaryl, $C_{1-4}$ alkyl, $C_{1-4}$ alkenyl, $C_{1-4}$ alkoxy, amino, carboxy, halo, nitro, cyano, —$SO_3H$, phosphono, or hydroxy. When alkyl, alkenyl, alicyclic group, or heterocyclic group is substituted, preferably the substitution is $C_{1-4}$ alkyl, halo, nitro, amido, hydroxy, carboxy, sulpho, or phosphono. In one embodiment, R includes alkyl substituted with hydroxy. The term "aryl" includes aromatic hydrocarbyl, including fused aromatic rings, such as, for example, phenyl and naphthyl. The term "heteroaryl" includes heterocyclic aromatic derivatives having at least one heteroatom such as, for example, nitrogen, oxygen, phosphorus, or sulfur, and includes, for example, furyl, pyrrolyl, thienyl, oxazolyl, pyridyl, imidazolyl, thiazolyl, isoxazolyl, pyrazolyl, isothiazolyl, etc. The term "heteroaryl" also includes fused rings in which at least one ring is aromatic, such as, for example, indolyl, purinyl, benzofuryl, etc.

In some embodiments, aryl and heteroaryl groups can be unsubstituted or substituted on the ring by, for example, aryl, heteroaryl, alkyl, alkenyl, alkoxy, amino, carboxy, halo, nitro, cyano, —$SO_3H$, phosphono, or hydroxy. When aryl, aralkyl, or heteroaryl is substituted, preferably the substitution is $C_{1-4}$ alkyl, halo, nitro, amido, hydroxy, carboxy, sulpho, or phosphono. In one embodiment, R includes aryl substituted with $C_{1-4}$ alkyl.

Peracids suitable for use include any peroxycarboxylic acids, including varying lengths of peroxycarboxylic and percarboxylic acids (e.g. C1-22) that can be prepared from the acid-catalyzed equilibrium reaction between a carboxylic acid described above and hydrogen peroxide. Additional suitable peracids include those prepared from the reaction of an ester of a polyhydric alcohol and formic acid with hydrogen peroxide. A peroxycarboxylic acid can also be prepared by the auto-oxidation of aldehydes or by the reaction of hydrogen peroxide with an acid chloride, acid hydride, carboxylic acid anhydride, or sodium alcoholate. Alternatively, peracids can be prepared through non-equilibrium reactions, which may be generated for use in situ, such as the methods disclosed in U.S. Pat. Nos. 8,846,107 and 8,877,254 each titled "In Situ Generation of Peroxycarboxylic Acids at Alkaline pH, and Methods of Use Thereof," which are incorporated herein by reference. Preferably a composition of the invention includes peroxyformic acid, peroxyacetic acid, peroxyoctanoic acid, peroxypropionic acid, peroxylactic acid, peroxyheptanoic acid, peroxyoctanoic acid and/or peroxynonanoic acid.

In some embodiments, a peroxycarboxylic acid includes at least one water-soluble peroxycarboxylic acid in which R includes alkyl of 1-22 carbon atoms. For example, in one embodiment, a peroxycarboxylic acid includes peroxyformic acid and/or peroxyacetic acid. In another embodiment, a peroxycarboxylic acid has R that is an alkyl of 1-22 carbon atoms substituted with hydroxy. Methods of preparing peroxyacetic acid are known to those of skill in the art including those disclosed in U.S. Pat. No. 2,833,813, which is herein incorporated herein by reference.

In another embodiment, a sulfoperoxycarboxylic acid has the following formula:

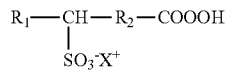

wherein $R_1$ is hydrogen, or a substituted or unsubstituted alkyl group; $R_2$ is a substituted or unsubstituted alkylene group; X is hydrogen, a cationic group, or an ester forming moiety; or salts or esters thereof. In additional embodiments, a sulfoperoxycarboxylic acid is combined with a single or mixed peroxycarboxylic acid composition, such as a sulfoperoxycarboxylic acid with peroxyacetic acid and peroxyoctanoic acid (PSOA/POOA/POAA).

In other embodiments, a mixed peracid is employed, such as a peroxycarboxylic acid including at least one peroxycarboxylic acid of limited water solubility in which R includes alkyl of 5-22 carbon atoms and at least one water-soluble peroxycarboxylic acid in which R includes alkyl of 1-4 carbon atoms. For example, in one embodiment, a peroxycarboxylic acid includes peroxyacetic acid and at least one other peroxycarboxylic acid such as those named above. Preferably a composition of the invention includes peroxyformic acid, peroxyacetic acid and/or peroxyoctanoic acid. Other combinations of mixed peracids are well suited for use in the current invention.

In another embodiment, a mixture of peroxyformic acid, and peracetic acid or peroctanoic acid is used to treat a water source, such as disclosed in U.S. Pat. No. 5,314,687 which is herein incorporated by reference in its entirety. In an aspect, the peracid mixture is a hydrophilic peroxyformic acid or peracetic acid and a hydrophobic peroctanoic acid, providing antimicrobial synergy. In an aspect, the synergy of a mixed peracid system allows the use of lower dosages of the peracids.

In another embodiment, a tertiary peracid mixture composition, such as peroxysulfonated oleic acid, peroxyformic acid and peroctanoic acid are used to treat a water source, such as disclosed in U.S. Patent Publication No. 2010/00021557 which is incorporated herein by reference in its entirety. A combination of the three peracids provides significant antimicrobial synergy providing an efficient antimicrobial composition for the water treatment methods according to the invention. In addition, it is thought the high acidity built in the composition assists in removing chemical contaminants from the water (e.g. sulfite and sulfide species).

Advantageously, a combination of peroxycarboxylic acids provides a composition with desirable antimicrobial activity in the presence of high organic soil loads. The mixed peroxycarboxylic acid compositions often provide synergistic micro efficacy.

Accordingly, compositions of the invention can include a peroxycarboxylic acid, or mixtures thereof.

Various commercial formulations of peracids are available, including for example, peracetic acid (15%) available from Ecolab Inc., St. Paul Minn. Most commercial peracid solutions state a specific percarboxylic acid concentration without reference to the other chemical components in a use solution. However, it should be understood that commercial products, such as peracetic acid, will also contain the corresponding carboxylic acid (e.g. acetic acid), hydrogen peroxide and water.

Any suitable $C_1$-$C_{22}$ percarboxylic acid can be used in the present compositions. In some embodiments, the $C_1$-$C_{22}$ percarboxylic acid is a $C_2$-$C_{20}$ percarboxylic acid. In other embodiments, the $C_1$-$C_{22}$ percarboxylic is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ carboxylic acid. In still other embodiments, the $C_1$-$C_{22}$ percarboxylic acid comprises peroxyformic acid, peroxyacetic acid, peroxyoctanoic acid and/or peroxysulfonated oleic acid.

The $C_1$-$C_{22}$ percarboxylic acid can be used at any suitable concentration. In some embodiments, the $C_1$-$C_{22}$ percarboxylic acid has a concentration from about 1 wt-% to about 40 wt-%. In other embodiments, the $C_1$-$C_{22}$ percarboxylic acid has a concentration from about 1 wt-% to about 20 wt-%. In still other embodiments, the $C_1$-$C_{22}$ percarboxylic acid has a concentration at about 1 wt-%, 2 wt-%, 3 wt-%, 4 wt-%, 5 wt-%, 6 wt-%, 7 wt-%, 8 wt-%, 9 wt-%, 10 wt-%, 11 wt-%, 12 wt-%, 13 wt-%, 14 wt-%, 15 wt-%, 16 wt-%, 17 wt-%, 18 wt-%, 19 wt-%, 20 wt-%, 25 wt-%, 30 wt-%, 35 wt-%, or 40 wt-%. In yet other embodiments, the $C_1$-$C_{22}$ percarboxylic acid has a concentration from about 0.1 ppm to about 10,000 ppm, e.g., about 0.1-1 ppm, 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm, 1,000-1,500 ppm, 1,500-2,000 ppm, 2,000-2,500 ppm, 2,500-3,000 ppm, 3,000-3,500 ppm, 3,500-4,000 ppm, 4,000-4,500 ppm, or 4,500-5,000 ppm, 5,000-5,500 ppm. 5,500-6,000 ppm, 6,000-6,500 ppm, 6,500-7,000 ppm, 7,000-7,500 ppm, 7,500-8,000, 8,000-8,500 ppm, 8,500-9,000 ppm, 9,000-9,500 ppm, or 9,500-10,000 ppm.

Additional Optional Materials

The present compositions can optionally include additional ingredients to enhance the composition for water treatment according to the invention, including for example, friction reducers, viscosity enhancers and the like. Additional optional functional ingredients may include for example, peracid stabilizers, emulsifiers, corrosion inhibitors and/or descaling agents (i.e. scale inhibitors), surfactants and/or additional antimicrobial agents for enhanced efficacy (e.g. mixed peracids, biocides), antifoaming agents, acidulants (e.g. strong mineral acids), additional carboxylic acids, surfactants, anti-redeposition agents, builders, and the like. In an embodiment, no additional functional ingredients are employed.

Anti-Redeposition Agents

The present compositions or cleaning use solutions can include an anti-redeposition agent capable of facilitating sustained suspension of soils in a cleaning solution and preventing the removed soils from being redeposited onto the substrate being cleaned. Examples of suitable anti-redeposition agents include fatty acid amides, fluorocarbon surfactants, complex phosphate esters, styrene maleic anhydride copolymers, and cellulosic derivatives such as hydroxyethyl cellulose, hydroxypropyl cellulose, and the like. A use solution can include 0.005-10 wt %, or 0.1-5 wt %, of an anti-redeposition agent.

Builders

The present compositions or cleaning use solutions can include a builder. Builders include chelating agents (chelators), sequestering agents (sequestrants), and the like. The builder may act to stabilize the cleaning composition or use solution. Examples of builders include, but are not limited to, phosphonates, phosphates, aminocarboxylates and their derivatives, pyrophosphates, polyphosphates, ethylenediamene and ethylenetriamene derivatives, hydroxyacids, and mono-, di-, and tri-carboxylates and their corresponding acids. Other exemplary builders include aluminosilicates, nitroloacetates and their derivatives, and mixtures thereof. Still other exemplary builders include aminocarboxylates, including salts of ethylenediaminetetraacetic acid (EDTA), hydroxyethylenediaminetetraacetic acid (HEDTA), and diethylenetriaminepentaacetic acid. For a further discussion of chelating agents/sequestrants, see Kirk-Othmer, Encyclopedia of Chemical Technology, Third Edition, volume 5, pages 339-366 and volume 23, pages 319-320, which is incorporated in its entirety. According to an aspect of the invention, preferred builders are water soluble, biodegradable and phosphorus-free. The amount of builder in the cleaning composition or use solution, if present, is typically between about 10 ppm and about 1000 ppm in the cleaning composition or use solution.

Friction Reducers

Friction reducers are used in water or other water-based fluids used in hydraulic fracturing treatments for subterranean well formations in order to improve permeability of the desired gas and/or oil being recovered from the fluid-conductive cracks or pathways created through the fracking process. The friction reducers allow the water to be pumped into the formations more quickly. Various polymer additives have been widely used as friction reducers to enhance or modify the characteristics of the aqueous fluids used in well drilling, recovery and production applications.

Examples of commonly used friction reducers include polyacrylamide polymers and copolymers. In an aspect, additional suitable friction reducers may include acrylamide-derived polymers and copolymers, such as polyacrylamide (sometime abbreviated as PAM), acrylamide-acrylate (acrylic acid) copolymers, acrylic acid-methacrylamide copolymers, partially hydrolyzed polyacrylamide copolymers (PHPA), partially hydrolyzed polymethacrylamide, acrylamide-methyl-propane sulfonate copolymers (AMPS) and the like. Various derivatives of such polymers and copolymers, e.g., quaternary amine salts, hydrolyzed versions, and the like, should be understood to be included with the polymers and copolymers described herein.

Friction reducers are combined with water and/or other aqueous fluids, which in combination are often referred to as "slick water" fluids. Slick water fluids have reduced frictional drag and beneficial flow characteristics which enable the pumping of the aqueous fluids into various gas- and/or oil-producing areas, including for example for fracturing.

In an aspect of the invention, a friction reducer is present in a use solution in an amount between about 1 ppm to about 1,000 ppm, or from about 100 ppm to 1,000 ppm.

In a further aspect, a friction reducer is present in a use solution in an amount of at least about 0.01 wt-% to about 10 wt-%, preferably at least about 0.01 wt-% to about 5 wt-%, preferably at least about 0.01 wt-% to about 1 wt-%, more preferably at least about 0.01 wt-% to about 0.5 wt-%, and still more preferably at least about 0.01 wt-% to about 0.1 wt-%.

Beneficially, the compositions and methods of the invention do not negatively interfere with friction reducers included in an aqueous solution.

Viscosity Enhancers

Viscosity enhancers are additional polymers used in water or other water-based fluids used in hydraulic fracturing treatments to provide viscosity enhancement. Natural and/or synthetic viscosity-increasing polymers may be employed in compositions and methods according to the invention. Viscosity enhancers may also be referred to as gelling agents and examples include guar, xanthan, cellulose derivatives and polyacrylamide and polyacrylate polymers and copolymers, and the like.

In an aspect of the invention, a viscosity enhancer is present in a use solution in an amount between about 1 ppm to about 1,000 ppm, or from about 100 ppm to 1,000 ppm. In a further aspect, a viscosity enhancer is present in a use solution in an amount of at least about 0.01 wt-% to about 10 wt-%, preferably at least about 0.01 wt-% to about 5 wt-%, preferably at least about 0.01 wt-% to about 1 wt-%. at least about 0.01 wt-% to about 2 wt-%, preferably at least about 0.01 wt-% to about 1 wt-%, preferably at least about 0.01 wt-% to about 0.5 wt-%. Beneficially, the compositions and methods of the invention do not negatively interfere with viscosity enhancer included in an aqueous solution.

Corrosion Inhibitors

Corrosion inhibitors are additional molecules used in oil and gas recovery operations. Corrosion inhibitors that may be employed in the present disclosure include the exemplary corrosion inhibitors disclosed in U.S. Pat. Nos. 3,909,447, 4,443,609, 5,965,785 and 9,150,793, GB Pat. No. 1,198,734, WO/03/006581, WO04/044266, and WO08/005058, each incorporated herein by reference in their entireties.

In some embodiments, the corrosion inhibitor can be a phosphate ester, a derivative of the phosphate ester, a diacid, a derivative of the diacid, a quat amine, a derivative of the quat amine, an imidazoline, a derivative of the imidazoline, an alkyl pyridine, a derivative of the alkyl pyridine, a phosphonium salt, a derivative of the phosphonium salt, or a combination thereof.

In an embodiment, the corrosion inhibitors include neutralizing amines. Suitable neutralization amines include morpholine, methoxypropylamine, ethyienediamine, monoethanolalmine, dimethylethanolamine diethylhydroxylamine, and hydrazine didrates.

In an embodiment, the corrosion inhibitors include cationic surfactant comprising an ammonium halide. The ammonium halide may include any suitable types of ammonium halides. In embodiments, the ammonium halides include alkyl ammonium halides, polyalkyl ammonium halides, benzyl triethyl ammonium halides or any combinations thereof. In embodiments, the cationic surfactant includes any combination or at least one of an alkyl trimethyl ammonium halide, alkyl triethyl ammonium halide, an alkyl dimethyl benzyl ammonium halide, and one or more imidazolinium halides.

In an embodiment, the corrosion inhibitors include phosphonates, including phosphonic acid and esters, such as tetrahydrothiazoles phosphonic acids or esters. Additional phosphorus-based compounds may be suitable for use, including thiophosphonic acid and the salts and alkyl, and aryl esters of the same.

In an aspect of the invention, a corrosion inhibitor is present in a use solution in an amount between about 1 ppm to 50,000 ppm. In a further aspect, a corrosion inhibitor is present in a use solution in an amount of at least about 0.0001 wt-% to about 20 wt-%, preferably at least about 0.0001 wt-% to about 10 wt-%, preferably at least about 0.0001 wt-% to about 5 wt-%, preferably at least about 0.0001 wt-% to about 1 wt-%, preferably at least about 0.0001 wt-% to about 0.1 wt-%, and still more preferably at least about 0.0001 wt-% to about 0.05 wt-%.

Beneficially, the compositions and methods of the invention do not negatively interfere with corrosion inhibitor included in an aqueous solution. As a further benefit, the use of the two-part peroxycarboxylic acid forming compositions according to the invention allow formulation of the corrosion inhibitors directly into either of the premix formulations, overcoming a substantial limitation of the prior art wherein conventional corrosion inhibitors are not sufficiently stable in other equilibrium chemistries. The two-part premixes according to embodiments of the invention allow formulation of the corrosion inhibitors directly into a premix and thereby reducing the number of inputs required for a system to be treated according to the methods and chemistries of the present invention.

Scale Inhibitors

Scale inhibitors are additional molecules used in oil and gas recovery operations. Common scale inhibitors that may be employed in these types of applications include polymers and co-polymers, phosphates, phosphate esters and the like.

In an aspect of the invention, a scale inhibitor is present in a use solution in an amount between about 1 ppm to about 5,000 ppm, or from about 100 ppm to 5,000 ppm. In a further aspect, a scale inhibitor is present in a use solution in an amount of at least about 0.0001 wt-% to about 10 wt-%, at least about 0.0001 wt-% to about 1 wt-%, preferably at least about 0.0001 wt-% to about 0.1 wt-%, preferably at least about 0.0001 wt-% to about 0.05 wt-%. Beneficially, the compositions and methods of the invention do not negatively interfere with scale inhibitor included in an aqueous solution.

Additional Antimicrobial Agents

Additional antimicrobial agents may be included in the compositions and/or methods of the invention for enhanced antimicrobial efficacy. In addition to the use of peracid compositions, additional antimicrobial agents and biocides may be employed. Additional biocides may include, for example, a quaternary ammonium compound as disclosed in U.S. Pat. No. 6,627,657, which is incorporated herein by reference in its entirety. Beneficially, the presence of the quaternary ammonium compound provides both synergistic antimicrobial efficacies with peracids, as well as maintains long term biocidal efficacy of the compositions.

In another embodiment, the additional biocide may include an oxidizer compatible phosphonium biocide, such as tributyl tetradecyl phosphonium chloride. The phosphonium biocide provides similar antimicrobial advantages as the quaternary ammonium compound in combination with the peracids. In addition, the phosphonium biocide is compatible with the anionic polymeric chemicals commonly used in the oil field applications, such as the methods of the fracking disclosed according to the invention.

Additional antimicrobial and biocide agents may be employed in amounts sufficient to provide antimicrobial efficacy, as may vary depending upon the water source in need of treatment and the contaminants therein. Such agents may be present in a use solution in an amount of at least about 0.1 wt-% to about 5 wt-%, preferably at least about 0.1 wt-% to about 2 wt-%, more preferably from about 0.1 wt-% to about 1 wt-%.

Acidulants

Acidulants may be included as additional functional ingredients in a composition according to the invention. In an aspect, a strong mineral acid such as nitric acid or sulfuric acid can be used to treat water sources, as disclosed in U.S. Pat. No. 4,587,264, which is incorporated herein by reference in its entirety. The combined use of a strong mineral acid with the peracid composition provides enhanced antimicrobial efficacy as a result of the acidity assisting in removing chemical contaminants within the water source (e.g. sulfite and sulfide species). In addition, some strong mineral acids, such as nitric acid, provide a further benefit of reducing the risk of corrosion toward metals contacted by the peracid compositions according to the invention. In some embodiments, the present composition does not comprise a mineral acid or a strong mineral acid.

Acidulants may be employed in amounts sufficient to provide the intended antimicrobial efficacy and/or anticorrosion benefits, as may vary depending upon the water source in need of treatment and the contaminants therein. Such agents may be present in a use solution in an amount of at least about 0.1 wt-% to about 10 wt-%, preferably at least about 0.1 wt-% to about 5 wt-%, more preferably from about 0.1 wt-% to about 1 wt-%.

Catalase and Peroxidase Enzyme

In an aspect of the invention, a catalase or peroxidase enzyme can be used to reduce and/or eliminate the concentration of hydrogen peroxide in an antimicrobial peracid composition. The enzymes catalyze the decomposition of hydrogen peroxide to water and oxygen. Beneficially, the reduction and/or elimination of hydrogen peroxide (strong oxidizer) results in other additives for a water treatment source (e.g. water source) not being degraded or rendered incompatible. Various additives used to enhance or modify the characteristics of the aqueous fluids used in well drilling, recovery and production applications are at risk of degradation by the oxidizing effects of hydrogen peroxide. These may include for example, friction reducers and viscosity enhancers used in commercial well drilling, well completion and stimulation, or production applications.

Various sources of catalase enzymes may be employed according to the invention, including: animal sources such as bovine catalase isolated from beef livers; fungal catalases isolated from fungi including *Penicllium chrysogenum, Penicilbum notatum*, and *Aspergillus niger*; plant sources; bacterial sources such as *Staphylcoccus aureus*, and genetic variations and modifications thereof. In an aspect of the invention, fungal catalases are utilized to reduce the hydrogen peroxide content of a peracid composition. Catalases are commercially available in various forms, including liquid and spray dried forms. Commercially available catalase includes both the active enzyme as well as additional ingredients to enhance the stability of the enzyme. Some exemplary commercially available catalase enzymes include Genencor CA-100 and CA-400, as well as Mitsubishi Gas and Chemical (MGC) ASC super G and ASC super 200, and Optimase CA 400L from Genecor International. Additional description of suitable catalase enzymes are disclosed and herein incorporated by reference in its entirety from U.S. Patent Publication No. 2009/0269324.

In an aspect of the invention, catalase enzymes have a high ability to decompose hydrogen peroxide. Beneficially, the reduction or elimination of hydrogen peroxide from oxidizing compositions obviates the various detriments caused by oxidizing agents. In particular, the use of catalase with the peracids compositions provides enhanced antimicrobial benefits without causing the damage associated with conventional oxidizing agents (e.g. peracetic acid, hypochlorite or hypochlorous acid, and/or chlorine dioxide), such as corrosion.

Peroxidase enzymes may also be employed to decompose hydrogen peroxide from a peracid composition. Although peroxidase enzymes primarily function to enable oxidation of substrates by hydrogen peroxide, they are also suitable for effectively lowering hydrogen peroxide to peracid ratios in compositions. Various sources of peroxidase enzymes may be employed according to the invention, including for example animal sources, fungal peroxidases, and genetic variations and modifications thereof. Peroxidases are commercially available in various forms, including liquid and spray dried forms. Commercially available peroxidases include both the active enzyme as well as additional ingredients to enhance the stability of the enzyme.

In some embodiments, the catalase or peroxidase enzyme is able to degrade at least about 50% of the initial concentration of hydrogen peroxide in a peracid composition. Preferably, the enzyme is provided in sufficient amount to reduce the hydrogen peroxide concentration of a peracid composition by at least more than about 50%, more preferably at least about 60%, at least about 70%, at least about 80%, at least about 90%. In some embodiments, the enzyme reduces the hydrogen peroxide concentration of a peracid composition by more than 90%.

In an aspect of the invention, the enzymes are suitable for use and have a tolerance to a wide range of temperatures, including the temperatures ranges in water treatment applications which may range from about 0-80° C. A suitable catalase enzyme will maintain at least 50% of its activity under such storage and/or application temperatures for at least about 10 minutes, preferably for at least about 1 hour.

In a further aspect of the invention, the catalase or peroxidase enzymes described herein have a tolerance to pH ranges found in water treatment applications. Acetic acid concentrations (or other carboxylic acid) in a water treatment application can widely range in parts per million (ppm) of acetic or other carboxylic acid. The solutions may have a corresponding range of pH range from greater than 0 to about 10. A suitable catalase or peroxidase enzyme will maintain at least about 50% of its activity in such solutions of acetic or other carboxylic acid over a period of about 10 minutes.

In an aspect of the invention, a catalase or peroxidase enzyme is present in a use solution of the water treatment and peracid composition in sufficient amounts to reduce the concentration of hydrogen peroxide from the peracid composition by at least 50% within about 10 minutes, preferably within about 5 minutes, preferably within about 2 to 5 minutes, more preferably within about 1 minute. The ranges of concentration of the enzymes will vary depending upon the amount of time within which 50% of the hydrogen peroxide from the peracid composition is removed. In certain aspects of the invention, a catalase or peroxidase enzyme is present in a use solution composition including the water source to be treated in amounts between about 1 ppm and about 1,000 ppm, preferably between about 5 ppm and 500 ppm, and more preferably between about 10 ppm and about 100 ppm.

Surfactants

In some embodiments, the cleaning compositions employed by the method of cleaning include a surfactant. Beneficially, surfactants improve soil removal and can further be used to prevent the buildup of large quantities of foam generated by soils under alkaline conditions. The surfactant chosen can be compatible with the surface to be cleaned. A variety of surfactants can be used, including anionic, nonionic, cationic, and zwitterionic surfactants, which are commercially available from a number of sources. Suitable surfactants include nonionic surfactants, for example, low foaming non-ionic surfactants. For a discussion of surfactants, see Kirk-Othmer, Encyclopedia of Chemical Technology, Third Edition, volume 8, pages 900-912, which is incorporated in its entirety.

Peracids are known to be strong oxidation agents, and as a result many chemicals, including commonly used surfactants are not compatible with concentrated peracids for extended presence of peracids. While it is ideal to use surfactants along with peracids to deliver preferred performance, such as cleaning, wetting et al., there is very limited choice of surfactants that could be put in preformed peracid formulations that meet the minimum shelf life requirements for commercial use. For examples, nonionic surfactants will be degraded by peracids, and cationic surfactants with halogen counter anions will decompose peracids. Some anionic surfactants, namely non substituted alkyl sulfonates, such as linear alkylbenzensulfonate, liner alkylsulfonate are more compatible with peracids and may be used in some peracids compositions, but these anionic surfactants may not deliver the desired performance owing to their unwanted properties, such as high foam, water hardness tolerance as well as regulation requirements. In contrast, for onsite generated peracid compositions such as disclosed in the present art, all surfactants described above could be coexist with the peracids, as the generated peracids are only stored for very limited time, and typically in hours at the most, and the reactions between the surfactants and the peracids are not significant.

In particular embodiments of the invention, the method of cleaning is directed to brewery surfaces. The soils encountered in brewery surfaces already contain components that are moderate to high foaming. Thus, in such an application, it may be desirous to use a low foaming surfactant or wetting agent to provide wetting properties and better cleaning effectiveness. Examples of various suitable surfactants for such brewery applications include those disclosed in U.S. Patent Publication 2014/0261546, which is herein incorporated by reference in its entirety.

Nonionic surfactants suitable for use in the methods of the present invention include, but are not limited to, those having a polyalkylene oxide polymer as a portion of the surfactant molecule. Exemplary nonionic surfactants include, but are not limited to, chlorine-, benzyl-, methyl-, ethyl-, propyl-, butyl- and other like alkyl-capped polyethylene and/or polypropylene glycol ethers of fatty alcohols; polyalkylene oxide free nonionics such as alkyl polyglycosides; sorbitan and sucrose esters and their ethoxylates; alkoxylated ethylene diamine; carboxylic acid esters such as glycerol esters, polyoxyethylene esters, ethoxylated and glycol esters of fatty acids; carboxylic amides such as diethanolamine condensates, monoalkanolamine condensates, polyoxyethylene fatty acid amides; and ethoxylated amines and ether amines commercially available from Tomah Corporation and other like nonionic compounds. In some embodiments sugar ester based nonionic surfactants are preferred, including for example sorbitan and sucrose esters, such as those commercially available as Polysorbate 60, Polysorbate 80, sorbitan octanoate, and the like. In other embodiments, polyglycerol fatty acid ester surfactants are preferred.

Additional exemplary nonionic surfactants suitable for use in the methods of the present invention, include, but are not limited to, those having a polyalkylene oxide polymer portion include nonionic surfactants of C6-C24 alcohol ethoxylates (e.g., C6-C14 alcohol ethoxylates) having 1 to about 20 ethylene oxide groups (e.g., about 9 to about 20 ethylene oxide groups); C6-C24 alkylphenol ethoxylates (e.g., C8-C.sub.10 alkylphenol ethoxylates) having 1 to about 100 ethylene oxide groups (e.g., about 12 to about 20 ethylene oxide groups); C6-C24 alkylpolyglycosides (e.g., C6-C20 alkylpolyglycosides) having 1 to about 20 glycoside groups (e.g., about 9 to about 20 glycoside groups); C6-C24 fatty acid ester ethoxylates, propoxylates or glycerides; and C4-C24 mono or dialkanolamides. In some embodiments ethoxylated mono and diglyceride nonionic surfactants are preferred.

Suitable surfactants may also include food grade surfactants, linear alkylbenzene sulfonic acids and their salts, and ethylene oxide/propylene oxide derivatives sold under the Pluronic trade name. Suitable surfactants include those that are compatible as an indirect or direct food additive or substance.

Anionic surfactants suitable for use with the disclosed methods may also include, for example, carboxylates such as alkylcarboxylates (carboxylic acid salts) and polyalkoxycarboxylates, alcohol ethoxylate carboxylates, nonylphenol ethoxylate carboxylates, and the like; sulfonates such as alkylsulfonates, alkylbenzenesulfonates, alkylarylsulfonates, sulfonated fatty acid esters, and the like; sulfates such as sulfated alcohols, sulfated alcohol ethoxylates, sulfated alkylphenols, alkylsulfates, sulfosuccinates, alkylether sulfates, and the like; and phosphate esters such as alkylphosphate esters, and the like. Exemplary anionics include, but are not limited to, sodium alkylarylsulfonate, alpha-olefin sulfonate, and fatty alcohol sulfates. Examples of suitable anionic surfactants include sodium dodecylbenzene sulfonic acid, potassium laureth-7 sulfate, and sodium tetradecenyl sulfonate.

In some embodiments, the surfactant includes linear alkyl benzene sulfonates, alcohol sulfonates, amine oxides, linear and branched alcohol ethoxylates, alkyl polyglucosides, alkyl phenol ethoxylates, polyethylene glycol esters, EO/PO block copolymers and combinations thereof. In other embodiments, alkyl linear benzene sulfonate anionic surfactants are preferred.

The surfactants described herein can be used singly or in combination in the methods of the present invention. In particular, the nonionics and anionics can be used in combination. The semi-polar nonionic, cationic, amphoteric and zwitterionic surfactants can be employed in combination with nonionics or anionics. The above examples are merely specific illustrations of the numerous surfactants which can find application within the scope of this invention. It should be understood that the selection of particular surfactants or combinations of surfactants can be based on a number of factors including compatibility with the surface to be cleaned at the intended use concentration and the intended environmental conditions including temperature and pH.

In addition, the level and degree of foaming under the conditions of use and in subsequent recovery of the composition can be a factor for selecting particular surfactants and mixtures of surfactants. For example, in certain applications it may be desirable to minimize foaming and a surfactant or mixture of surfactants that provides reduced foaming can be used. In addition, it may be desirable to select a surfactant or a mixture of surfactants that exhibits a foam that breaks down relatively quickly so that the composition can be recovered and reused with an acceptable amount of down time. In addition, the surfactant or mixture of surfactants can be selected depending upon the particular soil that is to be removed.

It should be understood that the compositions for use with the methods of the present invention need not include a surfactant or a surfactant mixture, and can include other components. In addition, the compositions can include a surfactant or surfactant mixture in combination with other components. In some embodiments, the cleaning compositions and use solutions employed by the method of cleaning include about 0.005 wt. % to about 5 wt. % of a surfactant. In particular embodiments of the present invention, the surfactant comprises between about 0.005 wt. % to about 0.02 wt. % of the cleaning composition or use solution. In another aspect of the invention, the surfactant comprises between about 0.5 wt. % and about 1.0 wt. % of the cleaning composition or use solution. In some embodiments, the compositions of the present invention include about 50 ppm to about 200 ppm of a surfactant.

In some embodiments, the amount of surfactant in the cleaning composition is about 0.0001 wt % to about 1.0 wt %. Acceptable levels of surfactant include about 0.001 wt % to about 1 wt %, or about 0.002 wt % to about 0.05 wt %. It is to be understood that all values and ranges between these values and ranges are encompassed by the methods of the present invention.

Methods for Treating a Target

In still another aspect, the present invention is directed to a method for treating a target, which method comprises contacting a target with an effective amount of peroxyformic acid formed using the above methods to form a treated target composition, wherein said treated target composition comprises from about 0.1 ppm to about 10,000 ppm of said peroxyformic acid, and preferably, said contacting lasts for sufficient time to stabilize or reduce microbial population in and/or on said target or said treated target composition.

The peroxyformic acid and the target can be contacted to form a treated target composition comprising any suitable concentration of said peroxyformic acid, e.g., about 0.1-10,000 ppm or any range therein, or preferably from about 0.5-5,000 ppm, including about 0.1-1 ppm, 0.5-1 ppm, 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm, 1,000-1,500 ppm, 1,500-2,000 ppm, 2,000-2,500 ppm, 2,500-3,000 ppm, 3,000-3,500 ppm, 3,500-4,000 ppm, 4,000-4,500 ppm, or 4,500-5,000 ppm, 5,000-5,500 ppm, 5,500-6,000 ppm, 6,000-6,500 ppm, 6,500-7,000 ppm, 7,000-7,500 ppm, 7,500-8,000, 8,000-8,500 ppm, 8,500-9,000 ppm, 9,000-9,500 ppm, or 9,500-10,000 ppm of peroxyformic acid.

The composition used in the present methods can retain any suitable concentration or percentage of the peroxyformic acid activity for any suitable time after the treated target composition is formed. In some embodiments, the composition used in the present methods retains at least about 50%, 55%, 60%, 65%, 70%, 75%, 80%, 85% or 90% of the initial peroxyformic acid activity for any suitable time after the treated target composition is formed. In other embodiments, the composition used in the present methods retains at least about 60% of the initial peroxyformic acid activity for at least 1, 2, 3, 4, 5, 6, 7, 8, 9, 10, 11, 12, 13, 14, 15, 20, 25, 30 minutes, 1, 2, 5, 10, 15, 20 or 24 hours, or longer after the treated target composition is formed.

The present methods can be used to treat any suitable target. In some embodiments, the target is water, and the present methods can comprise providing an effective amount of peroxyformic acid formed using the above methods to a water source in need of treatment to form a treated water source, wherein said treated water source comprises from about 0.5 ppm to about 5,000 ppm of said peroxyformic acid, e.g., about 0.1-1,000 ppm or any range therein, or about 0.5-5,000 ppm or any range therein, including about 0.5-10 ppm, 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm, or 1,000-5,000 ppm of peroxyformic acid.

The present methods can be used to treat any suitable water source. For example, a water source in need of treatment can be fresh water, pond water, sea water, produced water, paper manufacturing water, tower water or a combination thereof.

In some embodiments, the tower water is cooling water and the treated water source comprises from about 0.1 ppm to about 10 ppm of the peroxyformic acid, e.g., about 1-10 ppm or any range therein, including about 0.1-1 ppm, 1-2 ppm, 2-3 ppm, 3-4 ppm, 4-5 ppm, 5-6 ppm, 6-7 ppm, 7-8 ppm, 8-9 ppm, or 9-10 ppm peroxyformic acid. The contacting step can last any suitable amount of time, e.g., about 1-2 minutes, 2-3 minutes, 3-4 minutes, 4-5 minutes, 5-6 minutes, 6-7 minutes, 7-8 minutes, 8-9 minutes, or 9-10 minutes. The contacting step can be conducted at suitable temperature range. For example, the contacting step can be conducted at a temperature ranging from about −2° C. to about 70° C., e.g., about −2° C.-0° C., −1° C.-0° C., 0° C.-1° C., 1° C.-2° C., 2° C.-3° C., 3° C.-4° C., 4° C.-5° C., 5° C.-10° C., 10° C.-15° C., 15° C.-20° C., 20° C.-25° C., 25° C.-30° C., 30° C.-35° C., 35° C.-40° C., 40° C.-45° C., 45° C.-50° C., 50° C.-55° C., 55° C.-60° C., 60-65° C., or 65° C.-70° C.

In some embodiments, the present methods can be used to treat a water source used in oil and/or gas drilling operation. For example, the present methods can be used to treat a water source used in an operation of induced hydraulic fracturing (hydrofracturing or fracking). The water source can comprise a friction reducer or a viscosity enhancer. The present methods can be used to treat a water source to form a treated water source that comprises from about 0.1 ppm to about 10 ppm of the peroxyformic acid, e.g., about 1-10 ppm or any range therein, including about 1-2 ppm, 2-3 ppm, 3-4 ppm, 4-5 ppm, 5-6 ppm, 6-7 ppm, 7-8 ppm, 8-9 ppm, or 9-10 ppm peroxyformic acid. The present methods can further comprise disposing of the treated water source. The present methods can further comprise directing the treated water source into a subterranean environment, e.g., a subterranean environment that comprises a well in a gas and/or oil.

In some embodiments, the target to be treated by the present methods can be water and/or at least a portion of a medium, a container, an equipment, a system or a facility for producing, holding, processing, packaging, storing, or transporting pulp. The present methods can be used to treat water and/or other target(s) for any suitable purpose. For example, the present methods can be used in papermaking, textiles, food, or pharmaceutical industry. The present methods can be used to treat a water source, alone or in combination with other target(s), to form a treated water source that comprises any suitable concentration of peroxyformic acid, e.g., about 0.5-30 ppm or any range therein, including about 1-2 ppm, 2-3 ppm, 3-4 ppm, 4-5 ppm, 5-6 ppm, 6-7 ppm, 7-8 ppm, 8-9 ppm, 9-10 ppm, 10-15 ppm, 15-20 ppm, 20-25 ppm, or 25-30 ppm of peroxyformic acid.

In some embodiments, the present methods can be used to reduce or remove $H_2S$ in a treated water source. The present methods can be used to reduce or remove $H_2S$ at any suitable rate. For example, $H_2S$ can be reduced or removed at a rate similar to that as achieved by using a comparable amount of triazine. The present methods can be used to reduce or remove $H_2S$ in any suitable treated water source. For example, the treated water source can be a treated produced water. The peroxyformic acid can be used at any suitable concentration, e.g., about 0.1-1,000 ppm or any range therein, including about 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm of peroxyformic acid.

In some embodiments, the present methods can be used to reduce or remove iron sulfide in a treated water source. The present methods can be used to reduce or remove iron sulfide in a treated water source at any suitable rate or within any suitable time. For example, the iron sulfide can be reduced or removed within about one hour of the treatment. The present methods can be used to reduce or remove iron sulfide in any suitable treated water source. For example, the treated water source is a treated produced water. The peroxyformic acid can be used at any suitable concentration, e.g., about 0.1-1,000 ppm or any range therein, including about 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm of peroxyformic acid.

In some embodiments, the present methods can be used to improve clarity of a treated water source. The present methods can be used to improve clarity of a treated water source in any suitable manner. For example, the present methods can be used to improve clarity of a treated water source by oxidizing a contaminant in the treated water source. The present methods can be used to improve clarity of any suitable water source. For example, the treated water source can be a treated produced water. The peroxyformic acid can be used at any suitable concentration, e.g., about 0.5-1,000 ppm or any range therein, including about 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm of peroxyformic acid.

In some embodiments, the present methods can be used to reduce the total dissolved oxygen in a water source. The present methods can be used to reduce the total dissolved oxygen in any suitable treated water source. For example, the treated water source can be a treated produced water. The peroxyformic acid can be used at any suitable concentration. For example, the peroxyformic acid can be used at a concentration that is at or above its consumption rate in the treated water source. In another example, the peroxyformic acid can be used at a concentration from about 0.1 ppm to about 1,000 ppm, e.g., about 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm of peroxyformic acid.

In some embodiments, a water source can be treated with the peroxyformic acid so that the treated water source has a lower corrosion rate compared to a water source treated with a $C_2$-$C_{22}$ percarboxylic acid. For example, a water source can be treated with the peroxyformic acid at a concentration at its consumption rate, the treated water source can have a lower corrosion rate compared to a water source treated with a $C_2$-$C_{22}$ percarboxylic acid at a concentration at its consumption rate. Any suitable water source can be treated with the peroxyformic acid so that the treated water source has a lower corrosion rate compared to a water source treated with a $C_2$-$C_{22}$ percarboxylic acid. For example, the treated water source can be a treated produced water. The peroxyformic acid can be used at any suitable concentration, e.g., about 0.1-1,000 ppm or any range therein, including about 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm of peroxyformic acid.

The present methods can further comprise contacting the target with a corrosion inhibitor. Any suitable corrosion inhibitor can be used. In some embodiments, the corrosion inhibitor can be a phosphate ester, a derivative of the phosphate ester, a diacid, a derivative of the diacid, a quat amine, a derivative of the quat amine, an imidazoline, a derivative of the imidazoline, an alkyl pyridine, a derivative of the alkyl pyridine, a phosphonium salt, a derivative of the phosphonium salt, or a combination thereof.

The corrosion inhibitor can be used at any suitable concentration. In some embodiments, the corrosion inhibitor can be used at a concentration from about 0.5 ppm to about 50,000 ppm, e.g., about 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm, 1,000-1,500 ppm, 1,500-2,000 ppm, 2,000-2,500 ppm, 2,500-3,000 ppm, 3,000-3,500 ppm, 3,500-4,000 ppm, 4,000-4,500 ppm, or 4,500-5,000 ppm, 5,000-5,500 ppm, 5,500-6,000 ppm, 6,000-6,500 ppm, 6,500-7,000 ppm, 7,000-7,500 ppm, 7,500-8,000, 8,000-8,500 ppm, 8,500-9,000 ppm, 9,000-9,500 ppm, 9,500-10,000, or 10,000-50,000 ppm. In other embodiments, the ratio between the concentration of the peroxyformic acid (w/v) and the concentration of the corrosion inhibitor (w/v) used in the present method can be from about 0.01 to about 100, e.g., about 0.01-0.05, 0.05-0.1, 0.1-0.5, 0.5-1, 1-2, 2-3, 3-4, 4-5, 5-6, 6-7, 7-8, 8-9, 9-10, 10-15, 15-20, 20-25, 25-30, 30-35, 35-40, 40-45, 45-50, 50-60, 60-70, 70-80, 80-90, 90-100. In still other embodiments, the corrosion inhibitor can be used at a concentration that has a synergistic effect with the peroxyformic acid to stabilize or reduce microbial population in and/or on the target or the treated target composition. In yet other embodiments, the corrosion inhibitor can be used at a concentration that reduces acid corrosion in and/or on the target or the treated target composition. In yet other embodiments, the corrosion inhibitor can be used at a concentration that has a synergistic effect with the peroxyformic acid to stabilize or reduce microbial population in and/or on the target or the treated target composition and reduces acid corrosion in and/or on the target or the treated target composition.

The target can be contacted with the corrosion inhibitor at any suitable time. In some embodiments, the target can be contacted with the corrosion inhibitor before the target is contacted with the peroxyformic acid. In other embodiments, the target can be contacted with the corrosion inhibitor after the target is contacted with the peroxyformic acid. In still other embodiments, the target can be contacted with the corrosion inhibitor concurrently when the target is contacted with the peroxyformic acid, e.g., the corrosion inhibitor can be comprised in the peroxyformic acid composition formed by the methods described above.

In some embodiments, the target to be treated by the present methods can be a food item or a plant item and/or at least a portion of a medium, a container, an equipment, a system or a facility for growing, holding, processing, packaging, storing, transporting, preparing, cooking or serving the food item or the plant item. Any suitable concentration of peroxyformic acid can be used in the present methods. For example, the peroxyformic acid can be used at a concentration from about 0.1 ppm to about 100 ppm, e.g., about 1-2 ppm, 2-3 ppm, 3-4 ppm, 4-5 ppm, 5-6 ppm, 6-7 ppm, 7-8 ppm, 8-9 ppm, 9-10 ppm, 10-15 ppm, 15-20 ppm, 20-25 ppm, or 25-30 ppm, 30-40 ppm, 40-50 ppm, 50-60 ppm, 60-70 ppm, 70-80 ppm, 80-90 ppm, 90-100 ppm of peroxyformic acid. In some embodiments, the target is a food item or a plant item and the contacting step minimizes or does not induce an organoleptic effect in and/or on the food item or a plant item.

The present methods can be used for treating any suitable plant item. In some embodiments, the plant item is a grain, fruit, vegetable or flower plant item. In other embodiments, the plant item is a living plant item or a harvested plant item. In still other embodiments, the plant item comprises a seed, a tuber, a growing plant, a cutting, or a root stock. In yet other embodiments, the present methods are used for treating a living plant tissue comprising treating the plant tissue with the above composition in a diluted concentration to stabilize or reduce microbial population in and/or on the plant tissue. In yet other embodiments, the present methods are used for growing a plant on a hydroponic substrate in a hydroponic liquid supply medium, comprising: (a) establishing a growing and living plant tissue in the hydroponic substrate; (b) contacting the living plant tissue, the hydroponic substrate and the hydroponic liquid with a composition of the present invention to stabilize or reduce microbial population in and/or on the living plant tissue; and (c) harvesting a usable plant product with reduced microbial contamination.

The present methods can be used for treating any suitable food item. For example, the food item can be an animal product, e.g., an animal carcass or an egg, a fruit item, a vegetable item, or a grain item. In some embodiments, the animal carcass can be a beef, pork, veal, buffalo, lamb, fish, sea food or poultry carcass. In other embodiments, the sea food carcass can be scallop, shrimp, crab, octopus, mussel, squid or lobster. In still other embodiments, the fruit item can be a botanic fruit, a culinary fruit, a simple fruit, an aggregate fruit, a multiple fruit, a berry, an accessory fruit or a seedless fruit. In yet other embodiments, the vegetable item can be a flower bud, a seed, a leaf, a leaf sheath, a bud, a stem, a stem of leaves, a stem shoot, a tuber, a whole-plant sprout, a root or a bulb. In yet other embodiments, the grain item can be maize, rice, wheat, barley, sorghum, millet, oat, triticale, rye, buckwheat, fonio or quinoa.

In some embodiments, the target to be treated by the present methods can be a medium, a surface, a container, an equipment, or a system in a health care facility, e.g., a physical office or a hospital. Any suitable concentration of peroxyformic acid can be used in the present methods. For example, the peroxyformic acid can be used at a concentration from about 0.1 ppm, 0.5 ppm, or from about 10 ppm to about 300 ppm, e.g., 10-15 ppm, 15-20 ppm, 20-25 ppm, or 25-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, or 250-300 ppm of peroxyformic acid.

The present methods can be used for treating a target that is at least a portion of a container, an equipment, a system or a facility for holding, processing, packaging, storing, transporting, preparing, cooking or serving the food item or the plant item. In some embodiments, the target is at least a portion of a container, an equipment, a system or a facility for holding, processing, packaging, storing, transporting, preparing, cooking or serving a meat item, a fruit item, a vegetable item, or a grain item. In other embodiments, the target is at least a portion of a container, an equipment, a system or a facility for holding, processing, packaging, storing, or transporting an animal carcass. In still other embodiments, the target is at least a portion of a container, an equipment, a system or a facility used in food processing, food service or health care industry. In yet other embodiments, the target is at least a portion of a fixed in-place process facility. An exemplary fixed in-place process facility can comprise a milk line dairy, a continuous brewing system, a pumpable food system or a beverage processing line.

The present methods can be used for treating a target that is at least a portion of a solid surface or liquid media. In some embodiments, the solid surface is an inanimate solid surface. The inanimate solid surface can be contaminated by a biological fluid, e.g., a biological fluid comprising blood, other hazardous body fluid, or a mixture thereof. In other embodiments, the solid surface can be a contaminated surface. An exemplary contaminated surface can comprise the surface of food service wares or equipment, or the surface of a fabric.

In an application of use for treating a surface, such as a fixed in-place process facility (e.g. brewing system), the treatment beneficially removes soils that are difficult to remove, as brewing beer and wine requires the fermentation of sugars derived from starch-based material e.g., malted barley or fruit juice, e.g., grapes. Fermentation uses yeast to turn the sugars in wort or juice to alcohol and carbon dioxide. During fermentation, the wort becomes beer and the juice becomes wine. Once the boiled wort is cooled and placed in a fermenter, yeast and/or bacteria is propagated in the wort and it is left to ferment, which requires a week to months depending on the type of yeast or bacteria and style of the beer or wine. In addition to producing alcohol, fine particulate matter suspended in the wort settles during fermentation. Once fermentation is complete, the yeast also settles, leaving the beer or wine clear, but the fermentation tanks soiled with dead yeast cells, proteins, hop resins, and/or grape skins. In a particular embodiment of the invention, the method of cleaning may be a CIP technique. In another embodiment of the invention, the method of cleaning may be directed at brewery surfaces.

The peroxyformic acid can be applied in any suitable manner. In some embodiments, the peroxyformic acid can be applied to a target by means of a spray, a fog, or a foam, or by dipping all or part of the target in a composition comprising the peroxyformic acid. In some embodiments, the peroxyformic acid composition is applied to the target by means of a spray, a fog, or a foam. In other embodiments, the diluted peroxyformic acid is applied to the target by applying in the form of a thickened or gelled solution. In still other embodiments, all or part of the target is dipped in the peroxyformic acid composition. The target and/or the peroxyformic acid composition can be subject to any suitable movement to help or facilitate the contact between the target and the peroxyformic acid composition. In some embodiments, the peroxyformic acid composition can be agitated. In other embodiments, the peroxyformic acid composition can be sprayed onto a target, e.g., an animal carcass, under suitable pressure and at a suitable temperature. For example, the peroxyformic acid composition can be sprayed onto an animal carcass at a pressure of at least 50 psi at a temperature of up to about 60° C., resulting in a contact time of at least 30 seconds.

The present methods can comprise any suitable, additional steps. In some embodiments, the present methods can comprise a vacuum treatment step. In other embodiments, the present methods can comprise a step of applying an activated light source to the target, e.g., an animal carcass.

The contacting step in the present methods can last for any suitable amount of time. In some embodiments, the contacting step can last for at least about 30 seconds. For example, the contacting step can last for at least about 30, 40, 50 seconds, 1 minute, 1-2 minutes, 2-3 minutes, 3-4 minutes, 4-5 minutes, 5-6 minutes, 6-7 minutes, 7-8 minutes, 8-9 minutes, or 9-10 minutes, 10-15 minutes, 15-20 minutes, 20-25 minutes, 25-30 minutes, 30-40 minutes, 40-50 minutes, 50-60 minutes, 1-2 hours, 2-3 hours, 3-4 hours, 4-5 hours, 5-6 hours, 6-7 hours, 7-8 hours, 8-9 hours, or 9-10 hours, 16 hours, 1 day, 3 days, 1 week, or until degradation or exhaustion of the chemistry. In an aspect, the contacting step is preferably from about 30 seconds to about 4 hours.

The present methods can be used to reduce microbial population in and/or on the target or the treated target composition by any suitable magnitude. In some embodiments, the present methods can be used to reduce microbial population in and/or on the target or the treated target composition by at least one $\log_{10}$, two $\log_{10}$, three $\log_{10}$, four $\log_{10}$, five $\log_{10}$, or more. In other embodiments, the level of a microorganism, if present in and/or on the target or the treated target composition, can be stabilized or reduced by the present methods. For example, at least 10%, 20%, 30%, 40%, 50%, 60%, 70%, 80%, or 90% or more of the microorganism, if present in and/or on the target or the treated target composition, can be killed, destroyed, removed and/or inactivated by the present methods.

In some embodiments, the antimicrobial efficacy of the composition used in the present methods on the treated water source is comparable to antimicrobial effect of a water source that does not contain produced water. In other embodiments, the treated water source reduces corrosion caused by hydrogen peroxide and reduces microbial-induced corrosion, and the composition used in the present methods does not substantially interfere with a friction reducer, a viscosity enhancer, other functional ingredients present in the treated water source, or a combination thereof.

The present methods can be used to reduce population of any suitable microbe(s) in and/or on the target or the treated target composition by any suitable magnitude. In some embodiments, the present methods can be used to reduce a prokaryotic microbial population, e.g., a bacterial or an archaeal population. In other embodiments, the present methods can be used to reduce an eukaryotic microbial population, e.g., a protozoal or fungal population. In still other embodiments, the present methods can be used to reduce a viral population. Exemplary viral population can comprise a population of a DNA virus, a RNA virus, and a reverse transcribing virus.

The present methods can be used to stabilize or reduce a microbial population in and/or on the target or the treated target composition, wherein the target is a food item or a plant item and the contacting step minimizes or does not induce an organoleptic effect in and/or on the food item or a plant item. Typical organoleptic properties include the aspects of food or other substances as experienced by the senses, including taste, sight, smell, and touch, in cases where dryness, moisture, and stale-fresh factors are to be considered. See e.g., Jasper Womach, the Congressional Research Service document "Report for Congress: Agriculture: A Glossary of Term, Programs, and Laws, 2005 Edition." In some embodiments, organoleptic procedures are performed as part of the meat and poultry inspections to detect signs of disease or contamination. In other embodiments, organoleptic tests are conducted to determine if package materials and components can transfer tastes and odors to the food or pharmaceutical products that they are packaged in. Shelf life studies often use taste, sight, and smell (in addition to food chemistry and toxicology tests) to determine whether a food product is suitable for consumption. In still other embodiments, organoleptic tests are conducted as part of the Hurdle technology. Typically, Hurdle technology refers to an intelligent combination of hurdles which secures the microbial safety and stability as well as the organoleptic and nutritional quality and the economic viability of food products. See generally, Leistner L (1995) "In Gould GW (Ed.) *New Methods of Food Preservation*, Springer, pp. 1-21; and Leistner I (2000) "*International Journal of Food Microbiology*, 55:181-186.

The present methods can be conducted at any suitable temperature range. In some embodiments, the present methods can be conducted at a temperature ranging from about 0° C. to about 70° C., e.g., about 0° C.-1° C., 1° C.-2° C., 2° C.-3° C., 3° C.-4° C., 4° C.-5° C., 5° C.-10° C., 10° C.-15° C., 15° C.-20° C., 20° C.-25° C., 25° C.-30° C., 30° C.-35° C., 35° C.-40° C., 40° C.-45° C., 45° C.-50° C., 50° C.-55° C., 55° C.-60° C., 60° C.-65° C., or 65° C.-70° C. In other embodiments, the present methods can be conducted at a temperature at or lower than 0° C.

In some embodiments, the present methods can comprise adding a peroxidase or a catalase to further reduce the hydrogen peroxide concentration in and/or on the target or the treated target composition. The peroxidase or catalase can be added in any suitable manner. In some embodiments, the peroxidase or catalase can be added to the target or the treated target composition before a composition used in the present methods is provided to the target, e.g., a water source. In other embodiments, the present compositions can be diluted into a suitable intermediate volume, and the peroxidase or catalase can be added to the diluted, intermediate volume. Thereafter, the diluted, intermediate volume, which contains the peroxidase or catalase, can be added to target, e.g., a water source. Any suitable peroxidase or catalase, including the ones described below, can be used in the present methods.

In some embodiments, the present methods can further comprise disposing of the treated water source or directing the treated water source into a subterranean environment, e.g., a subterranean environment that comprises a well in a gas and/or oil.

In some embodiments, the water source treated by the present methods does not comprise reuse water, the treated water source comprises from about 10 ppm to about 20 ppm of peroxyformic acid, e.g., in situ formed peroxyformic acid, and from about 1 ppm to about 2 ppm of hydrogen peroxide and the treated water source does not comprise a friction reducer and/or a rheology modifier.

In some embodiments, the water source treated by the present methods is a blended water source that comprises about 80 wt-% fresh water or pond water and about 20 wt-% of reuse water, the treated water source comprises from about 25 ppm to about 35 ppm of peroxyformic acid, e.g., in situ formed peroxyformic acid, and from about 2 ppm to about 3 ppm of hydrogen peroxide and catalase, the treated water source does not comprise a friction reducer and/or a rheology modifier, and the treated water source is formed before reaching a blending tub.

In some embodiments, the water source treated by the present methods is a blended water source that comprises about 80 wt-% fresh water or pond water and about 20 wt-% of reuse water, the treated water source comprises from about 25 ppm to about 35 ppm of peroxyformic acid, e.g., in situ formed peroxyformic acid, and from about 2 ppm to about 3 ppm of hydrogen peroxide and catalase, the treated water source comprises a friction reducer and/or a rheology modifier, and the treated water source is formed in a blending tub.

In some embodiments, the treated water source comprises from about 30 ppm or less of peroxyformic acid, e.g., in situ formed peroxyformic acid, and about 0.5 ppm or less of the hydrogen peroxide, the treated water source comprises a friction reducer and/or a rheology modifier, and the treated water source is directed into or is at a subterranean environment.

In some aspects, the methods disclosed for water treatment in oil and gas recovery provide effective antimicrobial efficacy without deleterious interaction with functional agents, including for example friction reducers. In a further aspect, the methods for water treatment provide increased antimicrobial efficacy compared to the use of the antimicrobial peracids alone. In a still further aspect, the methods of use result in the disposal of cleaner water with low numbers of microorganisms. In yet a further aspect of the methods of the invention, the reduction and/or elimination of $H_2O_2$ from the peracid compositions minimizes the negative effects of the oxidant $H_2O_2$.

Use in Water Treatment

The peroxyformic acid compositions can be used for a variety of industrial applications, e.g., to reduce microbial or viral populations on a surface or object or in a body or stream of water. In some aspects, the invention includes methods of using the peroxyformic acid compositions to prevent biological fouling in various industrial processes and industries, including oil and gas operations, to control microorganism growth, eliminate microbial contamination, limit or prevent biological fouling in liquid systems, process waters or on the surfaces of equipment that come in contact with such liquid systems. As referred to herein, microbial contamination can occur in various industrial liquid systems including, but not limited to, air-borne contamination, water make-up, process leaks and improperly cleaned equipment. In another aspect, peroxyformic acid and/or catalase compositions are used to control the growth of microorganisms in water used in various oil and gas operations. In a further aspect, the compositions are suitable for incorporating into fracturing fluids to control or eliminate microorganisms.

As used herein for the methods of the invention, the peroxyformic acid compositions can employ a variety of peroxyformic acid compositions having a low to substantially no hydrogen peroxide concentration. These peroxyformic acid compositions include peroxyformic acid compositions with a catalase or peroxidase enzyme to reduce the hydrogen peroxide to peracid ratio and/or other reduced hydrogen peroxide peroxyformic acid compositions disclosed herein. In a specific embodiment peroxyformic acid and catalase use solutions having reduced or substantially no hydrogen peroxide are introduced to a water source in need of treatment.

The methods by which the peroxyformic acid solutions are introduced into the aqueous fluids according to the invention are not critical. Introduction of the peroxyformic acid compositions may be carried out in a continuous or intermittent manner and will depend on the type of water being treated. In some embodiments, the peroxyformic acid compositions are introduced into an aqueous fluid according to the methods disclosed in U.S. Patent Publication No. 2014/0096971, titled "New Method and Arrangement for Feeding Chemicals into a Hydrofracturing Process and Oil and Gas Applications", which is hereby incorporated by reference in its entirety.

In an aspect, the peroxyformic acid solutions are added to waters in need of treatment prior to the drilling and fracking steps in order to restrict the introduction of microbes into the reservoir and to prevent the microbes from having a negative effect on the integrity of the fluids. The treatment of source waters (e.g. pond, lake, municipal, etc.) and/or produced waters is particularly well suited for use according to the invention.

The treated waters according to the invention can be used for both slick water fracturing (i.e. using frictions reducers) and/or gel fracturing (i.e. using viscosity enhancers), depending on the type of formation being fractured and the type of hydrocarbon expected to be produced. Use of a peroxyformic acid solution, including a catalase treated peroxyformic acid composition use solution having low to substantially no hydrogen peroxide, is suitable for both slick water fracturing and gel fracturing.

In an aspect, pretreating the peroxyformic acid composition with catalase substantially removes the hydrogen peroxide with minimal to no impact on the fracturing fluids and the well itself. In an aspect, the peroxyformic acid composition pretreated with catalase allows the formation of gel suitable for gel fracturing, as opposed to untreated peroxyformic acid composition solutions that do not allow a gel to form under certain conditions. In a further aspect, the peroxyformic acid composition solutions are added to waters in need of treatment in the subterranean well formations (e.g. introduced through a bore hole in a subterranean formation). These methods provide additional control within the well formation suitable for reducing microbial populations already present within the down-hole tubing in the well or within the reservoir itself.

In a still further aspect, the peroxyformic acid composition solutions are added to waters in need of treatment before disposal. In such an aspect, flow back waters (e.g. post fracking) are treated to minimize microbial contaminations in the waters and to remove solids prior to disposal of the water into a subterranean well, reuse in a subsequent fracturing application or return of the water into local environmental water sources.

In an aspect, the water source in need of treatment may vary significantly. For example, the water source may be a freshwater source (e.g. pond water), salt water or brine source, brackish water source, recycled water source, or the like. In an aspect, wherein offshore well drilling operations are involved, seawater sources are often employed (e.g. saltwater or non-saltwater). Beneficially, the peroxyformic acid compositions, with or without catalase, of the invention are suitable for use with any types of water and provide effective antimicrobial efficiency with any of such water sources.

Large volumes of water are employed according to the invention as required in well fluid operations. As a result, in an aspect of the invention, recycled water sources (e.g. produced waters) are often employed to reduce the amount of a freshwater, pond water or seawater source required. Recycled or produced water are understood to include non-potable water sources. The use of such produced waters (in combination with freshwater, pond water or seawater) reduces certain economic and/or environmental constraints. In an aspect of the invention, thousands to millions of gallons of water may be employed and the combination of produced water with fresh water sources provides significant economic and environmental advantages. In an aspect of the invention, as much produced water as practical is employed. In an embodiment at least 1% produced water is employed, preferably at least 5% produced water is employed, preferably at least 10% produced water is employed, preferably at least 20% produced water is employed, or more preferably more than 20% produced water is employed. In another aspect, up to 100% of produced water can be employed.

In an aspect of the invention, the method includes a pretreatment step, wherein the peroxyformic acid composition is treated with a catalase enzyme to reduce the hydrogen peroxide concentration in a use solution. The pretreatment step occurs prior to combining the peracid antimicrobial composition and/or catalase to a water source in need of treatment. In an aspect of the invention, the pretreatment may occur within a few minutes to hours before addition to a water source.

According to embodiments of the invention, a sufficient amount of the peroxyformic acid composition, with or without catalase, is added to the aqueous water source in need of treatment to provide the desired peroxyformic acid concentration for antimicrobial efficacy. For example, a water source is dosed amounts of the peroxyformic acid and catalase use solution composition until a peroxyformic acid concentration within the water source is detected within the preferred concentration range (e.g. about 1 ppm to about 100 ppm peracid). In an aspect, it is preferred to have a microbial count of less than about 100,000 microbes/mL, more preferably less than about 10,000 microbes/mL, or more preferably less than about 1,000 microbes/mL.

The methods of use as described herein can vary in the temperature and pH conditions associated with use of the aqueous treatment fluids. For example, the aqueous treatment fluids may be subjected to varying ambient temperatures according to the applications of use disclosed herein, including ranging from about 0° C. to about 130° C. in the course of the treatment operations. Preferably, the temperature range is between about 5° C. to about 100° C., more preferably between about 10° C. to about 80° C. However, as a majority of the antimicrobial activity of the compositions of the invention occurs over a short period of time, the exposure of the compositions to relatively high temperatures is not a substantial concern. In addition, the peracid composition aqueous treatment fluids (i.e. use solutions) may be subjected to varying pH ranges, such as from 1 to about 10.5. Preferably, the pH range is less than about 9, less than about 8.2 or 8 to ensure the effective antimicrobial efficacy of the peracid.

The antimicrobial compositions of the invention are fast-acting. However, the present methods require a certain minimal contact time of the compositions with the water in need of treatment for occurrence of sufficient antimicrobial effect. The contact time can vary with concentration of the use compositions, method of applying the use compositions, temperature of the use compositions, pH of the use compositions, amount of water to be treated, amount of soil or substrates in the water to be treated, or the like. The contact or exposure time can be at least about 15 seconds. In some embodiments, the exposure time is about 1 to 5 minutes. In other embodiments, the exposure time is at least about 10 minutes, 30 minutes, or 60 minutes. In other embodiments, the exposure time is a few minutes to hours. The contact time will further vary based upon the concentration of peracid in a use solution.

Beneficial Effects of the Methods of Use in Water Treatment In an aspect, the methods of use provide an antimicrobial for use that does not negatively impact the environment. Beneficially, the degradation of the compositions of the invention provides a "green" alternative.

In a further aspect, the methods of use provide an antimicrobial for use that does not negatively interfere with friction reducers, viscosity enhancers and/or other functional ingredients. In a further aspect, the methods of use do not negatively interfere with any additional functional agents utilized in the water treatment methods, including for example, corrosion inhibitors, descaling agents and the like. The compositions administered according to the invention provide extremely effective control of microorganisms without adversely affecting the functional properties of any additive polymers of an aqueous system. In addition, the peroxyformic acid compositions provide additional benefits to a system, including for example, reducing corrosion within the system due to the decreased or substantially eliminated hydrogen peroxide from a treated composition. Beneficially, the non-deleterious effects of the peroxyformic acid compositions (with or without a catalase) on the various functional ingredients used in water treatment methods are achieved regardless of the make-up of the water source in need of treatment.

In an additional aspect, the methods of use prevent the contamination of systems, such as well or reservoir souring. In further aspects, the methods of use prevent microbiologically-influenced corrosion of the systems upon which it is employed.

In further aspects, the methods of use employ the antimicrobial and/or bleaching activity of the peroxyformic acid compositions. For example, the invention includes a method for reducing a microbial population and/or a method for bleaching. These methods can operate on an article, surface, in a body or stream of water or a gas, or the like, by contacting the article, surface, body, or stream with the compositions. Contacting can include any of numerous methods for applying the compositions, including, but not limited to, providing the antimicrobial peroxyformic acid compositions in an aqueous use solution and immersing any articles, and/or providing to a water source in need of treatment.

The compositions are suitable for antimicrobial efficacy against a broad spectrum of microorganisms, providing broad spectrum bactericidal and fungistatic activity. For example, the peracid biocides of this invention provide broad spectrum activity against wide range of different types of microorganisms (including both aerobic and anaerobic microorganisms), including bacteria, yeasts, molds, fungi, algae, and other problematic microorganisms associated with oil- and gas-field operations.

Exemplary microorganisms susceptible to the peracid compositions of the invention include, gram positive bacteria (e.g., *Staphylococcus aureus, Bacillus* species (sp.) like *Bacillus subtilis*, Clostridia sp.), gram negative bacteria (e.g., *Escherichia coli, Pseudomonas* sp., *Klebsiella pneumoniae, Legionella pneumophila, Enterobacter* sp., *Serratia* sp., *Desulfovibrio* sp., and *Desulfotomaculum* sp.), yeasts (e.g., *Saccharomyces cerevisiae* and *Candida albicans*), molds (e.g., *Aspergillus niger, Cephalosporium acremonium, Penicillium notatum*, and *Aureobasidium pullulans*), filamentous fungi (e.g., *Aspergillus niger* and *Cladosporium resinae*), algae (e.g., *Chlorella vulgaris, Euglena gracilis*, and *Selenastrum capricornutum*), and other analogous microorganisms and unicellular organisms (e.g., phytoplankton and protozoa). Other exemplary microorganisms susceptible to the peracid compositions of the invention include the exemplary microorganisms disclosed in U.S. patent application US 2010/0160449 A1, e.g., the sulfur- or sulfate-reducing bacteria, such as *Desulfovibrio* and *Desulfotomaculum* species.

Use in Other Treatments

Additional embodiments of the invention include water treatments for various industrial processes for treating liquid systems. As used herein, "liquid system" refers to flood waters or an environment within at least one artificial artifact, containing a substantial amount of liquid that is capable of undergoing biological fouling. Liquid systems include but are not limited to industrial liquid systems, industrial water systems, liquid process streams, industrial liquid process streams, industrial process water systems, process water applications, process waters, utility waters, water used in manufacturing, water used in industrial services, aqueous liquid streams, liquid streams containing two or more liquid phases, and any combination thereof.

In a further aspect, the present methods can also be used to treat other liquid systems where both the compositions' antimicrobial function and oxidant properties can be utilized. Aside from the microbial issues surrounding waste water, waste water is often rich in malodorous compounds of reduced sulfur, nitrogen or phosphorous. A strong oxidant such as the compositions disclosed herein converts these compounds efficiently to their odor free derivatives e.g. the sulfates, phosphates and amine oxides. These same properties are very useful in the pulp and paper industry where the property of bleaching is also of great utility.

The present methods can be conducted at any suitable temperature. In some embodiments, the present methods are conducted at a temperature ranging from about −2° C. to about 70° C., e.g., from about −2° C. to about 5° C., from about 0° C. to about 4° C. or 5° C., from about 5° C. to about 10° C., from about 11° C. to about 20° C., from about 21° C. to about 30° C., from about 31° C. to about 40° C., including at about 37° C., from about 41° C. to about 50° C., from about 51° C. to about 60° C., or from about 61° C. to about 70° C.

The present methods can be used in the methods, processes or procedures described and/or claimed in U.S. Pat. Nos. 5,200,189, 5,314,687 and 5,718,910. In some embodiments, the present methods can be used of sanitizing facilities or equipment comprises the steps of contacting the facilities or equipment with the composition of the present invention at a temperature in the range of about 4° C. to about 60° C. The peroxyformic acid composition is then circulated or left in contact with the facilities or equipment for a time sufficient to sanitize (generally at least 30 seconds) and the treated target composition is thereafter drained or removed from the facilities or equipment.

As noted above, the present methods are useful in the cleaning or sanitizing of processing facilities or equipment in the food service, food processing or health care industries. Examples of process facilities in which the present methods can be employed include a milk line dairy, a continuous brewing system, food processing lines such as pumpable food systems and beverage lines, etc. Food service wares can also be disinfected with the present methods. The present methods are also useful in sanitizing or disinfecting solid surfaces such as floors, counters, furniture, medical tools and equipment, etc., found in the health care industry. Such surfaces often become contaminated with liquid body spills such as blood, other hazardous body fluids or mixtures thereof.

Generally, the actual cleaning of the in-place system or other surface (i.e., removal of unwanted offal therein) can be accomplished with a different material such as a formulated detergent which is introduced with heated water. After this cleaning step, the peroxyformic acid composition can be applied or introduced into the system at a use solution concentration in unheated, ambient temperature water. In some embodiments, the peroxyformic acid composition is found to remain in solution in cold (e.g., 40° F./4° C.) water and heated (e.g., 140° F./60° C.) water. Although it is not normally necessary to heat the aqueous use solution of the peroxyformic acid composition, under some circumstances heating may be desirable to further enhance its antimicrobial activity.

In some embodiments, a method of sanitizing substantially fixed in-place process facilities comprises the following steps. The peroxyformic acid composition of the present invention is introduced into the process facilities at a temperature in the range of about 4° C. to about 60° C. After introduction of the use solution, the solution is circulated throughout the system for a time sufficient to sanitize the process facilities (i.e., to kill undesirable microorganisms). After the system has been sanitized by means of the present composition, the use composition or solution is drained from the system. Upon completion of the sanitizing step, the system optionally may be rinsed with other materials such as potable water. The present composition is preferably circulated through the process facilities for 10 minutes or less.

In other embodiments, the present peroxyformic acid composition may also be employed by dipping food processing equipment into the diluted (or use) composition or solution of the present invention, soaking the equipment for a time sufficient to sanitize the equipment, and wiping or draining excess solution off the equipment. The composition may be further employed by spraying or wiping food processing surfaces with the use solution, keeping the surfaces wet for a time sufficient to sanitize the surfaces, and removing the excess composition or solution by wiping, draining vertically, vacuuming, etc.

In still other embodiments, the present peroxyformic acid composition may also be used in a method of sanitizing hard surfaces such as institutional type equipment, utensils, dishes, health care equipment or tools, and other hard surfaces. The present peroxyformic acid composition may also be employed in sanitizing clothing items or fabric which has become contaminated. The peroxyformic acid composition is contacted with any of the above contaminated surfaces or items at use temperatures in the range of about 4° C. to about 60° C. for a period of time effective to sanitize, disinfect, or sterilize the surface or item. For example, the present composition can be injected into the wash or rinse water of a laundry machine and contacted with contaminated fabric for a time sufficient to sanitize the fabric. Excess composition or solution can then be removed by rinsing or centrifuging the fabric.

The present methods can be used in the methods, processes or procedures described and/or claimed in U.S. Pat. Nos. 6,165,483 and 6,238,685, to treat field or greenhouse grown plant tissue, seeds, fruits, and growing media and containers. The present peroxyformic acid composition can lower the natural, plant pathogen and human pathogenic microbial load resulting in less waste to molding, spoilage, and destruction because of pathogenic poisons.

In some embodiments, the present peroxyformic acid composition can be used to protect growing plant tissue from the undesirable effects of microbial attack. The present peroxyformic acid composition can be applied to growing plant tissues and can provide residual antimicrobial effects after the plant has completed its growth cycle, fruit or vegetable material have been harvested and sent to market. The present composition can be an effective treatment of living or growing plant tissues including seeds, roots, tubers, seedlings, cuttings, rooting stock, growing plants, produce, fruits and vegetables, etc. Under certain circumstances, a single peroxyacid material can be effective, however, in other circumstances, a mixed peroxy acid has substantially improved and surprising properties.

In some embodiments, the composition used in the present methods also may contain a hydrotrope for the purpose of increasing the aqueous solubility of various slightly soluble organic compounds. The preferred embodiment of the composition utilizes a hydrotrope chosen from the group of n-octanesulfonate, a xylene sulfonate, a naphthalene sulfonate (naphthenic acid), ethylhexyl sulfate, lauryl sulfate, an amine oxide, or a mixture thereof.

In some embodiments, the composition used in the present methods may also contain a chelating agent for the purpose of removing ions from solution. The preferred embodiment of the invention uses 1-hydroxyethylidene-1,1-diphosphonic acid.

The present methods can be used in the methods, processes or procedures described and/or claimed in U.S. Pat. Nos. 6,010,729, 6,103,286, 6,545,047 and 8,030,351 for sanitizing animal carcasses.

In some embodiments, the compositions of the present invention can be used in a method of treating animal carcasses to obtain a reduction by at least one $\log_{10}$ in surface microbial population which method includes the step of treating said carcass with a composition of the present invention comprising an effective antimicrobial amount comprising at least 2 parts per million (ppm, parts by weight per each one million parts) of one or more peroxycarboxylic acids having up to 12 carbon atoms, an effective antimicrobial amount comprising at least 20 ppm of one or more carboxylic acids having up to 18 carbon atoms, and the first and second stabilizing agents described above, to reduce the microbial population.

In yet other embodiments, the present invention is directed to a method of treating an animal carcass to reduce a microbial population in resulting cut meat, the method comprising the steps of spraying an aqueous antimicrobial treatment composition onto said carcass at a pressure of at least 50 psi at a temperature of up to about 60° C. resulting in a contact time of at least 30 seconds, the antimicrobial composition comprising an effective antimicrobial amount comprising least 2 ppm of one or more carboxylic acid, peroxycarboxylic acid or mixtures thereof, and the first and second stabilizing agents described above; and achieving at least a one $\log_{10}$ reduction in the microbial population.

In yet other embodiments, the present invention is directed to a method of treating an animal carcass to reduce a microbial population in resulting cut meat, the method comprising the steps of placing the animal carcass in a chamber at atmospheric pressure; filling the chamber with condensing steam comprising an antimicrobial composition, e.g., a diluted composition of the present invention, for a short duration; and quickly venting and cooling the chamber to prevent browning of the meat carcass; wherein the duration of the steam thermal process may be from about 5 seconds to about 30 seconds and the chamber temperature may reach from about 50° C. to about 93° C.

The antimicrobial composition can be applied in various ways to obtain intimate contact with each potential place of microbial contamination. For example, it can be sprayed on the carcasses, or the carcasses can be immersed in the composition. Additional methods include applying a foamed composition and a thickened or gelled composition. Vacuum and or light treatments can be included, if desired, with the application of the antimicrobial composition. Thermal treatment can also be applied, either pre-, concurrent with or post application of the antimicrobial composition.

One preferred spray method for treating carcasses with diluted compositions of the present invention involves spraying the carcass with an aqueous spray at a temperature less than about 60° C. at a pressure of about 50 to 500 psi gauge wherein the spray comprises an effective antimicrobial amount of a carboxylic acid, an effective antimicrobial amount of a peroxycarboxylic acid or mixtures thereof, and the first and second stabilizing agents described above. These sprays can also contain an effective portion of a peroxy compound such as hydrogen peroxide and other ingredients such as sequestering agents, etc. The high pressure spray action of the aqueous treatment can remove microbial populations by combining the mechanical action of the spray with the chemical action of the antimicrobial materials to result in an improved reduction of such populations on the surface of the carcass.

All pressures are psig (or psi gauge). In some embodiments, differentiation of antimicrobial "-cidal" or "-static" activity, the definitions which describe the degree of efficacy, and the official laboratory protocols for measuring this efficacy are important considerations for understanding the relevance of antimicrobial agents in compositions. Antimicrobial compositions may affect two kinds of microbial cell damages. The first is a truly lethal, irreversible action resulting in complete microbial cell destruction or incapacitation. The second type of cell damage is reversible, such that if the organism is rendered free of the agent, it can again multiply. The former is termed bacteriocidal and the latter, bacteriostatic. A sanitizer and a disinfectant are, by definition, agents which provide antibacterial or bacteriocidal activity and may achieve at least a five-fold reduction (i.e., a five $\log_{10}$ reduction) in microbial populations after a 30 second contact time (see AOAC method 960.09).

The present methods can be used in the methods, processes or procedures described and/or claimed in U.S. Pat. Nos. 8,017,409 and 8,236,573. In some embodiments, the present methods may be used for a variety of domestic or industrial applications, e.g., to reduce microbial or viral populations on a surface or object or in a body or stream of water. The peroxyformic acid compositions of the present invention may be applied in a variety of areas including kitchens, bathrooms, factories, hospitals, dental offices and food plants, and may be applied to a variety of hard or soft surfaces having smooth, irregular or porous topography. Suitable hard surfaces include, for example, architectural surfaces (e.g., floors, walls, windows, sinks, tables, counters and signs); eating utensils; hard-surface medical or surgical instruments and devices; and hard-surface packaging. Such hard surfaces may be made from a variety of materials including, for example, ceramic, metal, glass, wood or hard plastic. Suitable soft surfaces include, for example paper; filter media, hospital and surgical linens and garments; soft-surface medical or surgical instruments and devices; and soft-surface packaging. Such soft surfaces may be made from a variety of materials including, for example, paper, fiber, woven or non-woven fabric, soft plastics and elastomers. The diluted (or use) compositions may also be applied to soft surfaces such as food and skin (e.g., a hand). The diluted (or use) compositions may be employed as a foaming or non-foaming environmental sanitizer or disinfectant.

In other embodiments, the peroxyformic acid compositions of the present invention may be included in products such as sterilants, sanitizers, disinfectants, preservatives, deodorizers, antiseptics, fungicides, germicides, sporicides, virucides, detergents, bleaches, hard surface cleaners, hand soaps, waterless hand sanitizers, and pre- or post-surgical scrubs.

In still other embodiments, the peroxyformic acid compositions of the present invention may also be used in veterinary products such as mammalian skin treatments or in products for sanitizing or disinfecting animal enclosures, pens, watering stations, and veterinary treatment areas such as inspection tables and operation rooms. The peroxyformic acid compositions may be employed in an antimicrobial foot bath for livestock or people.

In yet other embodiments, the present methods may be employed for reducing the population of pathogenic microorganisms, such as pathogens of humans, animals, and the like. Exemplary pathogenic microorganisms include fungi, molds, bacteria, spores, and viruses, for example, S. aureus, E. coli, Streptococci, Legionella, Pseudomonas aeruginosa, mycobacteria, tuberculosis, phages, or the like. Such pathogens may cause a variety of diseases and disorders, including Mastitis or other mammalian milking diseases, tuberculosis, and the like. The present methods may be used to reduce the population of microorganisms on skin or other external or mucosal surfaces of an animal. In addition, the present methods may be used to kill pathogenic microorganisms that spread through transfer by water, air, or a surface substrate. In some applications, the compositions of the present invention need only be applied to the skin, other external or mucosal surfaces of an animal water, air, or surface.

In yet other embodiments, the present methods may also be used on foods and plant species to reduce surface microbial populations; used at manufacturing or processing sites handling such foods and plant species; or used to treat process waters around such sites. For example, the present methods may be used on food transport lines (e.g., as belt sprays); boot and hand-wash dip-pans; food storage facilities; anti-spoilage air circulation systems; refrigeration and cooler equipment; beverage chillers and warmers, blanchers, cutting boards, third sink areas, and meat chillers or scalding devices. The present methods may be used to treat transport waters such as those found in flumes, pipe transports, cutters, slicers, blanchers, retort systems, washers, and the like. Particular foodstuffs that may be treated with the present methods include eggs, meats, seeds, leaves, fruits and vegetables. Particular plant surfaces include both harvested and growing leaves, roots, seeds, skins or shells, stems, stalks, tubers, corms, fruit, and the like. The present methods may also be used to treat animal carcasses to reduce both pathogenic and non-pathogenic microbial levels.

In yet other embodiments, the present methods may be useful in the cleaning or sanitizing of containers, processing facilities, or equipment in the food service or food processing industries. The present methods may be used on food packaging materials and equipment, including for cold or hot aseptic packaging. Examples of process facilities in which the present methods may be employed include a milk line dairy, a continuous brewing system, food processing lines such as pumpable food systems and beverage lines, etc. Food service wares may be disinfected with the present methods. For example, the present methods may also be used on or in ware wash machines, dishware, bottle washers, bottle chillers, warmers, third sink washers, cutting areas (e.g., water knives, slicers, cutters and saws) and egg washers. Particular treatable surfaces include packaging such as cartons, bottles, films and resins; dish ware such as glasses, plates, utensils, pots and pans; ware wash machines; exposed food preparation area surfaces such as sinks, counters, tables, floors and walls; processing equipment such as tanks, vats, lines, pumps and hoses (e.g., dairy processing equipment for processing milk, cheese, ice cream and other dairy products); and transportation vehicles. Containers include glass bottles, PVC or polyolefin film sacks, cans, polyester, PEN or PET bottles of various volumes (100 ml to 2 liter, etc.), one gallon milk containers, paper board juice or milk containers, etc.

In yet other embodiments, the present methods may also be used on or in other industrial equipment and in other industrial process streams such as heaters, cooling towers, boilers, retort waters, rinse waters, aseptic packaging wash waters, and the like. The present methods may be used to treat microbes and odors in recreational waters such as in pools, spas, recreational flumes and water slides, fountains, and the like.

In yet other embodiments, a filter containing the peroxyformic acid compositions of the present invention may be used to reduce the population of microorganisms in air and liquids. Such a filter may be used to remove water and air-born pathogens such as Legionella.

In yet other embodiments, the present methods may be employed for reducing the population of microbes, fruit flies, or other insect larva on a drain or other surface.

In yet other embodiments, the present methods may also be employed by dipping food processing equipment into the peroxyformic acid composition or solution of the present invention, soaking the equipment for a time sufficient to sanitize the equipment, and wiping or draining excess composition or solution off the equipment. The present methods may be further employed by spraying or wiping food processing surfaces with the peroxyformic acid composition or solution, keeping the surfaces wet for a time sufficient to sanitize the surfaces, and removing excess composition or solution by wiping, draining vertically, vacuuming, etc.

In yet other embodiments, the present methods may also be used for sanitizing hard surfaces such as institutional type equipment, utensils, dishes, health care equipment or tools, and other hard surfaces. The present methods may also be employed in sanitizing clothing items or fabrics which have become contaminated. The peroxyformic acid compositions of the present invention can be contacted with any contaminated surfaces or items at use temperatures in the range of about 4° C. to 60° C., for a period of time effective to sanitize, disinfect, or sterilize the surface or item. For example, the peroxyformic acid compositions may be injected into the wash or rinse water of a laundry machine and contacted with contaminated fabric for a time sufficient to sanitize the fabric. Excess composition may be removed by rinsing or centrifuging the fabric.

In yet other embodiments, the peroxyformic acid compositions of the present invention may be applied to microbes or to soiled or cleaned surfaces using a variety of methods. These methods may operate on an object, surface, in a body or stream of water or a gas, or the like, by contacting the object, surface, body, or stream with the diluted (or use) composition. Contacting may include any of numerous methods for applying a composition, such as spraying the composition, immersing the object in the composition, foam or gel treating the object with the composition, or a combination thereof.

In yet other embodiments, the peroxyformic acid compositions of the present invention may be employed for bleaching pulp. The compositions may be employed for waste treatment. Such a composition may include added bleaching agent.

In yet other embodiments, other hard surface cleaning applications for the peroxyformic acid compositions of the present invention include clean-in-place systems (CIP), clean-out-of-place systems (COP), washer-decontaminators, sterilizers, textile laundry machines, ultra and nano-filtration systems and indoor air filters. COP systems may include readily accessible systems including wash tanks, soaking vessels, mop buckets, holding tanks, scrub sinks, vehicle parts washers, non-continuous batch washers and systems, and the like.

The concentrations of peroxyformic acid and/or hydrogen peroxide in the peroxyformic acid compositions of the present invention can be monitored in any suitable manner. In some embodiments, the concentrations of peroxyformic acid and/or hydrogen peroxide in the peroxyformic acid and/or hydrogen peroxide compositions can be monitored using a kinetic assay procedure, e.g., the exemplary procedure disclosed in U.S. Pat. Nos. 8,017,409 and 8,236,573. This can be accomplished by exploiting the difference in reaction rates between peroxyformic acid and hydrogen peroxide when using, for example, a buffered iodide reagent to differentiate peroxyformic acid and hydrogen peroxide concentrations when both these analyte compounds are present in the use composition. The monitor may also determine the concentrations of peroxyformic acid and/or hydrogen peroxide in the presence of other additional ingredients, such as acidulants, one or more stabilizing agents, nonionic surfactants, semi-polar nonionic surfactants, anionic surfactants, amphoteric or ampholytic surfactants, adjuvants, solvents, additional antimicrobial agents or other ingredients which may be present in the use composition.

Methods of cleaning a Food Process Surface

As noted above, the present methods are useful in the cleaning or sanitizing of processing facilities or equipment in the food service, food processing or health care industries. Examples of process facilities in which the present methods can be employed include a milk line dairy, a continuous brewing system, food processing lines such as pumpable food systems and beverage lines, etc. Food service wares can also be disinfected with the present methods. The present methods are also useful in sanitizing or disinfecting solid surfaces such as floors, counters, furniture, medical tools and equipment, etc., found in the health care industry. Such surfaces often become contaminated with liquid body spills such as blood, other hazardous body fluids or mixtures thereof.

Brewery soils are a type of soil that is particularly difficult to remove from a surface. Brewing beer requires the fermentation of sugars derived from starch-based material. Fermentation uses yeast to turn the sugars in wort to alcohol and carbon dioxide. During fermentation, the wort becomes beer. Once the boiled wort is cooled and in a fermenter, yeast is propagated in the wort and it is left to ferment, which requires a week to months depending on the type of yeast and strength of the beer. In addition to producing alcohol, fine particulate matter suspended in the wort settles during fermentation. Once fermentation is complete, the yeast also settles, leaving the beer clear, but the fermentation tanks soiled. Often during the fermentation process in commercial brewing, the fermentation tanks develop a ring of soil which is particularly difficult to remove. Traditional CIP methods of cleaning these tanks do not always remove this soil. Thus, brewers often resort to climbing inside of the tanks and manually scrubbing them to remove the soil. Accordingly there is need for improved methods and chemistries for removing these types of soils that are not easily removed using conventional cleaning techniques.

Brewery Surface CIP Single Use Technique

According to an embodiment of the invention, the method of cleaning may be used in a brewery surface CIP technique, including under an enriched $CO_2$ atmosphere. In a further embodiment, the CIP technique may employ single use equipment. The method can be performed at a temperature between about 5° C. and about 100° C. In another embodiment of the invention, the method can be performed at a temperature between about 25° C. and about 60° C. In a further embodiment of the invention, the method can be performed at a temperature between about 35° C. and about 50° C.

The peroxyformic acid composition will be contacted with the brewery surface CIP equipment as a use solution. The contacting can be performed in any suitable way. In an embodiment employing single use equipment, the method of cleaning does not return the use solution to a supply tank or recirculate it in a closed loop. Rather the use solution, remains in the CIP equipment during the wash cycle. In a particular embodiment, optimal cleaning may occur when the use solution has an alkaline pH, e.g., above pH 8 (and accordingly use of an alkalinity source may be employed). In a further aspect, the pH of the use solution may be monitored by any known method of monitoring pH, including for example a built-in pH meter. In a particular embodiment of the invention, the pH and/or conductivity of the use solution may be adjusted by adding an alkalinity source. In other embodiments of the invention, the pH and/or conductivity may not be monitored and adjusted.

Brewery Surface CIP Closed Loop Technique

According to an embodiment of the invention the method of cleaning may be used in a brewery surface CIP closed loop technique, including under an enriched $CO_2$ atmosphere. The method can be performed at a temperature between about 5° C. and about 100° C. In another embodiment of the invention, the method can be performed at a temperature between about 25° C. and about 60° C. In a further embodiment of the invention, the method can be performed at a temperature between about 35° C. and about 50° C.

In an embodiment employing closed loop equipment, the method of cleaning can recirculate the use solution through the brewery surface being cleaned. Thus, in a particular embodiment the recirculation of the use solution can be performed in any suitable method of recirculating the use solution. Such methods are well known and understood by those of skill in the art. An example, includes, but is not limited to, using a closed loop that recirculates the use solution through a built-in spray nozzle.

In a particular embodiment, optimal cleaning may occur when the use solution has an alkaline pH, e.g., pH equal to and greater than 8. In a particular embodiment of the invention, a secondary alkalinity source may be added to the use solution. In a further aspect of the invention, the pH of the use solution may be monitored by any known method of monitoring pH, including for example a built-in pH meter. In a particular embodiment of the invention, the pH of the use solution may be adjusted by adding an alkalinity source. In an aspect of the invention adding an alkalinity source may comprise recirculating the use solution, recirculating the use solution with another alkalinity source, or simply adding another alkalinity source. In other embodiments of the invention, the pH may not be monitored and adjusted.

In still a further aspect of the invention, the conductivity of the use solution may be monitored by any known method of monitoring conductivity, including for example a built-in conductivity meter. In a particular embodiment of the invention, the conductivity of the use solution may be adjusted by adding a secondary alkalinity source. In other embodiments of the invention, the conductivity may not be monitored and adjusted.

According to an embodiment of the invention, a food process surface is contacted by a cleaning composition. The cleaning composition may be in a concentrate or a diluted form generated according to the invention. Contacting can include any of numerous methods known by those of skill in the art for applying a compound or composition of the invention, such as spraying, immersing the food process surface in the cleaning composition or use solution, dispensing the cleaning composition over a surface in granular or particulate form, simply pouring the cleaning composition or a use solution onto or into the food process surface, rinsing the food processing surface with a use solution, or a combination thereof.

Low Temperature Cleaning Applications

In other applications, lower temperatures can be employed for effective soil removal employing the peroxyformic acid compositions. In some aspects, the methods of the present invention provide for effective soil removal without the necessity of high temperatures, i.e., above 60° C. Beneficially, the methods of the present invention do not require the surface to be cleaned to be preheated. In some aspects, the methods of the present invention are more effective at lower temperatures than at higher temperatures, contrary to conventional CIP methods of cleaning.

In some aspects, the cleaning employing the peroxyformic acid composition occur at a temperature of about 2° C. to about 50° C. In some embodiments, the methods of the present invention provide effective soil removal at ambient or room temperature, i.e., about 18° C. to about 23° C. All values and ranges between these values and ranges are to be encompassed by the methods of the present invention. Beneficially, the ability to clean at reduced temperatures results in energy and cost savings compared to traditional cleaning techniques that require increased temperatures. Further, the present invention provides for effective soil removal on surfaces that cannot withstand high temperatures.

Examples

The following examples are included for illustrative purposes only and are not intended to limit the scope of the invention.

Equilibrium peroxide is a required reagent and reaction product outcome of all stable peroxy acid systems. In many applications, this concentration of peroxide can be a disadvantage for both concentrate and use dilution outcome for use due to shipping or downstream treatment process complications.

Removal of use dilution peroxide can be achieved with various ways including scrubbing the use concentration with enzymatic or halogen based chemistries. In these cases, cost and time are an issue for effective peroxide removal. Enzymatic peroxide removal is especially unviable in this environment because of high cost and instabilities associated with the reaction conditions for the enzyme. Therefore there is a need for a process of preparing a rapid release of oxygen while maintaining a pseudo stable concentrate after 24 hours.

One exemplary reagent is formic acid which leverages a unique rate of formation in combination with equilibrium peracid systems. In exemplary embodiments, formic acid can act in two ways. First, use of formic acid in combination with an equilibrium peracid system can lead to rapid reduction of peroxide from the equilibrium formulation without gas release or exothermic reaction. Second, during consumption of peroxide, formic acid can form a semi-stable peracid with enhanced antimicrobial, oxidation, and bleaching performance.

In exemplary embodiments, performic acid can be used as an alternative way to treat water in oil and gas industry that has the same or better performance as peracetic acid systems, but reduce or minimize oxygen related corrosion issues. Performic acid provides for significant advantages in that it can be formulated at a high or higher ratio of peracid to peroxide; it does not generate oxygen, and has significantly reduced corrosion rates as compared to peracetic acid. Performic acid also exhibits a better biocidal activity and reduces risks associated with microbial induced corrosion. These advantages make performic acid a good or an ideal choice for use in both on shore and offshore oil and/or gas exploration, production and completions. In addition, a very low peroxide in the formulations containing a high or higher ratio of peracid to peroxide increases the compatibilities with sensitive chemistries in unconventional oil and gas production (like Frac Gel applications). The ability to oxidize iron sulfide and $H_2S$ and the antimicrobial properties provide performic acid for a unique advantage for the use in the oil and gas industry.

Example 1. Addition of Formic Acid to Peracetic Acid/Hydrogen Peroxide and Peroctanoic/Hydrogen Peroxide Systems. Addition of Formic Acid to a Peracetic Acid/Hydrogen Peroxide System In this example, formic acid was added to a peracetic acid/hydrogen peroxide system to form a composition that contains performic acid. Formic acid was added to a final ratio of 20:80 formic acid: peracetic acid formulation (17.2% POAA, 3.6% $H_2O_2$). As shown in Table 1 below and in FIG. 1, addition of formic acid to the peracetic acid/hydrogen peroxide system increases total peracid concentration while decreasing hydrogen peroxide concentration.

TABLE 1

Addition of formic acid to a peracetic acid/hydrogen peroxide system

| time (min) | peracetic acid formulation + formic acid | | total peracid/ $H_2O_2$ |
|---|---|---|---|
| | % total peracid | % $H_2O_2$ | |
| 0 | 13.8 (calculated value) | 2.9 (calculated value) | |
| 2 | 14.9 | 2.5 | 5.9 |
| 3 | 16.5 | 2.6 | 6.4 |
| 5 | 16.5 | 2.5 | 6.5 |
| 10 | 16.8 | 2.5 | 6.9 |
| 15 | 17.5 | 1.9 | 9.3 |
| 20 | 17.0 | 1.7 | 10.2 |
| 50 | 18.4 | 1.23 | 14.4 |
| 105 | 20.6 | 0.5 | 42.9 |
| 290 | 19.8 | 0.7 | 30.5 |
| 400 | 18.3 | 0.6 | 31.0 |
| 1680 | 13.8 | 0.2 | 58.9 |
| 2760 | 13.3 | 0.2 | 63.5 |

Addition of Formic Acid to a Peroctanoic Formulation (Octave FS)

In this example, formic acid was added to a peroctanoic acid/hydrogen peroxide system to form a composition that contains performic acid. Table 2 below shows addition of formic acid to a commercially-available peroctanoic formulation (POOA) at different ratios.

TABLE 2

Addition of formic acid to a peroctanoic formulation (POOA, contains 0.5% POOA and 6.8% $H_2O_2$) at different ratios

| | 0% | 4% | 8% | 16% | 32% |
|---|---|---|---|---|---|
| POOA (mL) | 5.0 | 5.0 | 5.0 | 5.0 | 5.0 |
| Water (in mL) | 5.0 | 4.6 | 4.2 | 3.4 | 1.8 |

TABLE 2-continued

Addition of formic acid to a peroctanoic formulation (POOA, contains 0.5% POOA and 6.8% $H_2O_2$) at different ratios

|  | 0% | 4% | 8% | 16% | 32% |
|---|---|---|---|---|---|
| Formic acid in mL) |  | 0.4 | 0.8 | 1.6 | 3.2 |
| Total (in mL) | 10.0 | 10.0 | 10.0 | 10.0 | 10.0 |

Table 3 below lists the amount of total peracids formed (mixture of peroctanoic and performic acids) in formulations containing varying amounts of formic acid (0 to 32%). Table 4 below shows total peracids and corresponding $H_2O_2$ concentration in formulations containing different ratios of formic acid (0 to 32%) in 50% POOA (0.25% POOA, 3.4% $H_2O_2$) after 1690 min incubation at 22° C.

TABLE 3

The amount of total peracids formed in formulations containing varying amounts of formic acid

| Time (min.) | 32% Formic acid | 16% Formic acid | 8% Formic acid | 4% Formic acid | 0% Formic acid |
|---|---|---|---|---|---|
| 20 | 1.9 | 0.7 | 0.4 | 0.2 |  |
| 80 | 2.0 | 0.7 | 0.3 | 0.3 |  |
| 155 | 2.5 | 1.0 | 0.5 | 0.3 |  |
| 255 | 1.9 | 0.8 | 0.4 | 0.3 | 0.1 |
| 1330 | 1.6 | 0.8 | 0.4 | 0.3 | 0.1 |

TABLE 4

Total peracids and corresponding $H_2O_2$ concentration in formulations containing different ratios of formic acid in 50% POOA after 1690 min incubation at 22° C.

|  | 32% | 16% | 8% | 4% | 0% |
|---|---|---|---|---|---|
| PFA + POOA (in %) | 2.0 | 1.3 | 0.8 | 0.5 | 0.2 |
| Peroxide (in %) | 1.1 | 2.0 | 2.2 | 2.5 | 3.0 |

Figure 2:
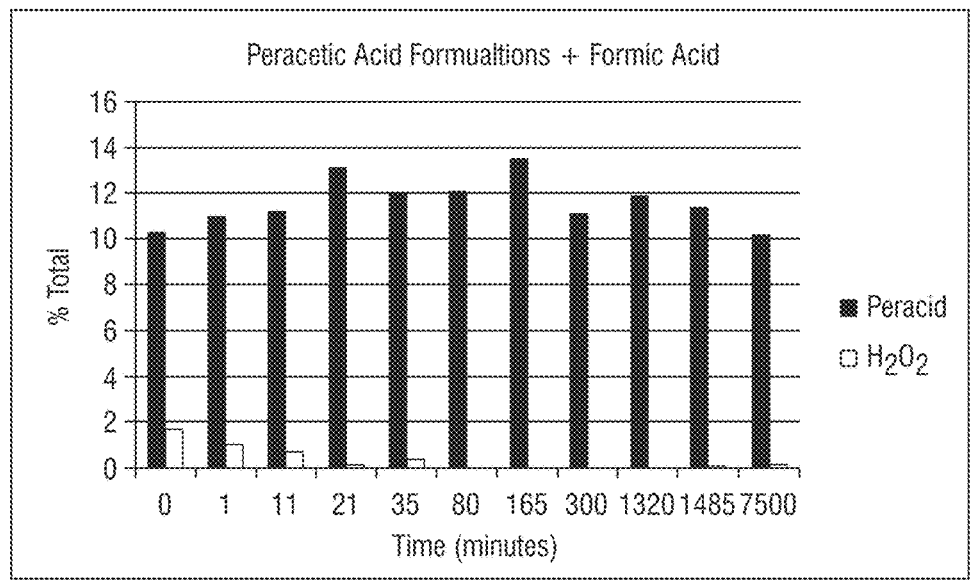
FIG. 2 illustrates addition of formic acid to a peracid system containing peracetic acid and hydrogen peroxide that results in a shift towards low hydrogen peroxide concentrations according to embodiments of the invention.

Example 2. Addition of 1:1 Ratio Formic Acid to a Peracid System. Addition of Formic Acid to a Peracetic Acid/Hydrogen Peroxide System In this example, formic acid was added to a peracetic acid/hydrogen peroxide system to form a composition that contains performic acid. As shown in Table 5 below and in FIG. 2, addition of 1:1 ratio formic acid to a peracid system (20.68% POAA, 3.43% $H_2O_2$) results in shift towards very low peroxide concentrations the composition of which is stable even after 5 days of mixing.

TABLE 5

Reduction in the concentration of peroxide in a peracetic acid/hydrogen peroxide system with formic acid

| Time (min) | Wt (g) | EP1 (ml) | EP2 (ml) | % (as POAA) | % $H_2O_2$ |
|---|---|---|---|---|---|
| 0 |  |  |  | 10.3 | 1.7 |
| 1 | 0.2970 | 8.6 | 1.8 | 11.0 | 1.0 |
| 11 | 0.3500 | 10.3 | 1.4 | 11.2 | 0.7 |
| 21 | 0.264 | 9.1 | 0.2 | 13.1 | 0.1 |
| 35 | 0.3095 | 9.8 | 0.7 | 12.0 | 0.4 |
| 80 | 0.2788 | 8.9 | 0.0 | 12.1 | 0.0 |
| 165 | 0.2138 | 7.6 | 0.0 | 13.5 | 0.0 |
| 300 | 0.2150 | 6.3 | 0.0 | 11.1 | 0.0 |
| 1320 | 0.2925 | 9.2 | 0.0 | 11.9 | 0.0 |
| 1485 | 0.2324 | 7.0 | 0.1 | 11.4 | 0.1 |
| 7500 | 0.2050 | 5.5 | 0.2 | 10.2 | 0.2 |

Addition of Formic Acid to a Peroctanoic Formulation

Figure 3:
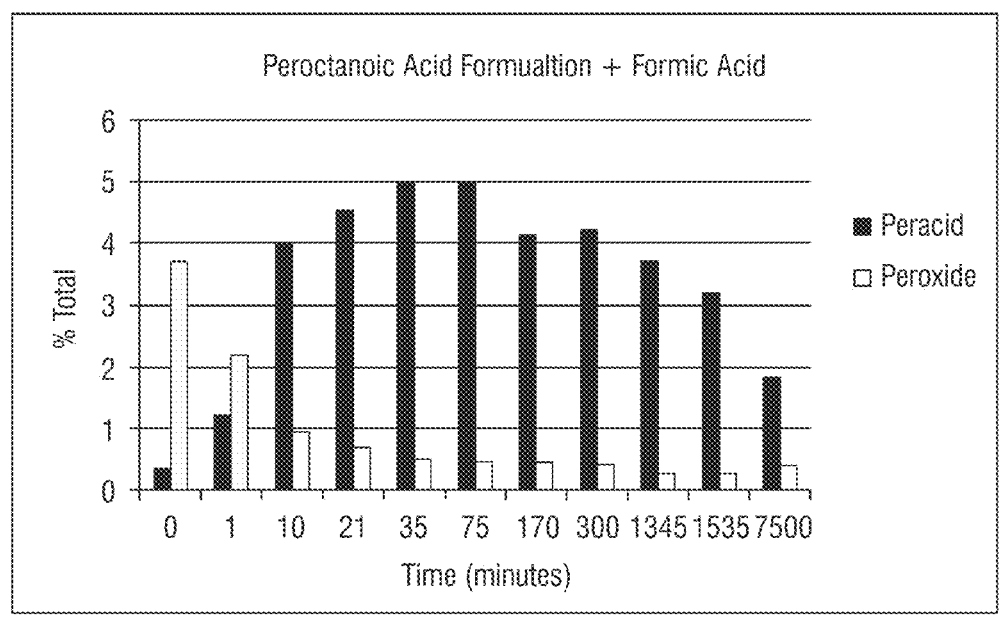
FIG. 3 illustrates addition of formic acid to a peracid system containing peroctanoic acid and hydrogen peroxide that results in a shift towards low hydrogen peroxide concentrations according to embodiments of the invention.

In this example, formic acid was added to a peroctanoic acid/hydrogen peroxide system to form a composition that contains performic acid. As shown in Table 6 below and in FIG. 3, addition of 1:1 ratio formic acid to a peroctanoic acid/peroxide system (0.75% POOA, 7.45% H202) results in reduction in the concentration of hydrogen peroxide.

TABLE 6

Reduction in the concentration of hydrogen peroxide in a peroctanoic acid/hydrogen peroxide system

| Time (min.) | Wt (g) | EP1 (ml) | EP2 (ml) | % Peracid (as POOA) | % $H_2O_2$ |
|---|---|---|---|---|---|
| 0 |  |  |  | 0.4 | 3.7 |
| 1 | 0.2606 | 1.0 | 3.5 | 1.2 | 2.2 |
| 10 | 0.2144 | 2.7 | 1.2 | 4. | 1.0 |
| 21 | 0.2885 | 4.1 | 1.2 | 4.6 | 0.7 |
| 35 | 0.3906 | 6.1 | 1.2 | 5.0 | 0.5 |
| 75 | 0.2179 | 3.4 | 0.6 | 5.0 | 0.5 |
| 170 | 0.3168 | 4.1 | 0.9 | 4.1 | 0.5 |
| 300 | 0.2344 | 3.1 | 0.6 | 4.2 | 0.4 |
| 1345 | 0.2325 | 2.7 | 0.4 | 3.7 | 0.3 |
| 1535 | 0.2300 | 2.3 | 0.4 | 3.2 | 0.3 |
| 7500 | 0.2451 | 1.4 | 0.6 | 1.8 | 0.4 |

Example 3. Influence of Hydrogen Peroxide on the Stability of Peracid in Test Systems In formulations containing hydrogen peroxide present at equilibrium concentrations, addition of formic acid reduces total peroxide concentration in the system. This increases the stability and persistence of peracetic acid in the system. Experiments were performed in a 20:80 mixture of produced water and tap water to mimic field conditions. As shown in Table 7 below, in formulations containing 10% peroxide, peracetic acid is completely consumed in 50 minutes compared to 15% of the initial hydrogen peroxide concentration (at 1080 minutes) in formulations containing 3.5% peroxide. In formulations where the addition of formic acid reduces total hydrogen peroxide to lower concentrations, the stability of peracid is greater with 34% of the total peracid added stable even after 1060 minutes.

TABLE 7

Influence of hydrogen peroxide on the stability of peracid in test systems

| POAA with 0% peroxide | | 3.5% peroxide (POAA to $H_2O_2$ ratio) | | 10% peroxide (POAA to $H_2O_2$ ratio) | |
|---|---|---|---|---|---|
| Time (min) | Normalized Residual POAA % | Time (min) | Normalized Residual POAA % | Time (min) | Normalized Residual POAA % |
| 0 | 100.0 | 0 | 100.0 | 0 | 100.0 |
| 1 | 91.0 | 5 | 59.4 | 1 | 77.9 |
| 5 | 59.4 | 10.5 | 38.4 | 5 | 33.2 |
| 9 | 50.0 | 15 | 33.9 | 10 | 23.0 |
| 35 | 31.1 | 60 | 21.2 | 50 | 0.0 |
| 1060 | 34.9 | 1080 | 15.6 | | |

Example 4. Synergistic Antimicrobial Properties

Performic acid generated in a non-equilibrium peracid formulation have been found to be synergistic in kill performance when produced on site when combined with $C_1$ to $C_{22}$ fatty acids and other peroxyacid systems. Synergy examples range from pH 0 to 12 at varied concentrations. Synergistic activity is defined as a technical effect that exceeds the addition of the cumulative performance of the materials in formulation. As shown in Table 8 below, performic acid has shown synergistic kill performance with POOA, PSOA and POA when mixed on-site when peroxide concentrations are in non-equilibrium states.

As referred to in Table 8 the following commercially-available test substances were employed: POAA (15% POAA, 10% $H_2O_2$), PAA 1 (21% peracetic, 3.5% $H_2O_2$), POOA (0.5% POOA, 6.8% $H_2O_2$).

TABLE 8

Synergistic kill performance of performic acid with POOA, PSOA and POA

| Water sample | Test substance | Concentration | Exposure time | Log reduction |
|---|---|---|---|---|
| 80% tap water | POOA | 15 ppm POOA | 5 min | 2.02 |
| 20% produced water | POOA | 30 ppm POOA | 5 min | 4.18 |
| | POOA 100 + formic acid | 15 ppm POOA + 5 ppm PFA | 5 min | 3.91 |
| | PAA 1 | 15 ppm PAA | 5 min | 2.02 |
| | PAA 1 | 30 ppm PAA | 5 min | 3.04 |
| | PAA 1 + formic acid | 15 ppm PAA + 1 ppm PFA | 5 min | 2.51 |
| | POOA | 5 ppm POOA | 5 min | 0.15 |
| | POOA | 2.5 ppm POOA | 5 min | 0.17 |
| | POOA + formic acid | 2.5 ppm POOA + 7 ppm PFA | 5 min | 5.73 |
| | Performic acid | 2 ppm PFA | 5 min | 3.01 |
| | Performic acid | 8.5 ppm PFA | 5 min | 5.69 |
| | Performic acid | 10 ppm PFA | 5 min | 5.28 |

Example 5. Exemplary Methods of Generating Performic Acid

Although not exhaustive, the following exemplary methods can be utilized for forming and enhancing the rate of formation rates of the pseudo stable reaction mixtures.

Use of Mineral Acids to Accelerate Formation of Performic Acid

Figure 4:
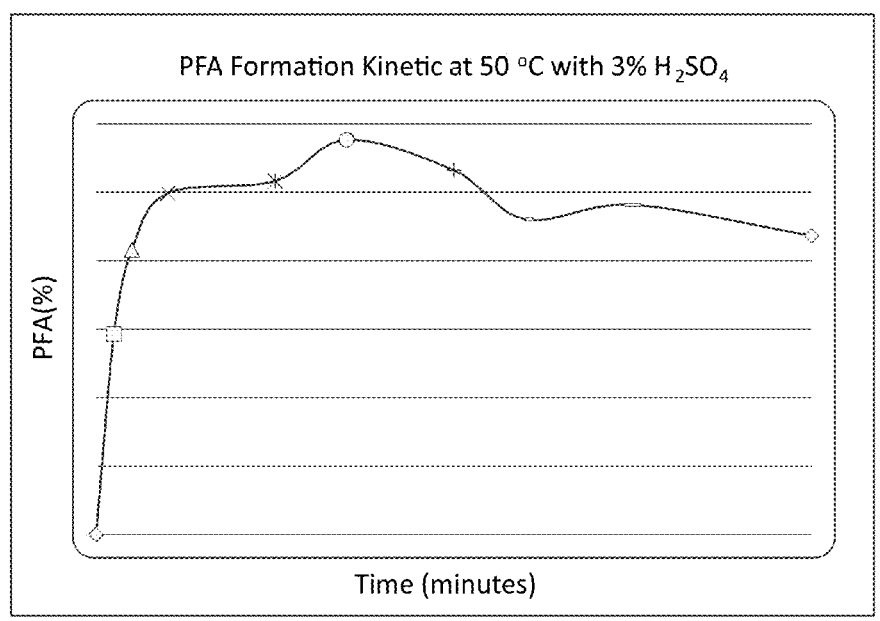
FIG. 4 illustrates that soluble mineral acids can be added to accelerate formation of performic acid according to embodiments of the invention.

As shown in FIG. 4, soluble mineral acids can be added to accelerate formation of performic acid. This can be used to compensate for the addition of a formic acid salt mixture to reach a non-equilibrium formation.

Use of Acid Exchange Resin System for Forming Performic Acid

Addition of mineral acids alters the pH of the non-equilibrium mixture.

Figure 5:
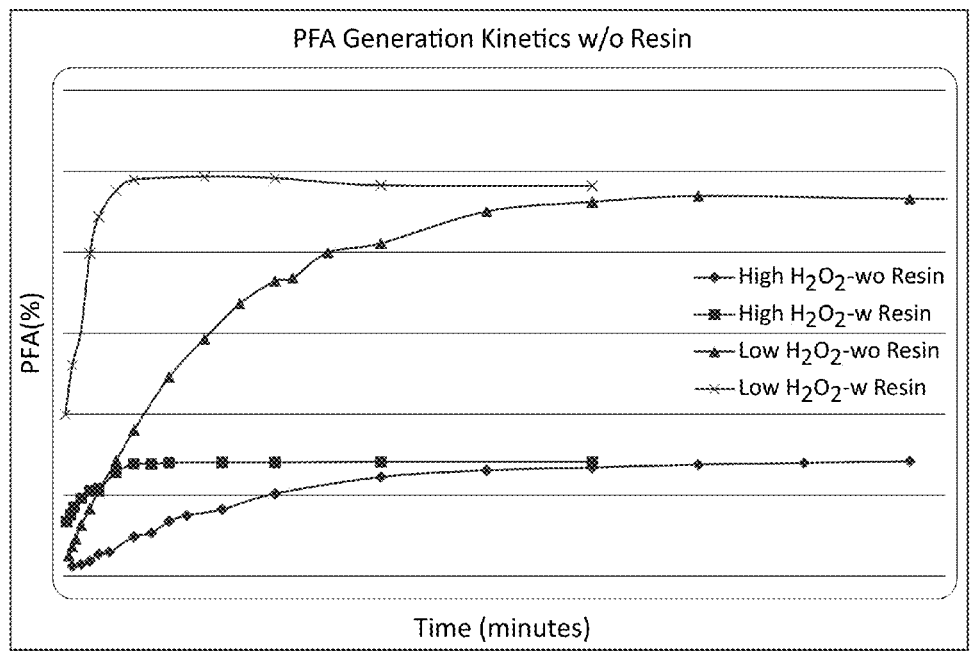
FIG. 5 illustrates formation of peroxyformic acid via an acid exchange resin system according to embodiments of the invention.

Therefore for downstream process applications that are pH sensitive, acid exchange resin systems can be used and exhibit effectiveness similar to that of acid catalysts to accelerate the formation of performic acid. As shown in Table 9 below and FIG. 5, the rate of formation of peracetic acid is increased in the presence of an acid exchange resin system compared to that without using an acid exchange resin. A commercially-available sulfonic acid exchange resin was employed (Dowex M-31) for the examples.

TABLE 9

The rate of formation of performic acid in the presence and absence of an acid exchange resin system

| Time (min) | with Dowex M-31 PFA ppm | without Dowex M-31 PFA ppm |
|---|---|---|
| 0 | 400.0 | 200.0 |
| 6 | 1670.0 | 200.0 |
| 15 | 4030.0 | 350.0 |
| 25 | 6260.0 | 500.0 |
| 35 | 11250.0 | 780.0 |
| 48 | 13470.0 | 1010.0 |
| 74 | 14800.0 | 1600.0 |
| 150 | 26600.0 | 3300.0 |
| 270 | 33700.0 | 6520.0 |
| 330 | 43000.0 | 5930.0 |

Generation of Performic Acid from Solids

Performic acid and mixed performic acids can be generated by the addition of a sodium salt of formate with a stabilized peroxide product. The kinetics of formation is limited by the solubility of sodium formate in solution. This method of peracid generation is also possible with $C_1$-$C_{22}$ peracid compositions. Table 10 below illustrates examples of the generation of performic acid by the addition of sodium formate to 10% weight/volume in formulations containing peroctanoic and peracetic acid.

TABLE 10

Exemplary generation of performic acid from sodium formate

| POOA (0.5% POOA, 6.8% $H_2O_2$) | | | POAA (15% POAA, 10% $H_2O_2$) | | | PAA 1 (21% peracetic, 3.5% $H_2O_2$) | | |
|---|---|---|---|---|---|---|---|---|
| Time (min) | % as POAA | % $H_2O_2$ | Time (min) | % as POAA | % $H_2O_2$ | Time (min) | % as POAA | % $H_2O_2$ |
| 0 | 0.7 | 6.7 | 0 | 12.4 | 9.6 | 0 | 18.6 | 3.1 |
| 2 | 1.3 | 6.4 | 1 | 13.6 | 9.4 | 1 | 19.5 | 2.4 |
| 12 | 1.5 | 5.1 | 4 | 13.9 | 8.8 | 13 | 21.8 | 2.0 |
| 40 | 1.3 | 5.0 | 26 | 13.8 | 8.8 | 31 | 24.6 | 2.0 |
| 67 | 1.2 | 4.5 | 54 | 13.5 | 7.3 | 56 | 18.2 | 1.7 |
| 117 | 0.7 | 5.0 | 106 | 13.8 | 6.6 | 116 | 18.9 | 1.8 |

Example 6. Reduction of $H_2S$ using performic acid

Figure 6:
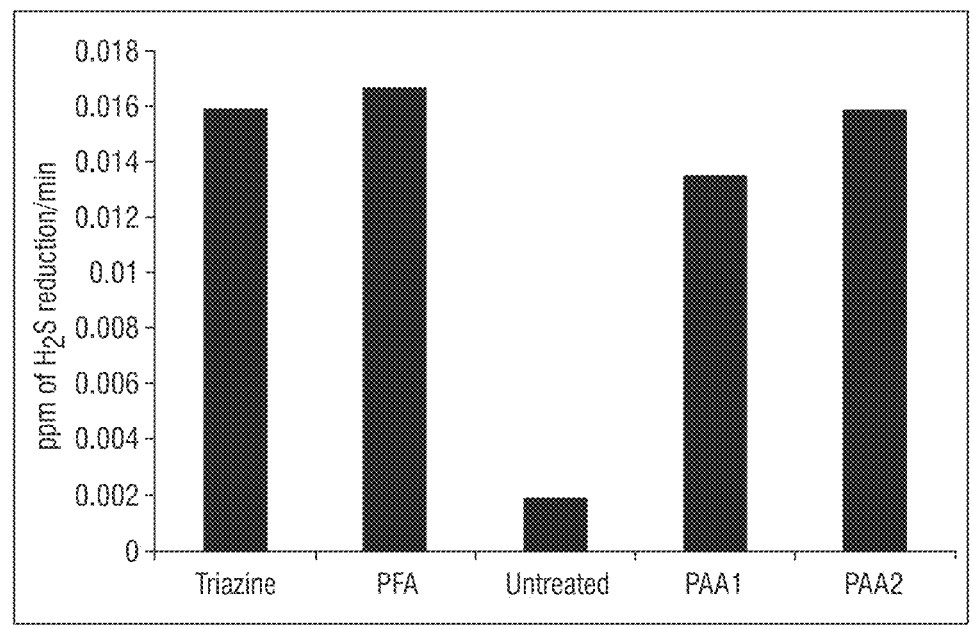
FIG. 6 illustrates reduction of $H_2S$ in the treated water source using peroxyformic acid according to embodiments of the invention.

Performance of performic acid, PAA 2 (15% peracetic acid, 10% hydrogen peroxide) and PAA 1 (21% peracetic acid, 3.5% hydrogen peroxide) were compared to triazine, a traditional $H_2S$ scavenger in produced water that was spiked with saturated $H_2S$. In a 500 ml bottle, 250 mL of $H_2S$ saturated produced water was added. The samples were allowed to equilibrate by mixing. $H_2S$ concentrations were tested using the Dräger tube method. Presence of $H_2S$ changes the color of lead acetate media in the tube to black thus providing a quantitative way of estimating $H_2S$ in the head space of each bottle. $H_2S$ was sampled at 0 minute (just prior to addition of reducers/scavengers), at 6 minutes and 60 minutes after addition. An untreated bottle was sampled at each of these time points to estimate the loss of $H_2S$ due to weathering from the bottle. For the sake of direct comparison, 10 ppm active of each chemistries were added to the reaction. Rate of $H_2S$ reduction was calculated for each of the chemistries added. As can be observed from the rate of $H_2S$ reduction in FIG. 6, performic acid performs at a rate similar to that of Triazine and comparable to that of PAA 2 (15% peracid/10% peroxide formulation). There is a small portion of $H_2S$ lost from sample bottles due to weathering.

Example 7. Reduction of Iron Sulfide in Produced Water

Iron in iron-sulfide exists as Fe(II). Upon oxidation (with peracetic acid or any other oxidant) Fe(II) becomes Fe (III). Ferrozine is a dye that specifically binds Fe(II) to produce a purple color that can be monitored at 593 nm. By quantifying the Fe(II) in the test sample and comparing untreated against peracetic acid treated samples, the effectiveness of peracetic acid or performic acid in removing iron sulfide from the water samples can be assessed. Iron (III) oxide is highly insoluble and precipitates thereby aiding removal.

In a typical test, 1 mL of saturated sodium acetate is added to 3 mL of water. This is followed by addition of 450 uL of the test sample (mixed thoroughly to ensure homogeneity). Ferrozine at approximately 20 ppm is added and the mixture incubated at room temperature for 5 min. A deep purple color will develop in samples containing Fe (II). The absorbance of the test samples at 593 are compared to calibration curve obtained from the absorbance readings of iron standards (0 to 500 ppm) prepared from iron (III) ICP standards. To measure total iron in the sample the above reaction should be reduced with freshly prepared ascorbic acid or hydroxylamine solution.

Figure 7:
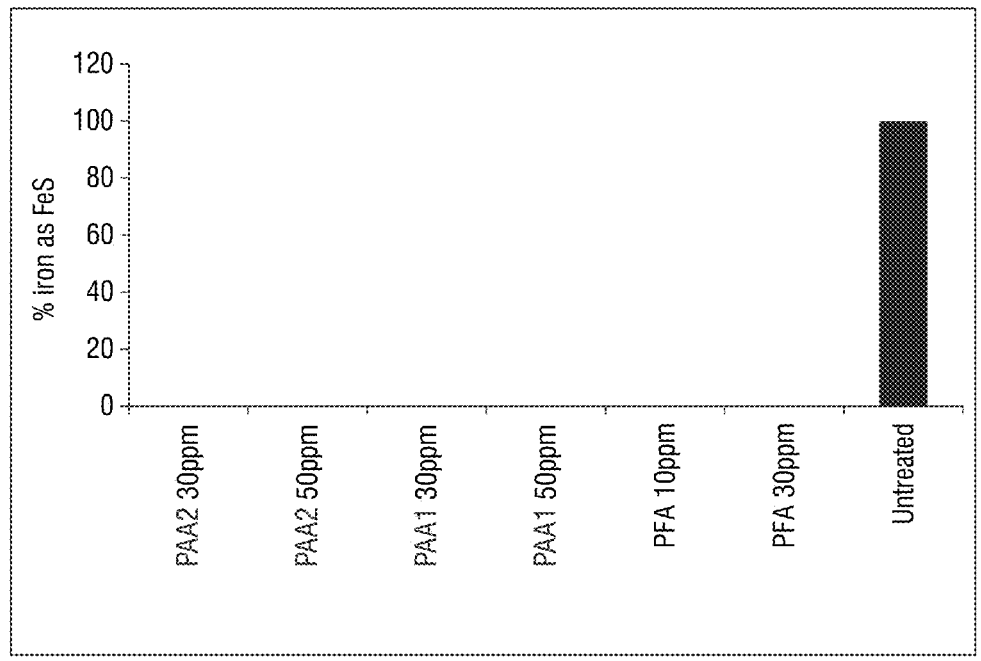
FIG. 7 illustrates reduction of iron sulfide in the treated water source using peroxyformic acid according to embodiments of the invention.

In the produced water used in this analysis, ~0.03% (300 ppm) (assumed as 100%) of iron is present as iron sulfide. After treatment with peracetic acid PAA 2, PAA 1 or performic acid for 1 hour, as shown in FIG. 7, a complete elimination of iron sulfide is observed, indicating that both peracetic and performic acids can be used for the iron-sulfide treatments in produced water.

Example 8. Water Clarification

One of the potential benefits of oxidizers in treating produced waters is its ability to clarify water by oxidizing contaminants. We evaluated the performance of PAA 2, PAA 1 and performic acids in its ability to improve clarity of water. For water clarification, 100 ppm of coagulant was added to produced water. This mixture was allowed to mix for 2 min. This was followed by the addition of 30 ppm active PAA from PAA 2, PAA 1 and 10 ppm active of performic acid respectively. After oxidation by these peracids flocculants 71301 at 2 ppm concentration was used. The samples were allowed to separate for 15-20 minutes at room temperature. Five (5) mL of sample was carefully taken from the untreated and peracid treated samples and % transmittance was measured. Clearer the water higher the transmittance value.

Figure 8:
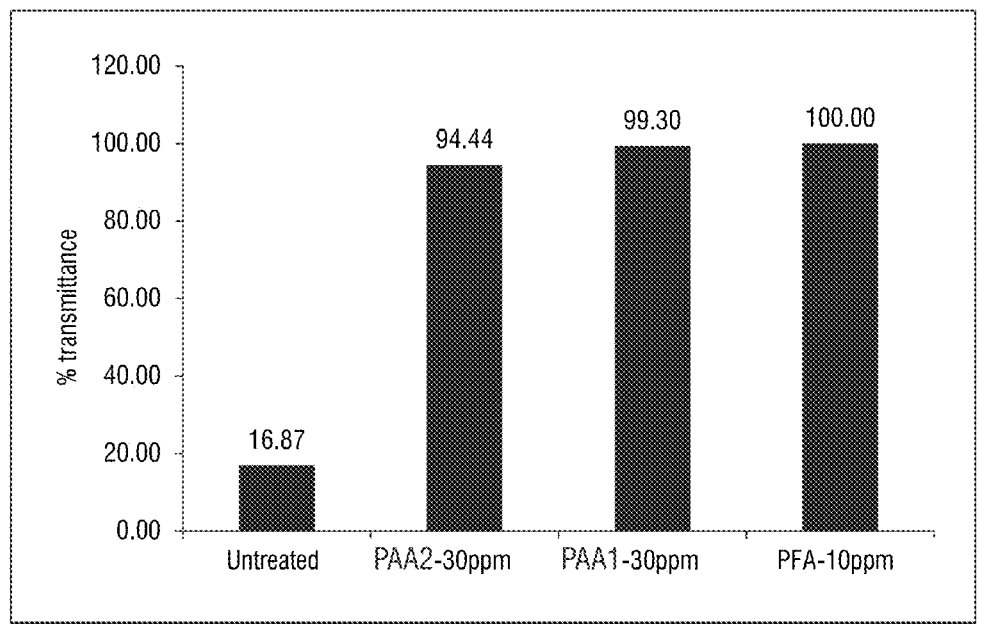
FIG. 8 illustrates improving clarity of the treated water source using peroxyformic acid as measured by % transmittance according to embodiments of the invention.
Figure 9:
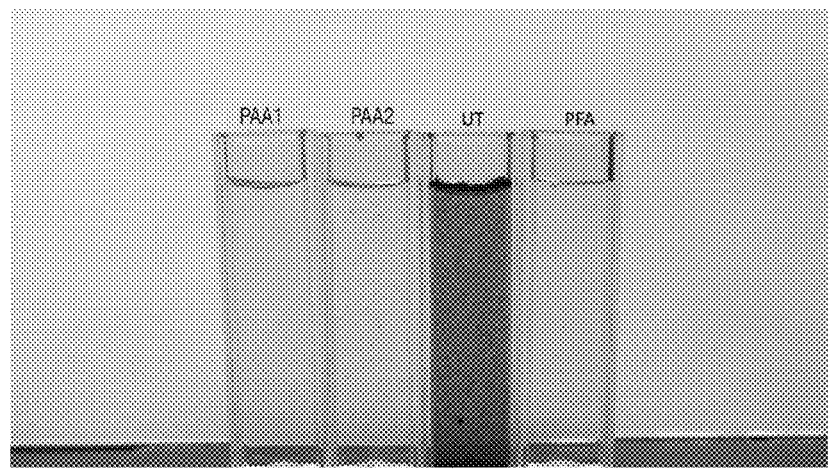
FIG. 9 illustrates improving clarity of the treated water source using peroxyformic acid as shown in the pictures before and after peroxyformic acid treatment according to embodiments of the invention.

As shown in FIG. 8, performic acid at 10 ppm active provides clarity that is comparable to PAA 1 (21% peracid/3.5% peroxide) at 30 ppm active. Untreated water however does not transmit light. Pictures of pre and post water clarification are also shown in FIG. 9.

Example 9. Dissolved Oxygen

The purpose of this study is to determine increase in dissolved oxygen in produced-water upon treatment with PAA 2, PAA 1, and PFA. When dosed into produced water at or below demand concentrations, both chemistries do not significantly alter dissolved oxygen content. However, upon addition of excess of PAA 2 and PAA 1 beyond consumption rate, there is an increase in the total dissolved oxygen in the system. However, addition of PFA decreases the total oxygen content in the samples.

Fifty (50) mL of produced water was treated with PAA 2 or PAA 1. Dosage was based on demand concentration determined by performing a consumption study on the sample. All the experiments were performed at the same temperature (20.8 to 21.1° C.) and mixing rate. After the addition of peracetic acid to the appropriate dosage, the sample was allowed to mix for 1 minute. SPER scientific dissolved oxygen probe was used for all experiments. Prior to use, the probe was calibrated and the ambient oxygen reading was 20.9%. The probe was allowed to sit in the solution for 30 seconds during which the data were recorded. The values reported in the tables below are the 'stabilized' value after 30 seconds of equilibration of the probe in the solution. For each sample, dissolved oxygen prior to treatment was determined. This can be used as the baseline. The values indicated in the table are an average of two independent experiments but using the same produced water.

Example 10. Treatment of Produced Water with PAA 2

Based on the consumption study, the demand for PAA 2 was determined to be 950 ppm product (142.6 ppm active) as shown in Table 11. The baseline 02 measurement was determined to be 9.0 after equilibrating the produced water under ambient conditions. Any increase in the dissolved oxygen from this baseline value can therefore be assumed to be caused by peracetic acid or peroxide components of PAA 2. Subtracting the baseline any the increase in dissolved oxygen is shown in Table 12.

TABLE 11

Concentration (ppm) of oxygen detected in PAA 2 treated produced water

| Demand | ppm of PAA 2 | ppm of PAA | ppm of $H_2O_2$ | Expt1 ppm $O_2$ | Expt2 ppm $O_2$ | avg ppm $O_2$ | stddev ppm |
|---|---|---|---|---|---|---|---|
| 0.0 | 0.0 | 0.0 | 0.0 | 9.0 | 8.9 | 9.0 | 0.1 |
| 0.5 | 475.0 | 71.3 | 47.5 | 9.0 | 8.9 | 8.9 | 0.1 |
| 1.0 | 950.0 | 142.6 | 95.0 | 9.6 | 9.7 | 9.7 | 0.1 |
| 1.5 | 1425.0 | 214.0 | 142.5 | 11.1 | 10.6 | 10.8 | 0.3 |

TABLE 11-continued

Concentration (ppm) of oxygen detected in PAA 2 treated produced water

| Demand | ppm of PAA 2 | ppm of PAA | ppm of H$_2$O$_2$ | Expt1 ppm O$_2$ | Expt2 ppm O$_2$ | avg ppm O$_2$ | stddev ppm |
|---|---|---|---|---|---|---|---|
| 2.0 | 1900.0 | 285.3 | 190.0 | 11.3 | 10.5 | 10.9 | 0.6 |
| 4.0 | 3800.0 | 570.6 | 380.0 | 14.0 | 14.2 | 14.1 | 0.1 |
| 8.0 | 7600.0 | 1141.1 | 760.0 | 21.0 | 21.5 | 21.0 | 0.4 |

TABLE 12

Increase from baseline of Oxygen (in ppm) of PAA 2 treated produced water

| Demand | ppm of PAA 2 | ppm of PAA | ppm of H$_2$O$_2$ | Expt1 ppm O$_2$ | Expt2 ppm O$_2$ | avg ppm O$_2$ | stddev ppm |
|---|---|---|---|---|---|---|---|
| 0.0 | 0.0 | 0.0 | 0.0 | 0.0 | 0.0 | 0.0 | 0.0 |
| 0.5 | 475.0 | 71.3 | 47.5 | −0.1 | −0.1 | −0.05 | 0.0 |
| 1.0 | 950.0 | 142.6 | 95.0 | 0.6 | 0.8 | 0.7 | 0.1 |
| 1.5 | 1425.0 | 214.0 | 142.5 | 2.1 | 1.7 | 1.9 | 0.3 |
| 2.0 | 1900.0 | 285.3 | 190.0 | 2.3 | 1.6 | 2.0 | 0.5 |
| 4.0 | 3800.0 | 570.6 | 380.0 | 5.0 | 5.3 | 5.0 | 0.2 |
| 8.0 | 7600.0 | 1141.1 | 760.0 | 12.0 | 12.6 | 12.3 | 0.4 |

The total dissolved oxygen increases with increase dosage of PAA2. At 50% demand dosage, the increase in dissolved oxygen is insignificant. However at 100% demand and beyond an increase in total dissolved oxygen beyond the baseline can be measured. The small increase in dissolved oxygen may be due to an error in the estimation of the demand concentration.

Example 11. Treatment of Produced Water with PAA 1

Based on the consumption study the demand for PAA 1 was determined to be 825 ppm as shown in Table 13 below. The baseline O2 measurement was determined to be between 8.0 and 9.0 after equilibrating the produced water under ambient conditions. Any increase in the dissolved oxygen from this baseline value can therefore be assumed to be caused by peracetic acid or peroxide component of PAA 1. Subtracting the baseline ppm, the increase in dissolved oxygen is indicated in Table 14.

TABLE 13

Concentration (ppm) of oxygen detected in PAA 1 treated produced water

| Demand | ppm of PAA 1 | ppm of PAA | ppm of H$_2$O$_2$ | Expt1 ppm O$_2$ | Expt2 ppm O$_2$ | avg ppm O$_2$ | stddev ppm |
|---|---|---|---|---|---|---|---|
| 0.0 | 0.0 | 0.0 | 0.0 | 9.0 | 8.0 | 8.5 | 0.7 |
| 0.5 | 412.5 | 82.5 | 12.4 | 8.8 | 8.0 | 8.4 | 0.6 |
| 1.0 | 825.0 | 165.0 | 24.8 | 9.0 | 7.9 | 8.4 | 0.8 |
| 1.5 | 1237.5 | 247.5 | 37.2 | 9.0 | 8.3 | 8.6 | 0.5 |
| 2.0 | 1650.0 | 330.0 | 49.5 | 9.7 | 9.2 | 9.4 | 0.4 |
| 4.0 | 3300.0 | 660.0 | 99.1 | 13.8 | 14.0 | 13.9 | 0.1 |
| 8.0 | 6600.0 | 1320.0 | 198.2 | 19.0 | 19.2 | 19.1 | 0.1 |

TABLE 14

Increase from baseline of Oxygen (in ppm) of PAA 1 treated produced water

| Demand | ppm of PAA 1 | ppm of PAA | ppm of H$_2$O$_2$ | Expt1 ppm O$_2$ | Expt2 ppm O$_2$ | avg ppm O$_2$ | stddev ppm |
|---|---|---|---|---|---|---|---|
| 0.0 | 0.0 | 0.0 | 0.0 | 0.0 | 0.0 | 0.0 | 0.0 |
| 0.5 | 412.5 | 82.5 | 12.4 | −0.2 | −0.1 | −0.1 | 0.1 |
| 1.0 | 825.0 | 165.0 | 24.8 | 0.0 | −0.2 | −0.1 | 0.1 |
| 1.5 | 1237.5 | 247.5 | 37.2 | 0.0 | 0.3 | 0.1 | 0.2 |
| 2.0 | 1650.0 | 330.0 | 49.5 | 0.7 | 1.2 | 0.9 | 0.4 |
| 4.0 | 3300.0 | 660.0 | 99.1 | 4.8 | 6.0 | 5.4 | 0.8 |
| 8.0 | 6600.0 | 1320.0 | 198.2 | 10.0 | 11.2 | 10.6 | 0.9 |

At and below 100% demand, the total dissolved oxygen does not increase. As was seen with PAA 2 there is a dosage dependent increase in dissolved oxygen suggesting that both peracetic acid and peroxide contribute to the total dissolved oxygen in solution.

Example 12. Treatment of Produced Water with Performic Acid

Concentration (ppm) of oxygen detected in performic treated produced water is shown in Table 15 below. The baseline O2 measurement was determined to be between 8.0 and 9.0 after equilibrating the produced water under ambient conditions. Subtracting the baseline ppm, the increase in dissolved oxygen is indicated in Table 16 below.

TABLE 15

Concentration (ppm) of oxygen detected in performic treated produced water

| ppm of prod | ppm of PFA | ppm of H$_2$O$_2$ | Expt1 ppm O$_2$ | Expt2 ppm O$_2$ | avg ppm O$_2$ | stddev ppm |
|---|---|---|---|---|---|---|
| 0.0 | 0.0 | 0.0 | 8.0 | 8.6 | 8.3 | 0.4 |
| 500.0 | 29.0 | 0.0 | 5.4 | 5.4 | 5.4 | 0.0 |
| 1000.0 | 58.0 | 0.0 | 6.2 | 4.9 | 5.5 | 0.9 |
| 1500.0 | 87.0 | 0.0 | 6.5 | 5.2 | 5.8 | 0.9 |
| 2000.0 | 116.0 | 0.0 | 6.3 | 5.2 | 5.8 | 0.8 |
| 4000.0 | 232.0 | 0.0 | 5.8 | 4.7 | 5.3 | 0.8 |
| 8000.0 | 464.0 | 0.0 | 6.5 | 5.1 | 5.8 | 1.0 |

TABLE 16

Increase from baseline of oxygen (in ppm) of performic treated produced water

| ppm of Prod | ppm of PFA | ppm of H$_2$O$_2$ | Expt1 ppm O$_2$ | Expt2 ppm O$_2$ | avg ppm O$_2$ | stddev ppm |
|---|---|---|---|---|---|---|
| 0.0 | 0.0 | 0.0 | 0 | 0 | 0 | 0 |
| 500.0 | 29.0 | 0.0 | −2.6 | −3.2 | −2.9 | 0.4 |
| 1000.0 | 58.0 | 0.0 | −1.8 | −3.7 | −2.8 | 1.3 |
| 1500.0 | 87.0 | 0.0 | −1.5 | −3.4 | −2.5 | 1.3 |
| 2000.0 | 116.0 | 0.0 | −1.7 | −3.4 | −2.6 | 1.2 |
| 4000.0 | 232.0 | 0.0 | −2.2 | −3.9 | −3.1 | 1.2 |
| 8000.0 | 464.0 | 0.0 | −1.5 | −3.5 | −2.5 | 1.4 |

Figure 10:
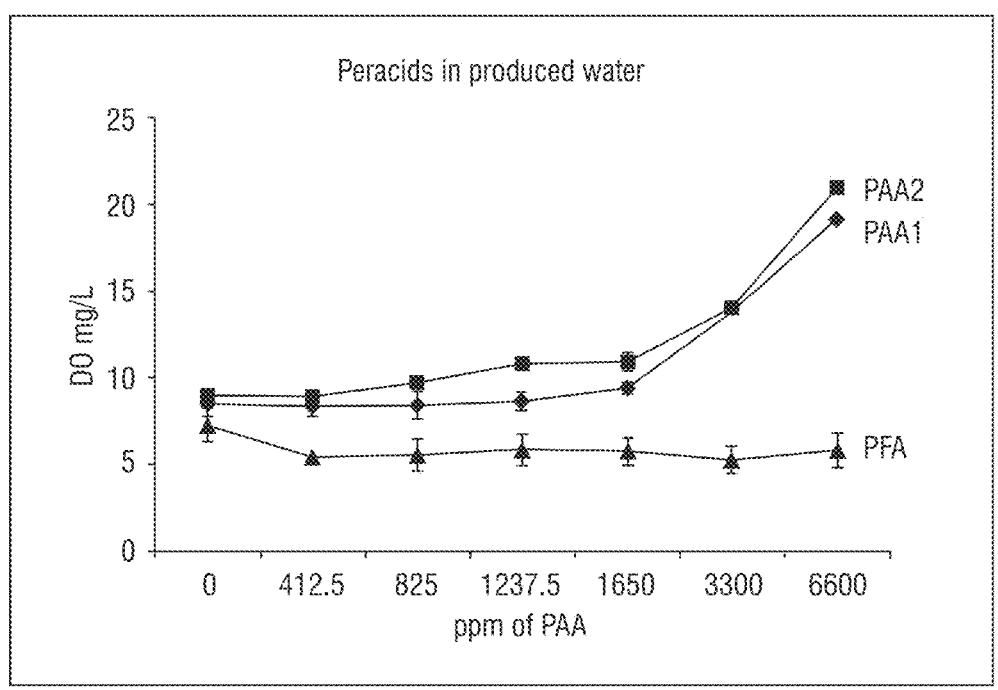
FIG. 10 illustrates reduction of the total dissolved oxygen in the treated water source using peroxyformic acid as measured by $O_2$ production in the treated water source according to embodiments of the invention.
Figure 11:
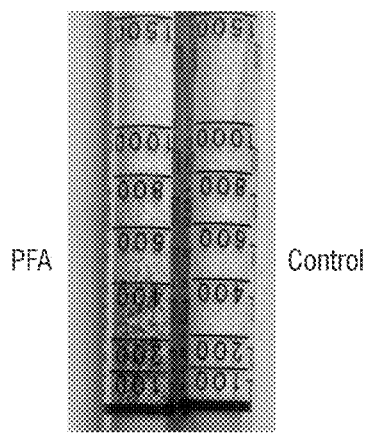
FIG. 11 illustrates reduction of the total dissolved oxygen in the treated water source (FIG. 10) using peroxyformic acid as shown by the darker color that indicates generation of $CO_2$.

Performic acid addition decreased the total dissolved oxygen in the samples. This is in stark contrast to that observed in samples treated with peracetic acid as shown in FIG. 10. Without wishing to be bound by any particular theory, one possible explanation to the decrease in total dissolved oxygen is that the breakdown products of performic acid formulation include CO$_2$ that displaces oxygen from the produced water samples. To test this hypothesis, $CO_2$ Drager tubes were obtained and headspace of the sample that was treated with performic acid analyzed. As can be seen from FIG. 11 wherein the darkened color as shown in grey scale (purple color during testing) indicates generation of $CO_2$, addition of performic acid to produced water produces $CO_2$ suggesting that the breakdown products of performic acid produce $CO_2$ instead of oxygen like that observed in peracetic acid. This feature may make this product useful for application that is sensitive to the presence of oxygen, e.g., offshore applications.

Example 13. Comparison of Corrosion Profiles PAA 2, PAA 1 and Performic Acid on Carbon Steel Corrosion rate in MPY (millimeters per year) were determined for carbon steel coupons in produced water treated with peracids. Prior to treatment, consumption of peracids for complete oxidation of iron-sulfide, microbial kill etc. was determined for each composition. In a bubble cell test, carbon steel coupons were submerged in produced water that was purged with $CO_2$. This was done for 3-4 hours to establish a baseline. After the baseline corrosion rate was stabilized, PAA 2, PAA 1 or performic acid was added to produced water at the previously determined demand concentration. Corrosion rate of the coupon in peracid treated produced water were monitored for 19 hours. The rates of corrosion are shown In FIG. 12.

Figure 12:
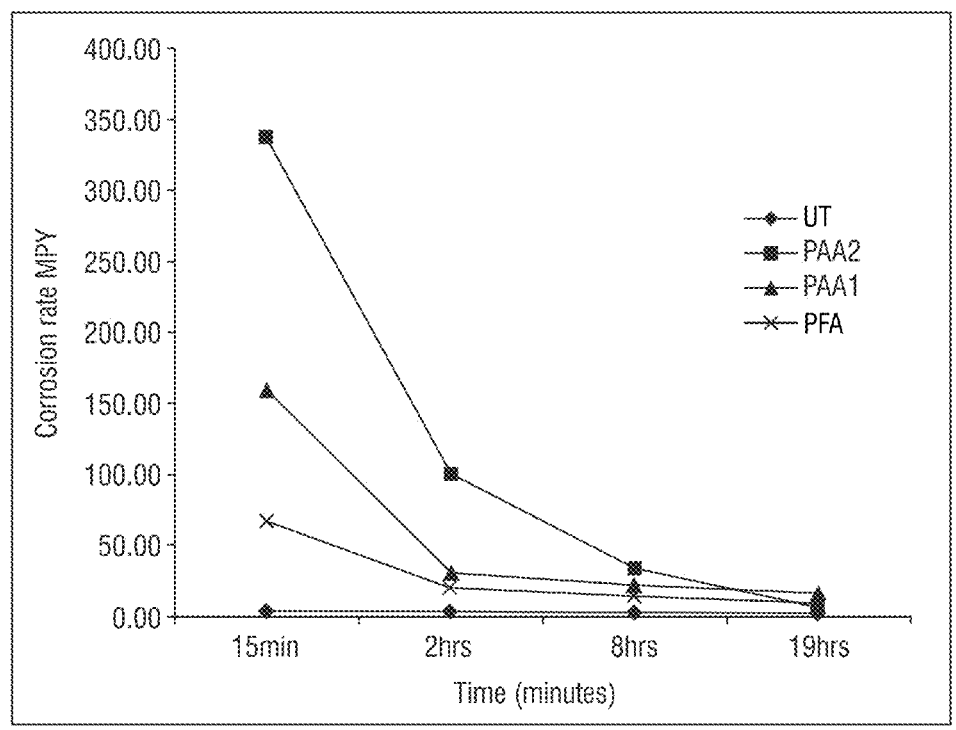
FIG. 12 illustrates reduction of corrosion in the treated water source using peroxyformic acid according to embodiments of the invention.

As shown In FIG. 12, PAA 2 has the highest corrosion rate, followed by PAA 1. Among the three peracid composition tested, performic acid exhibits the lowest corrosion rate. Bubble cell testing is not a completely closed system. In addition, iron in the carbon steel coupons is oxidized to iron oxide or iron carbonate both of which lead to passivation of the electrode over time thus leading to a decreased (observed) corrosion rate in system. However in field systems any carbon steel coupons will encounter corrosion rates that are highest observed in a particular treatment.

PAA 2 and PAA 1 are peracetic acid/hydrogen peroxide compositions. A lower ratio of peracetic acid/hydrogen peroxide in PAA 2 (ratio of 1.5) shows significantly higher corrosion rate than PAA 1 (Peracetic acid/peroxide ratio of about 7). In performic acid system, there was no observed hydrogen peroxide. Therefore the corrosion rate because of oxygen in the system is negligible. This observation alone provides a significant advantage for performic acid over peracetic acid systems in decreasing the total corrosion rates in treatment systems.

Example 14. Formation of High Peracid to Hydrogen Peroxide Ratio in Reactions Less than 2 Hours is Unique to Equilibrium Between Formic Acid and Hydrogen Peroxide To determine if formation of a high peracid to hydrogen peroxide ratio is unique to the equilibrium reaction between formic acid and hydrogen peroxide, control experiments were performed using the same formulation but acetic acid instead of formic acid in a control reaction. The Tables 17 and 18 below list the percentage of peformic or peracetic acids and residual hydrogen peroxide that were detected.

TABLE 17

Performic acid formation from a mixture of formic acid and hydrogen peroxide

| Time (min.) | Wt (g) | EP1 (ml) | EP2 (ml) | % PFA | % $H_2O_2$ |
|---|---|---|---|---|---|
| 0 | | | | 0.0 | 0.0 |
| 5 | 1.14 | 6.2 | 15.0 | 1.7 | 1.3 |
| 14 | 0.46 | 6.1 | 6.3 | 4.2 | 0.1 |
| 25 | 0.48 | 7.5 | 7.5 | 5.0 | 0.0 |
| 48 | 0.32 | 5.0 | 5.0 | 5.0 | 0.0 |

TABLE 18

Peracetic acid formation from a mixture of acetic acid and hydrogen peroxide

| Time (min.) | Wt (g) | EP1 (ml) | EP2 (ml) | % POAA | % $H_2O_2$ |
|---|---|---|---|---|---|
| 0 | | | | 0.0 | 0.0 |
| 6 | 0.8 | 0.2 | 10.6 | 0.1 | 2.3 |
| 23 | 1.0 | 0.4 | 14.0 | 0.2 | 2.3 |
| 89 | 0.7 | 0.1 | 8.9 | 0.1 | 2.1 |

Example 15. Use of Corrosion Inhibitor(s)

Performic acid introduces less corrosion to the carbon steel systems than peracetic formulations. Nevertheless, even the lower, acid corrosion, introduced by performic acid (PFA) can be mitigated by using one of the exemplary corrosion inhibitor compounds listed in Table 19 below. These compounds can be used either alone or as a mixture. The exemplary phosphate esters, diacids, quat amines, imidazoline, alkyl pyridine, phosphonium salts and derivatives of the above mentioned class of compounds can be added in the formulation from about 1 ppm to about 50,000 ppm either in the formulation components (e.g., formic acid, peroxide) or can be added separately prior to PFA treatment, with PFA treatment or post PFA treatments. Some of these compounds also exhibit synergy in the total kill of microbes with performic acid. Addition of the corrosion inhibitor(s) can be performed either pre, with or post treatment of waters with performic acid. In addition, the listed compounds can also be mixed into one of the reagents used in the production of performic acid.

TABLE 19

Exemplary class of compounds and representative raw materials used for mitigation of corrosion caused by performic acid

| Corrosion Inhibitor | Formulation Active(s) | Class of compound |
|---|---|---|
| CI 1 | Benzyl-dimethyl-dodecyl-ammonium chloride<br>Benzyl-dimethyl-tetradecyl-ammonium chloride<br>Benzyl-dimethyl-hexadecyl-ammonium chloride<br>Benzyl-dimethyl-octadecyl-ammonium chloride | Quat. Amine |
| CI 2 | Benzyl-dimethyl-dodecyl-ammonium chloride<br>Benzyl-dimethyl-tetradecyl-ammonium chloride<br>Benzyl-dimethyl-hexadecyl-ammonium chloride<br>Benzyl-dimethyl-octadecyl-ammonium chloride | Quat. Amine |

TABLE 19-continued

Exemplary class of compounds and representative raw materials used for mitigation of corrosion caused by performic acid

| Corrosion Inhibitor | Formulation Active(s) | Class of compound |
|---|---|---|
| CI 3 | Tall oil, diethylenetriamine imidazoline | Imidazoline |
| CI 4 | Fatty acids, tall-oil, reaction products with n-(2-aminoethyl)-1,2-ethanediamine & 2-propenoic acid | Imidazoline |
| CI 5 | Ethoxylated-C11-14-iso-, C13-rich, phosphates | Phosphate Ester |
| CI 6 | Ethoxylated branched nonylphenol<br>Ethoxylated branched nonylphenol, phosphates | Phosphate Ester |
| CI 7 | Trimeric c18 unsat fatty acid | Diacids |
| CI 8 | Tar bases, quinoline derivs., benzyl chloride-quaternized | Alkyl pyridine; Haloalkyl heteropolycycle salt |
| CI 9 | Benzyl chloride<br>Benzyl-dimethyl-dodecyl-ammonium chloride<br>Benzyl-dimethyl-tetradecyl-ammonium chloride<br>Benzyl-dimethyl-hexadecyl-ammonium chloride<br>Benzyl-dimethyl-octadecyl-ammonium chloride | Benzyl, Alkylquat with scale |
| CI 10 | Tributyl Tetradecyl Phosphonium Chloride | phosphonium chloride |
| CI 11 | Diddecyl dimethyl ammonium carbonate/bicarbonate | Ammonium chloride |
| CI A | Quaternary ammonium compound<br>Substituted aromatic amine<br>Fatty acid-amine derivative | C4-C16 Alcohols, Aldehydes, Esters |
| CI B | Quaternary ammonium compound | Quat. |
| CI C | Quaternary ammonium compound 2-Mercaptoethanol 60-24-2 | Quat. |
| CI D | Quaternary Ammonium Chloride<br>Fatty acid-amine condensate<br>Quaternary ammonium compound<br>Oxyalkylated Fatty Amine<br>Isopropanol 67-63-0<br>2-Butoxyethanol 111-76-2<br>Fatty acid-amine derivative<br>Cyclic amine derivatives, acetate<br>Pyridine, Alkyl Derivs., Acetates | Quat. |

Figure 13:
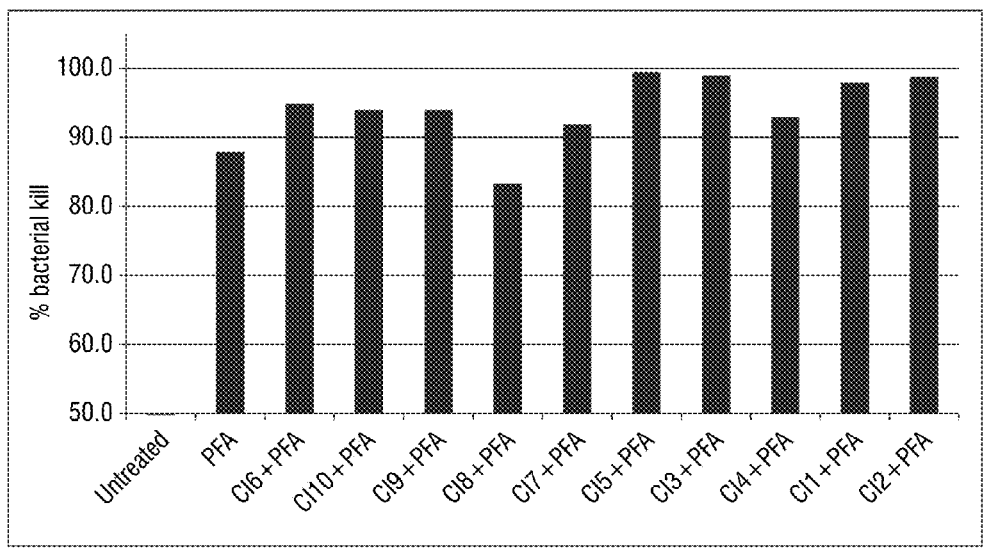
FIG. 13 illustrates synergy in microbial kill shown as % dead for untreated, performic acid treated (5 ppm active) and performic acid (5 ppm active) in addition to the compounds (50 ppm product) listed in Table 20 according to embodiments of the invention.

Microbial efficacy of PFA alone (5 ppm active) or PFA (5 ppm active) in conjunction with the compounds (50 ppm product) listed in the Table 20 below and in FIG. 13 were tested by measuring the ATP concentration in the untreated and treated produced water samples (using AccuCount technology). Reductions in bacterial numbers were tabulated as % kill for each experiment. The results are represented in FIG. 13 and in Table 20. As can be seen from the results, with the exception of CI 8, an alky pyridine compound, all other compounds tested show an increase in bacterial kill indicating that there is a synergy in bacterial kill for PFA when used in conjunction with compounds commonly used for corrosion mitigation.

TABLE 20

Percentage kill of microorganisms in produced water prior to and after treatment with Performic acid

| Treatment | % Kill |
|---|---|
| Untreated | 0.0 |
| PFA | 87.9 |
| CI 6 + PFA | 94.8 |
| CI 10 + PFA | 94.0 |
| CI 9 + PFA | 94.0 |
| CI 8 + PFA | 83.3 |
| CI 7 + PFA | 91.9 |
| CI 5 + PFA | 99.4 |
| CI 3 + PFA | 99.0 |
| CI 4 + PFA | 92.9 |
| CI 1 + PFA | 97.9 |
| CI 2 + PFA | 98.8 |

In addition to bacterial kill, corrosion profiles of PFA and PFA with corrosion inhibitors were tested on a carbon steel coupon (C1018) in a bubble cell apparatus. The results were monitored continuously and corrosion rates at 2, 8 and 19 hours are shown in Table 21 below. PFA was added to all the tests at a concentration of 20 ppm active. Except for the control cell (PFA), corrosion inhibitors at 50 ppm product concentration was added to all the other cells. Corrosion rates were monitored continuously. As indicated in Table 21, corrosion rate on carbon steel coupons increase from a baseline of 32.3 MPY to 236.3 MPY by 2 hours post addition of PFA. With the exceptions of CI 7, CI 5, CI 3, CI 6; all other compounds decrease the rate of corrosion caused by PFA.

TABLE 21

Corrosion caused by performic acid can be mitigated by the addition of the compounds listed in Table 20.

|  | baseline (MPY) | After dosing | | |
|---|---|---|---|---|
|  |  | 2 hrs (MPY) | 8 hrs (MPY) | 19 hrs (MPY) |
| PFA | 32.3 | 236.2 | 243.1 | 419.4 |
| CI 6 + PFA | 16.8 | 25.7 | 32.0 | 31.5 |
| CI 10 + PFA | 41.9 | 19.8 | 14.0 | 14.4 |
| CI 9 + PFA | 58.4 | 5.6 | 4.8 | 3.7 |
| CI 8 + PFA | 90.2 | 29.5 | 51.3 | 89.8 |
| CI 7 + PFA | 19.5 | 249.6 | 381.2 | 553.6 |
| CI 5 + PFA | 61.7 | 77.3 | 151.0 | 147.2 |
| CI 3 + PFA | 27.3 | 48.0 | 82.3 | 84.8 |
| CI 4 + PFA | 31.7 | 17.8 | 19.5 | 4.8 |
| CI 1 + PFA | 44.6 | 18.1 | 11.1 | 10.3 |
| CI 2 + PFA | 114.0 | 86.7 | 33.5 | 21.9 |

MPY in Table 21 above indicates the rate of corrosion (millimeters per year). Higher MPYs indicate increased corrosion. It can be observed from the Table 21 above that there is a significant reduction in the overall MPY after 2, 8 and 19 hours after the addition of some of the corrosion inhibitors.

Example 16. Exemplary Methods of Generating Peroxyformic Acid

Figure 14:
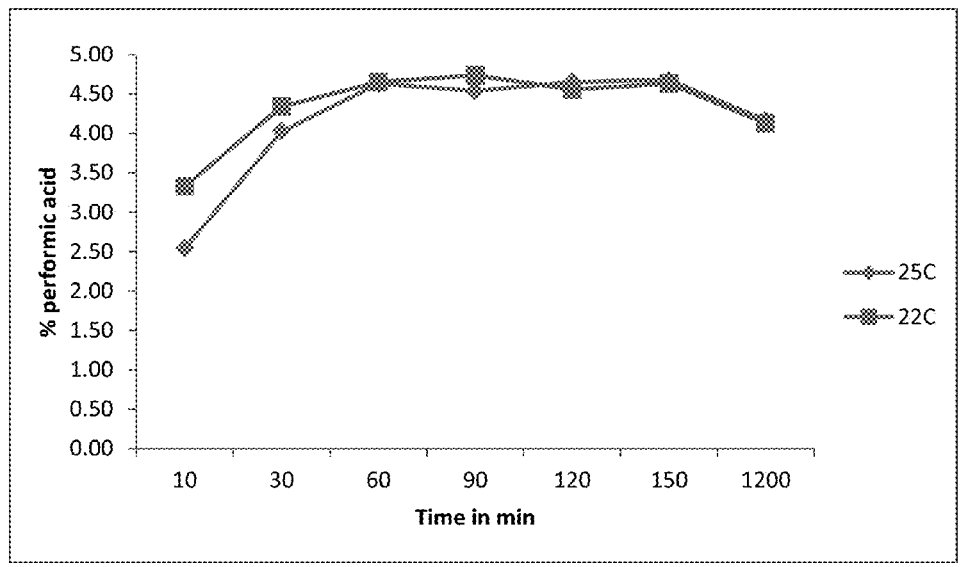
FIG. 14 illustrates peroxyformic acid generation at room temperature using a stabilizing agent according to embodiments of the invention.

Peroxyformic acid generation at room temperature was evaluated using a stabilizing agent as shown in Table 22 and FIG. 14.

TABLE 22

Peroxyformic acid with a stabilizing agent and without a catalyst.

|  | weight % | |
|---|---|---|
| Formic acid (98%) | 20.0 | 92.17 |
| Dipicolinic acid | 0.0025 | 0.01 |
| $H_2O_2$ (35%) | 1.7 | 7.83 |
| Total | 21.7 | 100 |
| Performic acid |  | 4.63 |
| peroxide |  | 0.12 |

Figure 15:
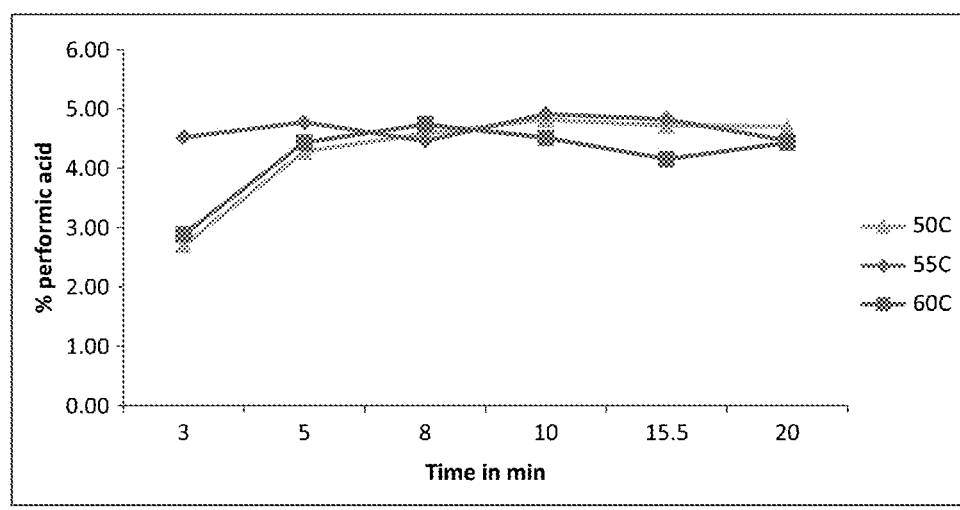
FIG. 15 illustrates the impact of temperature on the kinetics of peroxyformic acid generation according to embodiments of the invention.

Increase in temperatures resulted in a further increase in the kinetics of formation of performic acid utilizing the formulation of Table 22 as shown in FIG. 15.

Figure 16:
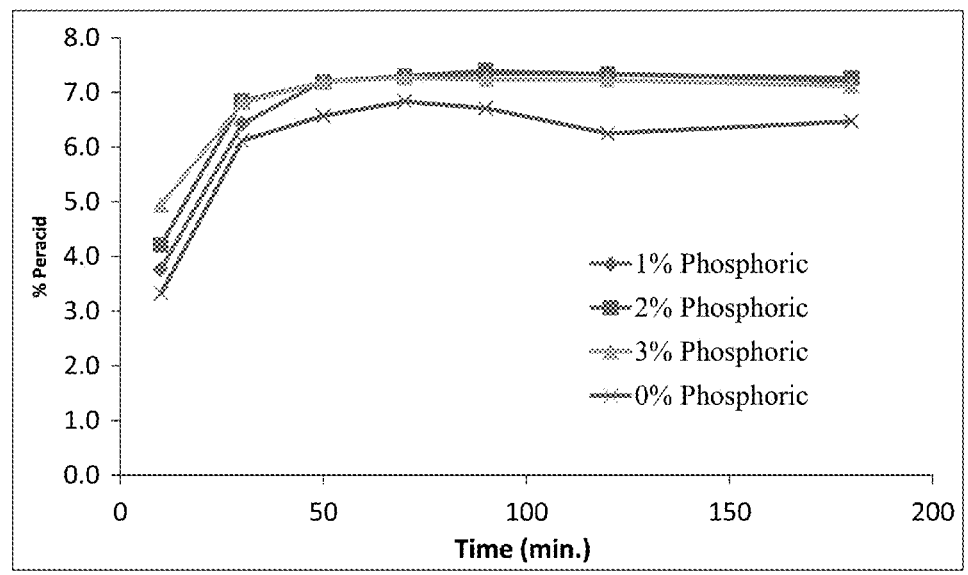
FIG. 16 illustrates peroxyformic acid generation using a catalyst according to embodiments of the invention.

Example 17. Optimization of Generating Peroxyformic Acid Using Low Hydrogen Peroxide Formulations Peroxyformic acid generation under ambient temperature was evaluated using a catalyst (Dequest, MSA or phosphoric acid at different concentrations) as shown in Table 23 and FIG. 16.

TABLE 23

| Composition | Low $H_2O_2$ PFA-1 (original) % | Low $H_2O_2$ PFA-2 % |
|---|---|---|
| Formic acid (98%) | 90.17 | 85.67 |
| $H_2O_2$ (35%) | 7.83 | 12.83 |
| $H_2O_2$ (50%) | 0 | 0 |

TABLE 23-continued

| Composition | Low $H_2O_2$ PFA-1 (original) % | Low $H_2O_2$ PFA-2 % |
|---|---|---|
| MSA (70%) | 0.0 | 1.5 |
| $H_3PO_4$ (75%) |  |  |
| Total | 100 | 100 |
| PFA % | 4.88 | 7.50 |
| $H_2O_2$ % | 0.13 | 0.20 |

Example 18. Optimization of Generating Peroxyformic Acid Using Catalysts

Figure 17:
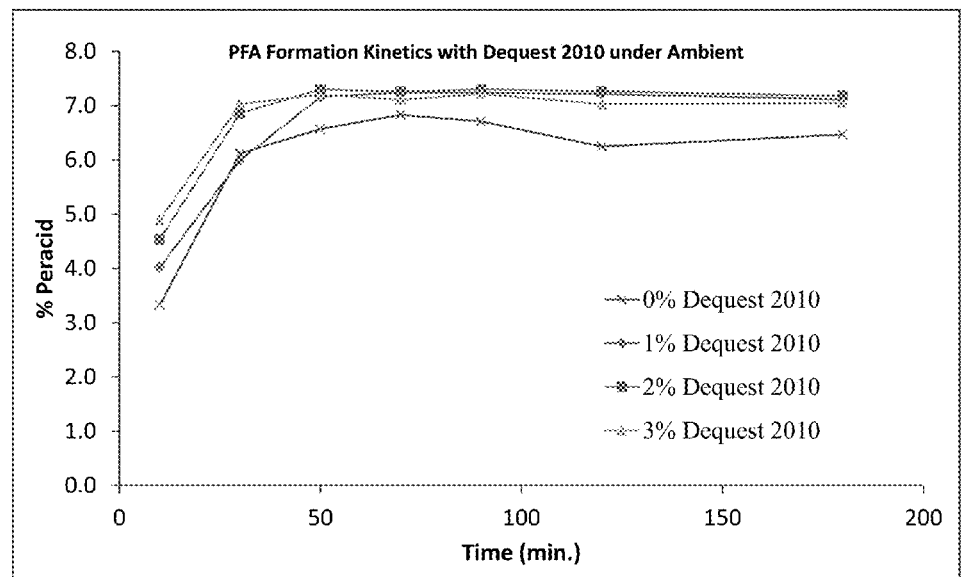
FIGS. 17-18 illustrate peroxyformic acid generation using a catalyst at different concentrations according to embodiments of the invention.

Peroxyformic acid generation under ambient temperature was evaluated using a catalyst (Dequest 2010) at different concentrations as shown in FIG. 17. As shown an increase in peroxyformic generation is observed at increasing concentrations of the Dequest 2010 catalyst.

Figure 18:
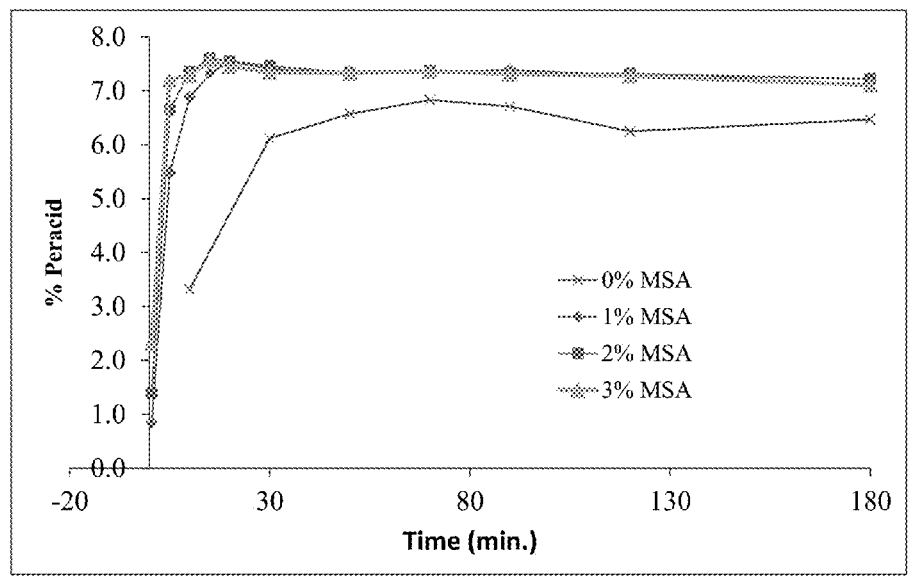

Peroxyformic acid generation under ambient temperature was evaluated using a catalyst (MSA (methyl sulfonic acid)) at different concentrations as shown in FIG. 18. As shown an increase in peroxyformic generation is observed employing the catalyst with slight difference in peroxyformic generation at increasing concentrations of the MSA catalyst.

Figure 19:
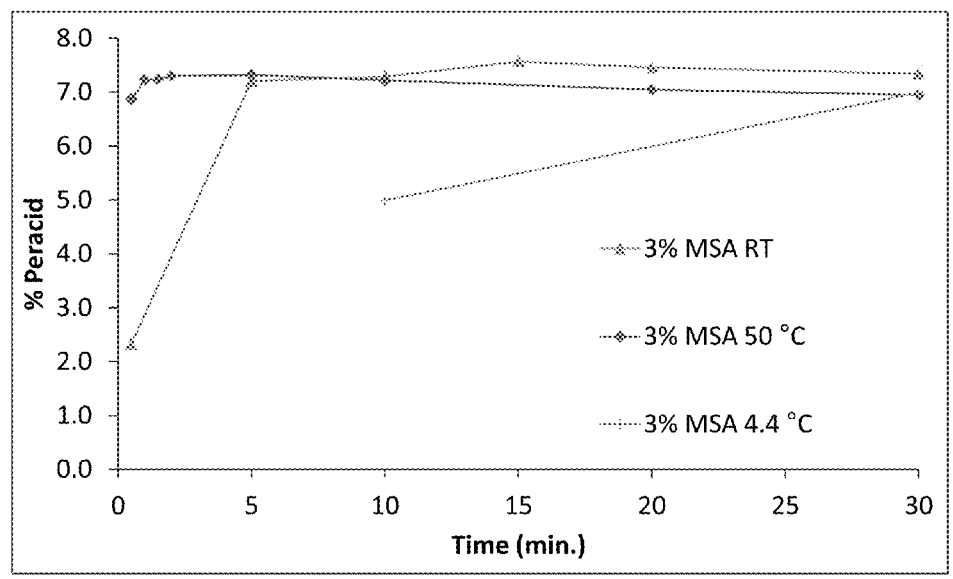
FIG. 19 illustrates peroxyformic acid generation using a catalyst at varying temperatures according to embodiments of the invention.

The effect of temperature on the formation of performic acid in the presence of the MSA catalyst was evaluated as shown in FIG. 19. A 3% concentration of MSA was evaluated at ambient/room temperature, 50° C. and 4.4° C.

Figure 20:
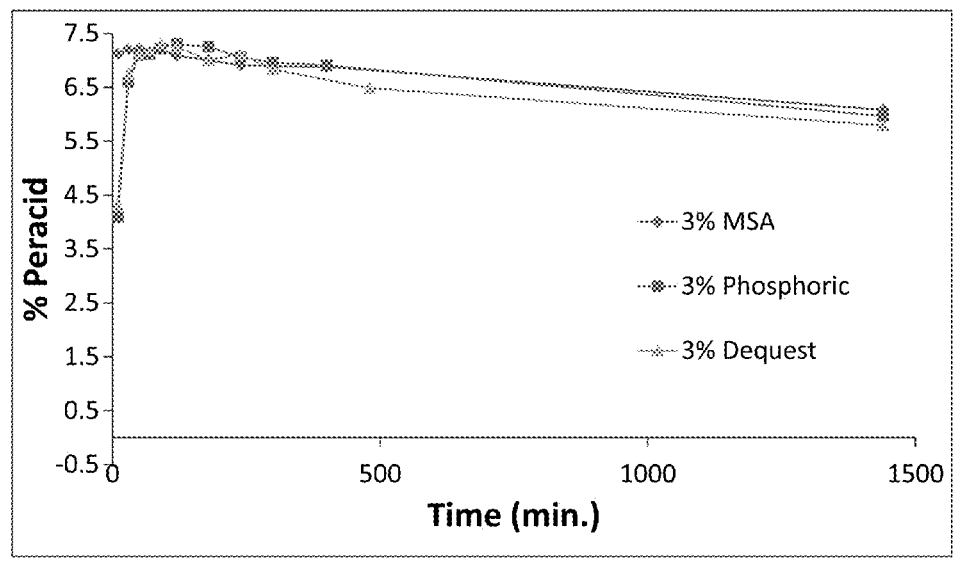
FIG. 20 illustrates the impact of performic acid stability in the presence of catalysts according to embodiments of the invention.

The stability of performic acid in the presence of different catalysts at room temperature was further evaluated as shown in FIG. 20.

Example 19. Use of Catalysts and Corrosion Inhibitor(s) in Generating Peroxyformic Acid Peroxyformic acid was generated in the presence of catalysts and various corrosion inhibitors as set forth in Table 19. A premix of formic acid, catalyst and corrosion inhibitor was formed and a second compound of only hydrogen peroxide were combined to in the amounts shown in Table 24.

TABLE 24

Generation of PFA in the presence of various corrosion inhibitors.

| Composition | 1 | 2 | 3 | 4 |
|---|---|---|---|---|
| CI 2 | 0.0 | 1.5 | 0.0 | 0.0 |
| CI 4 | 1.5 | 0.0 | 0.0 | 0.0 |
| CI 1 | 0.0 | 0.0 | 1.5 | 0.0 |
| CI 11 | 0.0 | 0.0 | 0.0 | 3.0 |
| Formic acid (97%) | 82.57 | 82.57 | 82.57 | 81.07 |
| $H_2O_2$ (35%) | 12.83 | 12.83 | 12.83 | 12.83 |
| MSA (70%) | 3 | 3 | 3 | 3 |
| DPA | 0.1 | 0.1 | 0.1 | 0.1 |
| Total | 100 | 100 | 100 | 100 |

All three evaluated corrosion inhibitors generated performic acid without any negative interaction (Composition 4 is control without CI) as shown in Table 25. However, stability of the formulation was impacted on the type of corrosion inhibitor added to the formulation. CI 11 provided the best stability (commercially available ammonium carbonate/bicarbonate corrosion inhibitor).

TABLE 25

Performic acid generation using formulations of Table 24.

| Time (min.) | % Performic | | | |
|---|---|---|---|---|
| | 1 | 2* | 3* | 4 |
| 5 | 6.69 | 6.67 | 6.71 | 6.28 |
| 10 | 6.72 | 6.59 | 6.62 | 6.62 |
| 20 | 6.67 | 6.07 | 6.20 | 6.73 |
| 30 | 6.67 | 5.62 | 5.56 | 6.70 |

*Hypochloride generated.

Example 20. Use of Premix Formulations for Formic Acid for Generating Performic Acid with Hydrogen Peroxide Formulations using 85% formic acid final formula and 32% peroxide in the formulation were evaluated using phosphoric acid, PEG or Glycerin as diluent and CI 11 as a corrosion inhibitor as shown in Table 26 and 27 (Combination of premixes with peroxide).

TABLE 26

| | Premix C (25-3) % | Premix D (25-4) % | Premix E (25-5) % | Premix F (25-6) % | Premix 25-7 % | Premix 25-8 % |
|---|---|---|---|---|---|---|
| Formic acid (97%) | 89.66 | 89.66 | 87.37 | 87.37 | 87.37 | 87.37 |
| Glycerin (99.5%) | 0.00 | 3.45 | 5.74 | 0 | 0.00 | 0.00 |
| MSA (70%) | 6.89 | 3.45 | 3.45 | 6.89 | 3.45 | 3.45 |
| CI 11 | 3.45 | 3.45 | 3.45 | 3.45 | 3.45 | 3.45 |
| Phosphoric acid (75%) | 0 | 0 | 0 | 2.29 | 5.73 | 0 |
| PEG | 0 | 0 | 0 | 0.00 | 0.00 | 5.74 |
| Total | 100.00 | 100.00 | 100.00 | 100.00 | 100.00 | 100.00 |

TABLE 27

A

| Material | 26-1 | 26-2 | 26-3 | 26-4 | 26-5 | 27-1 | 27-2 | 27-3 | 28-1 | 28-2 | 28-3 | 28-4 | 28-5 |
|---|---|---|---|---|---|---|---|---|---|---|---|---|---|
| Premix C (25-3) | 87.17 | 89.17 | 91.17 | 92.17 | 93.17 | 0 | 0 | 0 | 0 | 0 | 0 | 0 | 0 |
| Premix D (25-4) | 0 | 0 | 0 | 0 | 0 | 87.17 | 89.17 | 91.17 | 0 | 0 | 0 | 0 | 0 |
| Premix E (25-5) | 0 | 0 | 0 | 0 | 0 | 0 | 0 | 0 | 87.17 | 89.17 | 91.17 | 92.17 | 93.17 |
| Premix F (25-6) | 0 | 0 | 0 | 0 | 0 | 0 | 0 | 0 | 0 | 0 | 0 | 0 | 0 |
| Premix 25-7 | 0 | 0 | 0 | 0 | 0 | 0 | 0 | 0 | 0 | 0 | 0 | 0 | 0 |
| Premix 25-8 | | | | | | | | | | | | | |
| H2O2 (32%) | 12.83 | 10.83 | 8.83 | 7.83 | 6.83 | 12.83 | 10.83 | 8.83 | 12.83 | 10.83 | 8.83 | 7.83 | 6.83 |
| Total | 100 | 100 | 100 | 100 | 100 | 100 | 100 | 100 | 100 | 100 | 100 | 100 | 100 |

B

| Material | 29-3 | 29-4 | 29-5 | 30-3 | 30-4 | 30-5 | 31-3 | 31-4 | 31-5 |
|---|---|---|---|---|---|---|---|---|---|
| Premix C (25-3) | 0 | 0 | 0 | 0 | 0 | 0 | 0 | 0 | 0 |
| Premix D (25-4) | 0 | 0 | 0 | 0 | 0 | 0 | 0 | 0 | 0 |
| Premix E (25-5) | 0 | 0 | 0 | 0 | 0 | 0 | 0 | 0 | 0 |
| Premix F (25-6) | 91.17 | 92.17 | 93.17 | 0 | 0 | 0 | 0 | 0 | 0 |
| Premix 25-7 | 0 | 0 | 0 | 91.17 | 92.17 | 93.17 | | | |
| Premix 25-8 | | | | | | | 91.17 | 92.17 | 93.17 |
| H2O2 (32%) | 8.83 | 7.83 | 6.83 | 8.83 | 7.83 | 6.83 | 8.83 | 7.83 | 6.83 |
| Total | 100 | 100 | 100 | 100 | 100 | 100 | 100 | 100 | 100 |

Example 21. Oxygen Release

One of the advantages of performic acid is the release of zero oxygen in treatment systems. This is in sharp contrast to peracetic acid. Oxygen release was monitored by dissolved oxygen probes or an orbisphere (DO monitor).

Treatment in Produced Water

Figure 21:
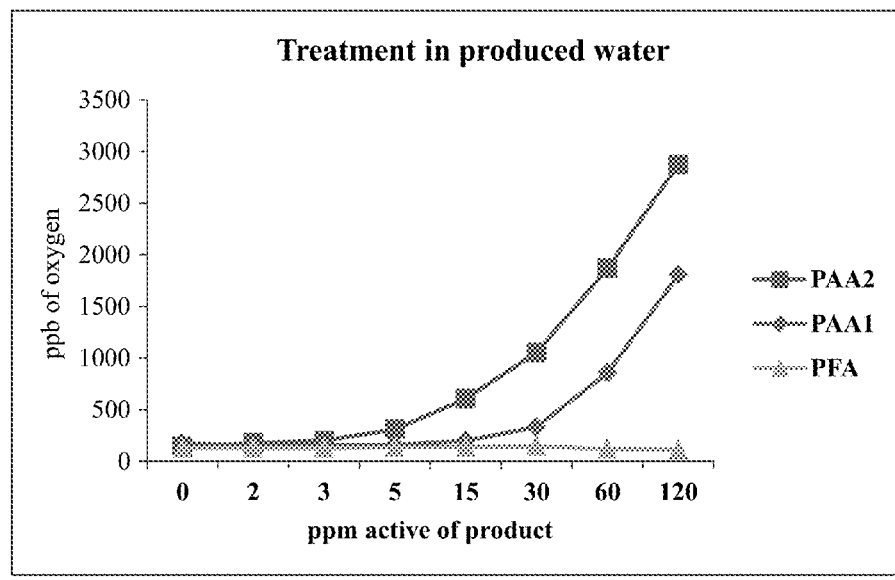
FIG. 21 shows according to embodiments of the invention that performic acid does not introduce oxygen into the treatment systems.

Formulation containing methyl sulfonic acid (no corrosion inhibitor) and treatment in produced water were evaluated in PAA 2 (15% Peracetic acid/10% peroxide), PAA 1 (21% peracetic acid, 3.65% peroxide) and PFA (7.5% peracetic acid, 0.2% peroxide). Oxygen release in formulations using 95-98% formic acid and 35% peroxide were evaluated as shown in FIG. 21 showing that performic acid does not introduce oxygen into the treatment system in contrast with peracetic acid formulations.

Treatment in Sea Water

Figure 22:
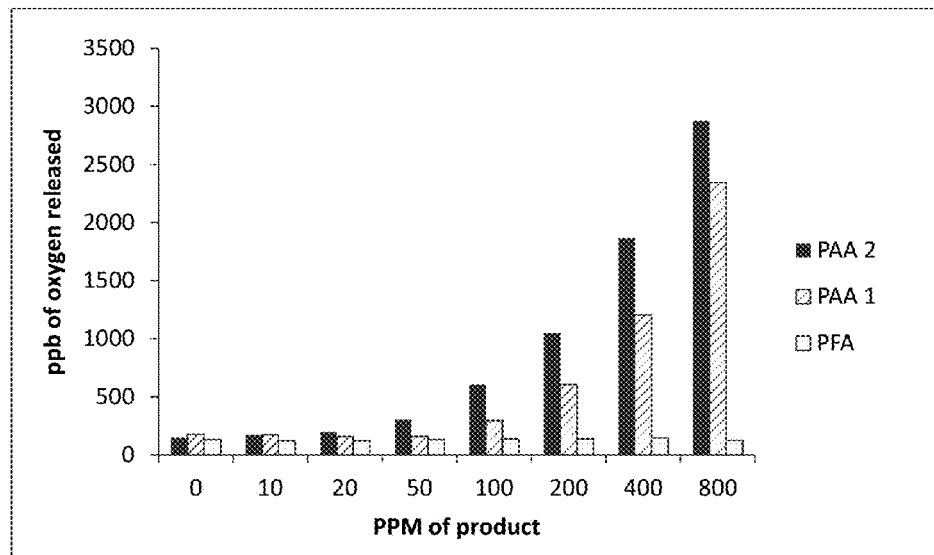
FIG. 22 illustrates evaluation of oxygen release in evaluated sea waters according to embodiments of the invention.

The formulations were evaluated for oxygen release in sea water with 500 ppm of iron at 22° C. The results are shown in FIG. 22.

For measuring oxygen, water was purged with carbon dioxide to displace all oxygen. Previously determined dosage of the product was added to the test condition under constant stirring. Oxygen reading was recorded 20 sec to 5 min after each addition to allow for equilibrium.

Ratios of PFA to Peroxide Providing No Oxygen Release

Figure 23:
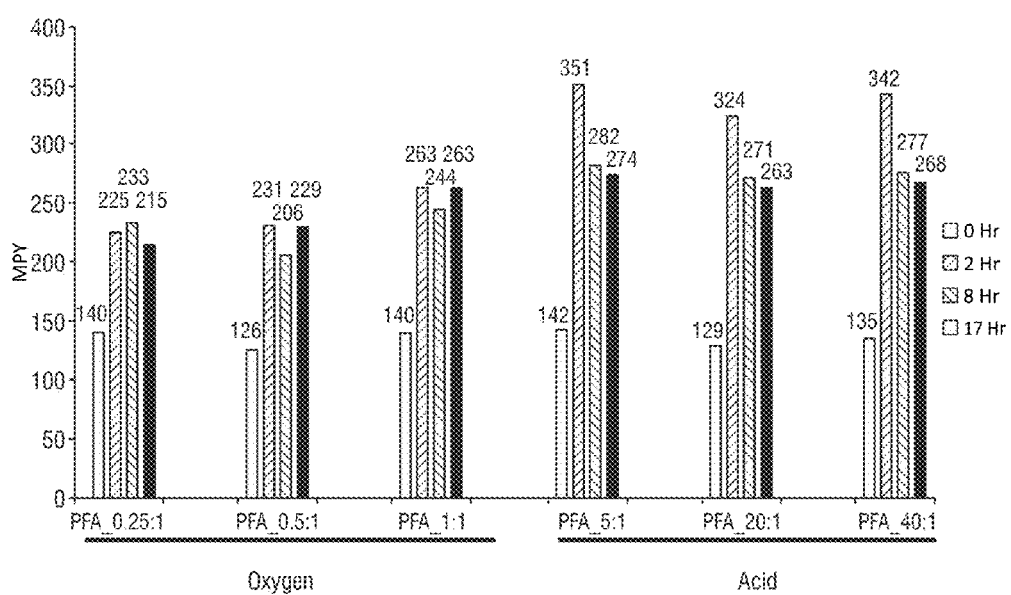
FIG. 23 illustrates corrosion profiles at different ratios of performic acid to peroxide according to embodiments of the invention.

From experiments performed in static bubble cells using synthetic sea water the optimal ratio of performic acid to peroxide was determined to be 5:1 or greater of performic acid: peroxide. At concentrations lower than 5:1 ratio the formulations release oxygen. FIG. 23 provides corrosion profiles at different ratios of performic acid to peroxide. It is observed that ratios of 40:1, 20:1 and 5:1 produce very similar corrosion profile whereas ratios lower than that oxidize the carbon steel. Primary corrosion from formulations containing PFA: peroxide of 5:1 and higher is from the acid component in the formulation. Formulations with PFA: peroxide lower than 5:1 is primarily due to oxygen.

Figure 24:
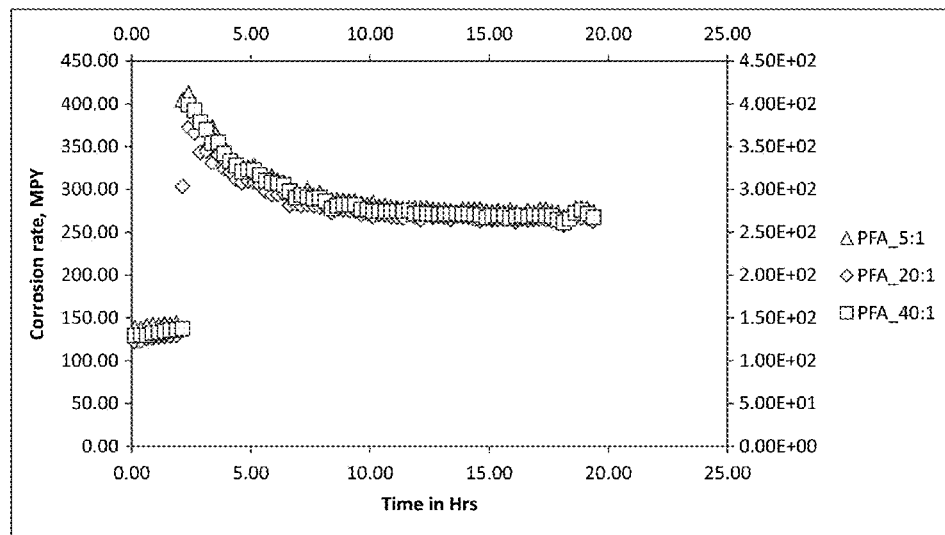
FIG. 24 illustrates corrosion profiles at ratios of performic acid to peroxide of 40:1, 20:1 and 5:1 according to embodiments of the invention.

Corrosion profiles of PFA to peroxide ratios at 40:1, 20:1 and 5:1 are further depicted in FIG. 24. The corrosion profiled show that ratios of 40:1, 20:1 and 5:1 provide similar corrosion trends to each other. All these formulations do not generate any oxygen.

Corrosion Control of the Acid Component of Performic Acid.

Corrosion inhibitors can be added to treatment systems either prior to treatment with performic acid, with the treatment or after treatment with performic acid. If a separate corrosion treatment is necessary the following experiments show that pre-treatment is the best option. The experiments were performed by immersing a carbon steel corrosion coupon in water treated with 200 ppm of active PFA. 50 ppm of corrosion inhibitors was either treated prior to, during the same time or after performic acid treatment. Coupons were weighed after 2 weeks in treatment waters at 50 C. Weight loss indicates corrosion and is marked with an "X" in Table 28. No weight loss indicates complete corrosion protection and is indicated by an absence of an "X". Control is untreated produced water.

TABLE 28

| corrosion summary | pre | with | post |
|---|---|---|---|
| CI A | | X | X |
| CI B | | X | X |
| CI C | | X | |
| CI D | | X | X |
| CI 1 | | X | X |
| CI 2 | | X | X |
| CI 3 | | X | X |
| CI 4 | X | | X |
| CI 5 | X | X | X |
| CI 7 | X | | X |
| CI 8 | | X | X |
| CI 9 | | X | X |
| CI 10-350 | | X | X |
| CI 10-303 | | X | X |
| Control | X | X | X |
| control 2-PW | X | X | X |

Based on the initial experiment it was determined that a corrosion inhibitor is best added prior to addition of performic acid to sea water. The Table 29 shows performance of different types of corrosion inhibitor molecules in protecting carbon steel against performic acid corrosion (PFA: Peroxide of 38:1). MPY indicates corrosion rate.

TABLE 29

| | Chemical | Dosage (ppm) | Baseline (mpy) | 2 hrs after dosing | | 8 hrs after dosing | | Last hour of testing | |
|---|---|---|---|---|---|---|---|---|---|
| | | | | mpy | % Protection | mpy | % Protection | mpy | % Protection |
| Cell 12 | CI 2 | | 114.0 | 86.7 | 23.9 | 33.5 | 70.6 | 21.9 | 80.8 |
| Cell 11 | CI 1 | | 44.6 | 18.1 | 59.5 | 11.1 | 75.1 | 10.3 | 76.9 |
| Cell 10 | CI 4 | | 31.7 | 17.8 | 43.8 | 19.5 | 38.5 | 4.8 | 84.8 |
| Cell 9 | CI 3 | | 27.3 | 48.0 | −75.6 | 82.3 | −201.2 | 84.8 | −210.4 |
| Cell 8 | CI 5 | | 61.7 | 77.3 | −25.3 | 151.0 | −144.9 | 147.2 | −138.7 |
| Cell 7 | CI 7 | | 19.5 | 249.6 | −1180.9 | 381.2 | −1856.4 | 553.6 | −2741.3 |
| Cell 6 | CI 8 | | 90.2 | 29.5 | 67.2 | 51.3 | 43.1 | 89.8 | 0.4 |
| Cell 5 | CI 9 | | 58.4 | 5.6 | 90.4 | 4.8 | 91.8 | 3.7 | 93.6 |
| Cell 4 | CI 10 | | 41.9 | 19.8 | 52.7 | 14.0 | 66.5 | 14.4 | 65.7 |
| Cell 3 | CI B | | 16.8 | 25.7 | −52.6 | 32.0 | −90.1 | 31.5 | −87.5 |
| Cell 2 | PFA | | 32.3 | 236.2 | −631.1 | 243.1 | −652.3 | 419.4 | −1197.9 |
| Cell 1 | Ester | | 140.5 | 274.7 | −95.5 | 281.9 | −100.6 | 254.1 | −80.8 |

Performance of corrosion inhibitor in sea water and produced water systems. 200 ppm active of performic acid was added. 50 ppm of corrosion inhibitor was added for corrosion protection. % protection was plotted by comparison of the corrosion rate in the presence of corrosion inhibitor to the corrosion rate with no corrosion inhibitor addition (PFA or PFA-PW) as shown in Table 30.

TABLE 30

| Chemical | Dosage (ppm) | Baseline (mpy) | 3 hrs after dosing | | 8 hrs after dosing | | Last hour of testing | |
|---|---|---|---|---|---|---|---|---|
| | | | mpy | % Protection | mpy | % Protection | mpy | % Protection |
| CI 10-PW | | 5.1 | 12.2 | −139.9 | 2.2 | 56.1 | 1.2 | 76.0 |
| CI 10 | | 34.7 | 25.2 | 27.6 | 19.4 | 44.2 | 17.7 | 49.0 |
| CI 9-PW | | 4.7 | 2.5 | 47.1 | 2.0 | 58.6 | 1.6 | 65.2 |
| CI 9 | | 98.0 | 4.3 | 95.6 | 3.1 | 96.8 | 2.7 | 97.3 |
| CI 4-PW | | 3.8 | 4.4 | −17.4 | 3.2 | 16.4 | 2.9 | 24.5 |
| CI 4 | | 54.0 | 37.6 | 30.4 | 19.1 | 64.7 | 20.1 | 62.9 |
| CI 1-PW | | 5.7 | 3.9 | 32.2 | 2.4 | 58.6 | 2.1 | 62.8 |
| CI 1 | | 101.7 | 60.7 | 40.2 | 36.3 | 64.3 | 28.4 | 72.0 |
| CI 2-PW | | 4.9 | 2.5 | 48.1 | 1.4 | 70.3 | 1.3 | 73.5 |
| CI 2 | | 87.3 | 35.7 | 59.1 | 15.4 | 82.4 | 8.7 | 90.0 |
| PFA-PW | | 5.1 | 17.2 | −237.2 | 16.7 | −228.1 | 18.4 | −261.2 |
| PFA | | 5.1 | 545.9 | −10666.2 | 686.9 | −13447.5 | 739.4 | −14481.9 |

Corrosion Control

Figure 25:
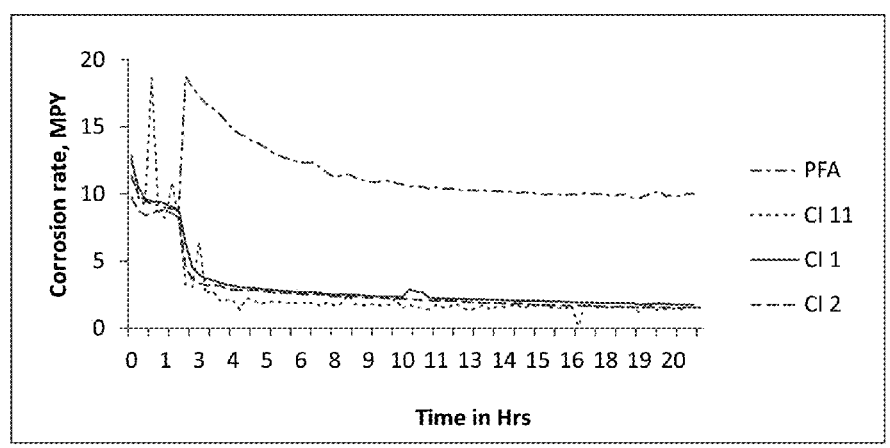
FIG. 25 illustrates bubble cell profiles of corrosion inhibition included in formic acid co-formulations according to embodiments of the invention.

As shown in Example 19, corrosion inhibitors can be included in the formulation. Since performic acid equilibrium between formic acid premix and peroxide is fast inline formation of corrosion inhibitor included performic acid can afford the corrosion protection without the addition of an external corrosion inhibitor. FIG. 25 shows bubble cell profiles of corrosion inhibition provided by corrosion inhibitor included in the co-formulation as described in Example 19.

Figure 26:
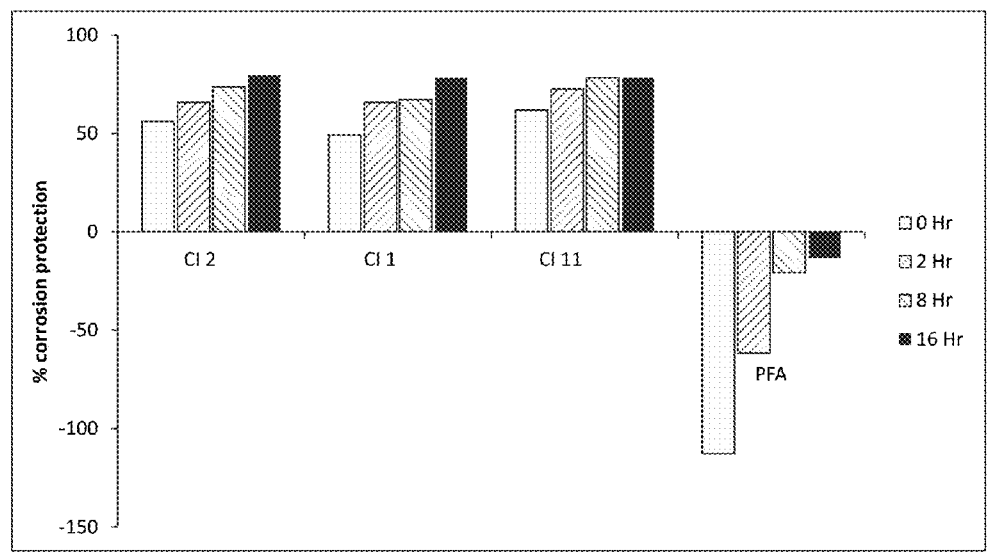
FIG. 26 illustrates corrosion inhibition in PFA treated systems according to embodiments of the invention.

As compared to PFA alone all corrosion inhibitors formulated provide significant corrosion protection compared to the background corrosion rate. The corrosion protection at 2, 8 and 16 hrs is shown in FIG. 26.

Example 22. Biocidal Performance of Performic Acid

The following test system shown in Table 31 was evaluated for log reduction of *Pseudomonas aeruginosa*.

TABLE 31

| Test Systems: | *Pseudomonas aeruginosa* ATCC 15442 |
|---|---|
| Test Substance Diluents: | 500 ppm synthetic hard water, pH 7.74 |
| Test Substances: | A. 0.5 ppm PFA: 47 µL PFA Concentrate (0.107% PFA)/99 mL diluent pH 6.71 |
| | B. 1.0 ppm PFA: 93 µL PFA Concentrate (0.107% PFA)/99 mL diluent pH 6.31 |
| | C. 2.0 ppm PFA: 185 µL PFA Concentrate (0.107% PFA)/99 mL diluent pH 5.34 |
| Exposure Time(s): | 10 minutes and 4 hours |
| Neutralizer: | 9 mL DE Broth |
| Test Temperature | 25° C. |
| Plating Medium: | TGE |
| Incubation: | 35° C. for 48 hours |

Figure 27:
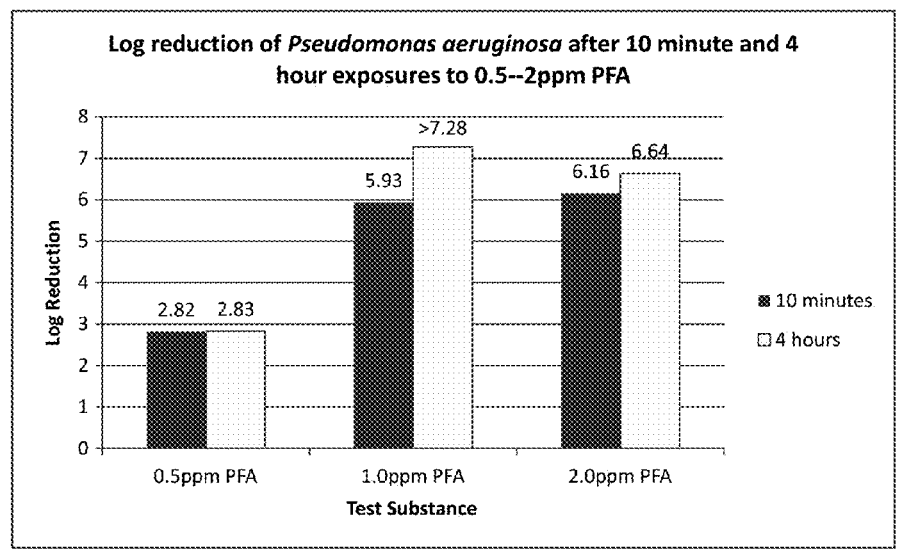
FIG. 27 illustrates the biocidal efficacy of performic acid generated according to embodiments of the invention.

FIG. 27 shows the results of biocidal efficacy after 10 minutes contact and 4 hours contact showing the beneficially efficacy of performic acid generated according to the invention.

Example 23. Biocidal Performance of Performic Acid on Treated Produced Water

Figure 28:
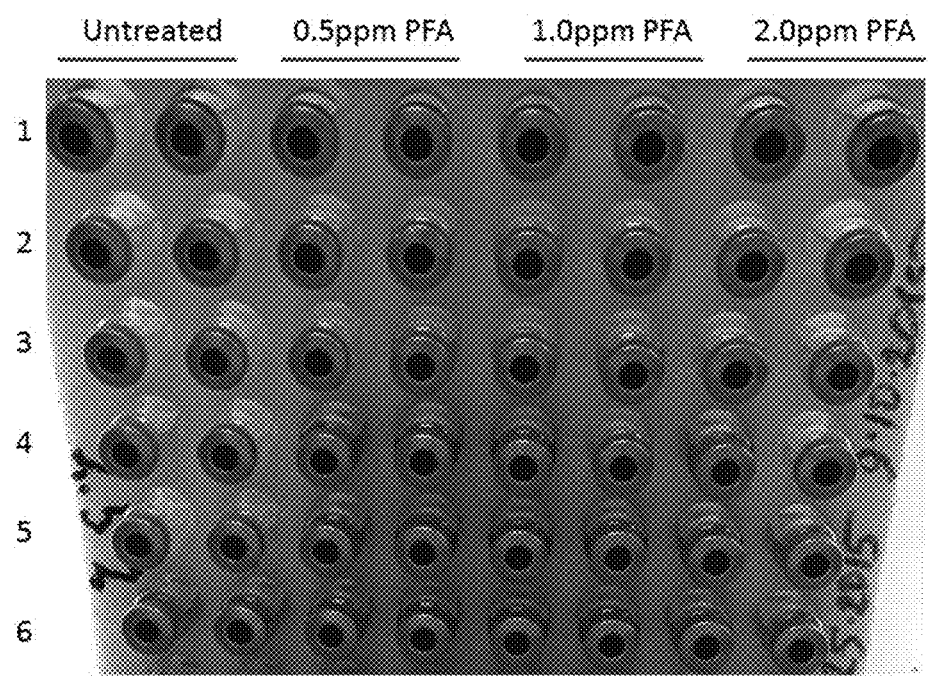
FIG. 28 illustrates the biocidal efficacy of performic acid generated according to embodiments of the invention in produced waters.

Treatment of produced water with performic acid was evaluated using performic acid compositions containing a corrosion inhibitor. As shown in FIG. 28 (grey scale) the lighter color indicates no growth in the water, whereas the darker shading indicates no growth. Untreated has E5 bacteria/mL; 0.5 ppm PFA treated has E3 bacteria/mL. The bacterial bug bottles are specific in supporting growth of acid producing bacteria (APBs). Growth of APB is indicated by a color change from dark to light color (pink to yellow). 1 mL of initial inoculum was diluted 10 times in subsequent bottles. Therefore each bottle indicates a E1 bacteria/mL. Based on the results observed by growth/no growth of bacteria it can be concluded that PFA treatment results in at least a reduction of 2 log (equivalent of E2 bacteria/mL) bacteria.

Example 24. Biofilm Biocidal Performance

Figure 29:
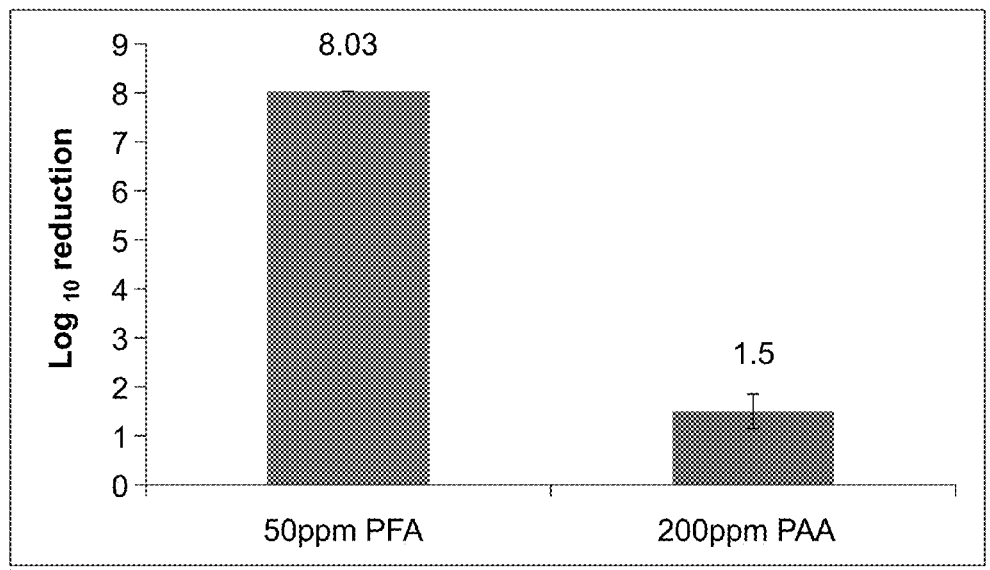
FIG. 29 illustrates the biocidal efficacy of performic acid generated according to embodiments of the invention against biofilms.

A *Pseudomonas* biofilm was treated with 50 ppm active of PFA and compared to efficacy treated with 200 ppm PAA. *Pseudomonas* biofilms were grown in a CDC biofilm reactor on a poly carbonate coupons. Appropriate concentration of the treatment substance were diluted in hardwater at pH 7.71 diluent. Test chemicals were exposed for 3 hrs after which they were treated with 16 mLs of thiosulfate to neutralize any oxidants. The untreated control and treated *Pseudomonas* were plated on a TGE media and incubated at 35° C. for 48 hrs. A 4 hr reduction was monitored by colony counting of *Pseudomonas* on plates. Results are shown in FIG. 29 demonstrating the beneficially efficacy of PFA generated according to the invention.

Example 25. Iron Sulfide Oxidation

Figure 30:
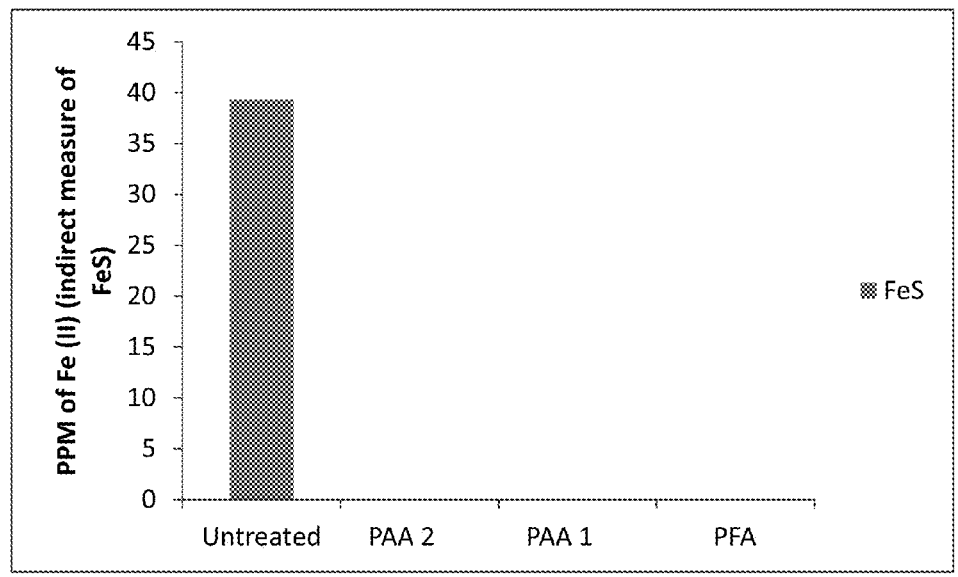
FIG. 30 illustrates the oxidization of iron sulfide in produced water treated with performic acid generated according to embodiments of the invention.

The extent of oxidation of iron sulfide in water source (produced water) was evaluated using performic acid compared to peracetic acid. As shown in FIG. 30 complete oxidation of iron sulfide in produced water is achieved with performic acid (PFA). This property is similar to that observed for peracetic acid also. Iron (II) was measured 30 minutes after the addition of the oxidant into treated waters.

Example 25. Hydrogen Sulfide Oxidation

Figure 31:
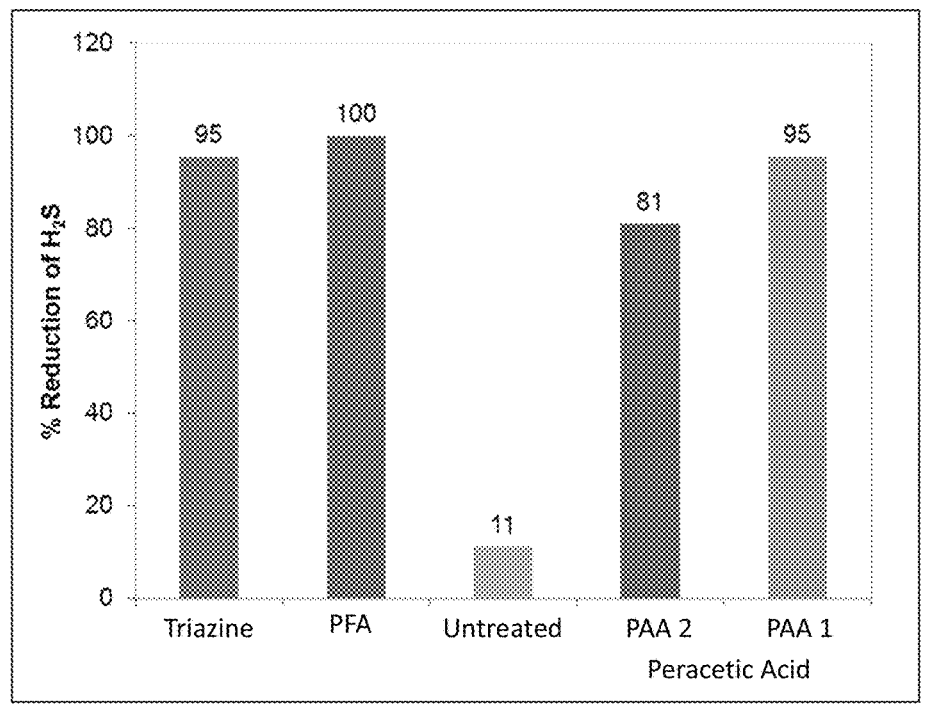
FIG. 31 illustrates the reduction of $H_2S$ in produced water treated with performic acid generated according to embodiments of the invention.

Hydrogen sulfide reduction was measured in produced water treated with performic acid (10 ppm active added to produced water containing 2000 ppm of $H_2S$). 30 ppm active of PAA 2 and PAA 1 were added. 30 ppm active of Triazine was added as comparison. Triazine chelates $H_2S$ however peracid oxidizes $H_2S$. Concentration of $H_2S$ was measured using a Dragger tube by sampling the head space. $H_2S$ containing sample was constantly stirred. Total $H_2S$ indicated below was measured 1 hr. after treatment. The results are shown in FIG. 31.

Example 26. Reduction of *E. coli* Using Performic Acid Compositions

Nalidixic acid resistant *E. coli* O157:H7 was used to evaluate the efficacy in treatment with performic acid composition on raw beef brisket according to the conditions shown in Table 32.

TABLE 32

| | |
|---|---|
| Test System: | Nalidixic acid resistant *E. coli* O157:H7 |
| Test Substance Diluent: | Sterile DI Water buffered to pH 9.5 with sodium bicarbonate and carbonate |
| Red Meat: | Beef flank steak/brisket, cut into 5 cm square pieces |
| Inoculation: | 100 µl, spot inoculated and then spread with a sterile hockey stick |
| Attachment Time: | 1 hour at 4° C. |
| Treatment: | Dip for 10 minutes, allowing chemistry to drain off of meat for 15 seconds before neutralizing (3 samples a time) |
| Neutralizer: | 50 mL DE Broth |
| Recovery: | Stomached meat in neutralizer for 30 seconds at 230 rpm |
| Test Temperature | Ambient |
| Plating Medium: | TSA with nalidixic acid (1 ml/L media) |
| Incubation: | 35° C. for 48 hours |
| Notes: | Ester PFA turned meat white/gray during treatment |

The micro results are shown in Tables 33-34. demonstrating improved micro efficacy (log reduction) achieved from PFA compositions in comparison to POAA.

TABLE 33

| Test Substance | Exposure Time | Plate Count | Plate Dilution | CFU/ml | CFU/cm2 | Log CFU/cm2 | Standard Deviation | Average Log CFU/cm2 | Log Reduction |
|---|---|---|---|---|---|---|---|---|---|
| 220 ppm POAA, pH 8.86 | 10 minutes | 60 | 10 | 6.00E+02 | 1.20E+03 | 3.08 | 0.09 | 2.98 | 1.6 |
| | | 45 | 10 | 4.50E+02 | 9.00E+02 | 2.95 | | | |
| | | 40 | 10 | 4.00E+02 | 8.00E+02 | 2.90 | | | |
| 220 ppm POAA + 50 ppm LAS pH 8.88 | | 41 | 10 | 4.10E+02 | 8.20E+02 | 2.91 | 0.10 | 2.99 | 1.05 |
| | | 63 | 10 | 6.30E+02 | 1.26E+03 | 3.10 | | | |
| | | 45 | 10 | 4.50E+02 | 9.00E+02 | 2.95 | | | |
| 180 ppm PFA, pH 8.76 | | 92 | 10 | 9.20E+02 | 1.84E+03 | 3.26 | 0.06 | 3.22 | 0.83 |
| | | 71 | 10 | 7.10E+02 | 1.42E+03 | 3.15 | | | |
| | | 86 | 10 | 8.60E+02 | 1.72E+03 | 3.24 | | | |
| 180 ppm PFA + 50 ppm LAS pH 8.79 | | 103 | 10 | 1.03E+03 | 2.06E+03 | 3.31 | 0.04 | 3.29 | 0.76 |
| | | 87 | 10 | 8.70E+02 | 1.74E+03 | 3.24 | | | |
| | | 100 | 10 | 1.00E+03 | 2.00E+03 | 3.30 | | | |
| (2 part PFA-forming) 180 ppm PFA, pH 6.61 | | 16 | 10 | 1.60E+02 | 3.20E+02 | 2.51 | 0.22 | 2.74 | 1.30 |
| | | 31 | 10 | 3.10E+02 | 6.20E+02 | 2.79 | | | |
| | | 43 | 10 | 4.30E+02 | 8.60E+02 | 2.93 | | | |
| (2 part PFA-forming) + LAS 180 ppm PFA + 50 ppm LAS pH 6.66 | | 26 | 10 | 2.60E+02 | 5.20E+02 | 2.72 | 0.26 | 2.71 | 1.33 |
| | | 47 | 10 | 4.70E+02 | 9.40E+02 | 2.97 | | | |
| | | 14 | 10 | 1.40E+02 | 2.80E+02 | 2.45 | | | |
| LAS 50 ppm LAS pH 9.47 | | 41 | 100 | 4.10E+03 | 8.20E+03 | 3.91 | 0.15 | 3.78 | 0.27 |
| | | 31 | 100 | 3.10E+03 | 6.20E+03 | 3.79 | | | |
| | | 21 | 100 | 2.10E+03 | 4.20E+03 | 3.62 | | | |
| Water Control DI $H_2O$ Buffered to pH 9.5 | | 27 | 100 | 2.70E+03 | 5.40E+03 | 3.73 | 0.06 | 3.80 | |
| | | 33 | 100 | 3.30E+03 | 6.60E+03 | 3.82 | | | |
| | | 35 | 100 | 3.50E+03 | 7.00E+03 | 3.85 | | | |
| Non-treated Controls | | 61 | 100 | 6.10E+03 | 1.22E+04 | 4.09 | 0.06 | 4.04 | |
| | | 59 | 100 | 5.90E+03 | 1.18E+04 | 4.07 | | | |
| | | 47 | 100 | 4.70E+03 | 9.40E+03 | 3.97 | | | |
| Inoculum Numbers | | 42 | 100000 | 4.20E+06 | | | | | |
| | | 54 | 100000 | 5.40E+06 | | | | | |
| Background Numbers | | 25 | 10 | 2.50E+02 | | | | | |
| | | 46 | 10 | 4.60E+02 | | | | | |

TABLE 34

Micro Efficacy Results Summarized

| Test Substance | Log Reduction |
|---|---|
| 220 ppm POAA, pH 8.86 | 1.06 |
| 220 ppm POAA + 50 ppm LAS pH 8.88 | 1.05 |
| (2 part PFA-forming) 180 ppm PFA, pH 6.61 | 1.30 |
| (2 part PFA-forming) + LAS 180 ppm PFA + 50 ppm LAS pH 6.66 | 1.33 |

Example 27. Bactericidal Activity of PFA Versus POAA

*Staphylococcus*, *Enterococcus* and *Pseudomonas* pathogens were used to evaluate the micro efficacy of PFA in comparison to POAA. The test methods are shown in Table 35 and the results are shown in Tables 36-39.

TABLE 35

Test Parameters

| | |
|---|---|
| Test Systems: | *Staphylococcus aureus* ATCC 6538 (0.217 A @ 620 nm) *Enterococcus hirae* ATCC 10541 (0.184 A @ 620 nm) *Pseudomonas aeruginosa* ATCC 15442 (0.191 A @ 620 nm) |
| Test Substances: | PFA (9.86% PFA) POAA (14.95% POAA) |

TABLE 35-continued

Test Parameters

| | |
|---|---|
| Test Substance Diluent: | EN Synthetic Hard Water, pH 7.04 |
| Test Substance Dilutions: | 20 ppm PFA × 1.25  pH 6.61 |
| | 30 ppm PFA × 1.25  pH 6.74 |
| | 50 ppm PFA × 1.25  pH 6.60 |
| | 25 ppm POAA (molar equivalent to 20 ppm PFA) × 1.25 pH 6.73 |
| | 38 ppm POAA (molar equivalent to 30 ppm PFA) × 1.25 pH 6.74 |
| | 62 ppm POAA (molar equivalent to 50 ppm PFA) × 1.25 pH 6.98 |
| Interferring Substance: | Dirty Conditions Bovine Albumin Solution (3 g/L) + sheep erythrocytes |
| Exposure Time(s): | 5 minutes |
| Neutralizer: | 8 mL DE Broth + 1 mL sterile water |
| Test Temperature: | 20° C. |
| Plating Medium: | Oxoid TSA |
| Incubation: | 35° C. for 48 hours |

TABLE 36

Results

| Test Substance | Exposure Time | Organic Soil | Average CFU/mL | $Log_{10}$ Growth | $Log_{10}$ Reduction |
|---|---|---|---|---|---|
| 20 ppm PFA × 1.25 pH 6.61 | 5 minutes | Dirty Conditions (High concentration Bovine Albumin Solution + sheep erythrocytes) | <140 | <2.15 | >5.15 |
| 30 ppm PFA × 1.25 pH 6.74 | | | <140 | <2.15 | >5.15 |
| 50 ppm PFA × 1.25 pH 6.60 | | | <140 | <2.15 | >5.15 |
| 24.8 ppm POAA × 1.25 pH 6.73 | | | 1.77E+05 | 5.25 | 2.05 |
| 37.6 ppm POAA × 1.25 pH 6.90 | | | <140 | <2.15 | >5.15 |
| 62.4 ppm POAA × 1.25 pH 6.98 | | | <140 | <2.15 | >5.15 |
| Test Mixture Inoculum Numbers ($N_o$) | | | 1.97E+07 | 7.30 | |
| *S. aureus* ATCC 6538 | | | 1.97E+08 | | |
| Test Suspension Numbers (N) | | | | | |
| Validation Test Suspension Numbers ($N_v$) | | | 5.70E+02 | | |
| Control Mixture Inoculum Numbers ($N_{vo}$) | | | 5.70E+01 | | |
| Control A | Dirty Conditions | | 5.60E+01 | | |
| Control B | | | 7.40E+01 | | |
| Control C-A | Dirty Conditions | | 5.90E+01 | | |
| Control C-B | | | 6.00E+01 | | |

TABLE 37

Results

| Test Substance | Exposure Time | Organic Soil | Average CFU/mL | $Log_{10}$ Growth | $Log_{10}$ Reduction |
|---|---|---|---|---|---|
| 20 ppm PFA × 1.25 pH 6.61 | 5 minutes | Dirty Conditions (High concentration Bovine Albumin Solution + sheep erythrocytes) | 6.30E+03 | 3.80 | 3.46 |
| 30 ppm PFA × 1.25 pH 6.74 | | | 2.15E+02 | 2.33 | 4.92 |
| 50 ppm PFA × 1.25 pH 6.60 | | | <140 | <2.15 | >5.10 |
| 24.8 ppm POAA × 1.25 pH 6.73 | | | >3.30E+05 | >5.52 | <1.74 |
| 37.6 ppm POAA × 1.25 pH 6.90 | | | 9.25E+03 | 3.97 | 3.29 |
| 62.4 ppm POAA × 1.25 pH 6.98 | | | <140 | <2.15 | >5.10 |
| Test Mixture Inoculum Numbers ($N_o$) | | | 1.80E+07 | 7.26 | |
| *E. hirae* ATCC 10541 | | | 1.80E+08 | | |
| Test Suspension Numbers | | | | | |
| Validation Test Suspension Numbers ($N_v$) | | | 4.30E+02 | | |
| Control Mixture Inoculum Numbers ($N_{vo}$) | | | 4.30E+01 | | |
| Control A | Dirty Conditions | | 7.70E+01 | | |
| Control B | | | 6.60E+01 | | |
| Control C-A | Dirty Conditions | | 4.60E+01 | | |
| Control C-B | | | 5.30E+01 | | |

TABLE 38

Results

| Test Substance | Exposure Time | Organic Soil | Average CFU/mL | $Log_{10}$ Growth | $Log_{10}$ Reduction |
|---|---|---|---|---|---|
| 20 ppm PFA × 1.25 pH 6.61 | 5 minutes | Dirty Conditions (High concentration Bovine Albumin Solution + sheep erythrocytes) | <140 | <2.15 | >5.22 |
| 30 ppm PFA × 1.25 pH 6.74 | | | <140 | <2.15 | >5.22 |
| 50 ppm PFA × 1.25 pH 6.60 | | | <140 | <2.15 | >5.22 |
| 24.8 ppm POAA × 1.25 pH 6.73 | | | <140 | <2.15 | >5.22 |
| 37.6 ppm POAA × 1.25 pH 6.90 | | | <140 | <2.15 | >5.22 |
| 62.4 ppm POAA × 1.25 pH 6.98 | | | <140 | <2.15 | >5.22 |
| Test Mixture Inoculum Numbers ($N_o$) | | | 2.35E+07 | 7.37 | |
| *P. aeruginosa* ATCC 15442 | | | 2.35E+08 | | |
| Test Suspension Numbers | | | | | |
| Validation Test Suspension Numbers ($N_v$) | | | 5.05E+02 | | |
| Control Mixture Inoculum Numbers ($N_{vo}$) | | | 5.05E+01 | | |
| Control A | Dirty Conditions | | 8.40E+01 | | |
| Control B | | | 9.00E+01 | | |
| Control C-A | Dirty Conditions | | 5.50E+01 | | |
| Control C-B | | | 4.30E+01 | | |

TABLE 39

Passing Requirements & Results

| Passing Requirements per EN 1276: | *S. aureus* | *E. hirae* | *P. aeruginosa* |
|---|---|---|---|
| N is between $1.5 \times 10^8$ and $5.0 \times 10^8$ CFU/mL | N = 1.97 × $10^8$ | N = 1.80 × $10^8$ | N = 2.35 × $10^8$ |
| $N_{vo}$ is between 30 and 160 CFU/mL | $N_{vo}$ = 57 | $N_{vo}$ = 43 | $N_{vo}$ = 51 |

TABLE 39-continued

Passing Requirements & Results

| Passing Requirements per EN 1276: | S. aureus | E. hirae | P. aeruginosa |
|---|---|---|---|
| Controls A, B, C are equal to or greater than 0.5 × N$_{vo}$ | YES | YES | YES |
| A greater than 5 log$_{10}$ reduction (R) is achieved within the 5 minute contact time: | 20 ppm PFA – R = >5.15 | 20 ppm PFA – R = 3.46 | 20 ppm PFA – R = >5.22 |
| | 30 ppm PFA – R = >5.15 | 30 ppm PFA – R = 4.92 | 30 ppm PFA – R = >5.22 |
| | 50 ppm PFA – R = >5.15 | 50 ppm PFA – R = >5.10 | 50 ppm PFA – R = >5.22 |
| | 25 ppm POAA – R = 2.05 | 25 ppm POAA – R = <1.74 | 25 ppm POAA – R = >5.22 |
| | 38 ppm POAA – R = >5.15 | 38 ppm POAA – R = 3.29 | 38 ppm POAA – R = >5.22 |
| | 62 ppm POAA – R = >5.15 | 62 ppm POAA – R = >5.10 | 62 ppm POAA – R = >5.22 |

Example 28. Summary of Fungicidal and Sporicidal Activity of PFA

Various pathogens were used to evaluate the broad micro efficacy spectrum of PFA according to the present invention. The test method, substance and results are shown in Table 40.

TABLE 40

Micro Efficacy Test Parameters and Results

| Test Method | Test Substance | Test Organisms | Passing Requirement | Result |
|---|---|---|---|---|
| EN 13727 | 450 ppm PFA pH 6-7 | P. aeruginosa ATCC 15442 | 5 log reduction | PASS |
| | | Staph. Aureus ATCC 6538 | | PASS |
| | | Enterococcus hirae ATCC 10541 | | PASS |
| EN 13624 | | Canidia albicans ATCC 10231 | 4 log reduction | PASS |
| | | Aspergillus brasiliensis ATCC 1604 | | PASS |
| EN 13704 | | Bacillus subtilis ATCC 6633 | 3 log reduction | PASS |
| EN 14476 | | Poliovirus | 4 log reduction | PASS |

Example 29. Low Temperature, Low Oxygen Performance of PFA

Micro efficacy of PFA according to the present invention was evaluated under low temperature, low oxygen conditions employing the formulation of Table 41.

TABLE 41

| Composition | % |
|---|---|
| Formic acid | 80-90 |
| Hydrogen peroxide (35%) | 10-15 |
| Dequest 2010 (60%) | 0.1-5 |
| Total | 100 |
| PFA % | 7.5 |
| Hydrogen peroxide % | 0.2 |

Figure 32:
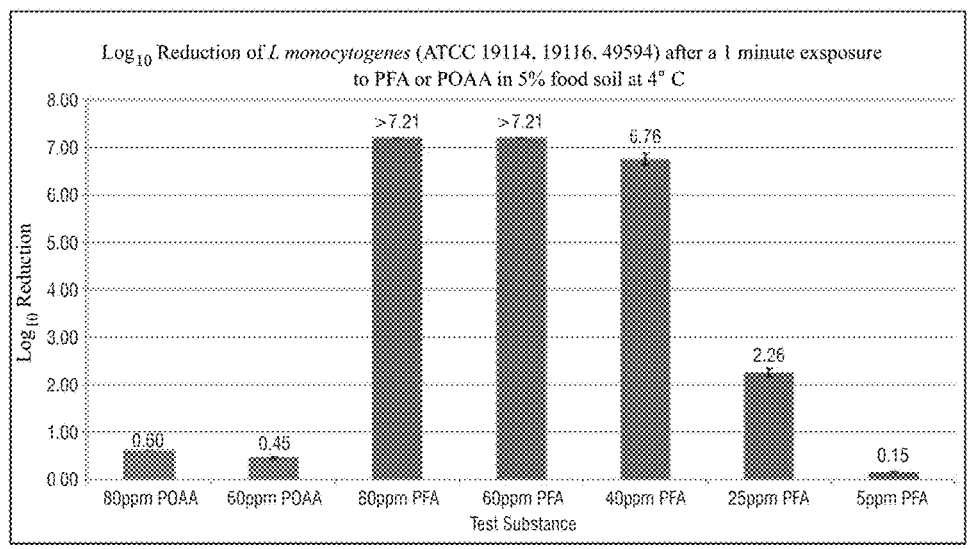
FIG. 32 illustrates the low temperature disinfectant efficacy of performic acid generated according to embodiments of the invention.

The log reduction of L. monocytogenes (ATCC 19114, 19116 and 4594) were evaluated at low temperature (4° C.) comparing peroxyacetic acid to the peroxyformic acid generated according to the formulation shown in Table 41. The results are shown in FIG. 32 comparing disinfectant efficacy after a 1 minute contact exposure to the disinfectants.

As shown, the disinfectant efficacy of the POAA significantly decreases at the lower temperature, such as used in brewery and other related applications. Beneficially, the disinfectant efficacy of the in situ generated peroxy formic acid does not decrease. As a result, the performic acid generated has a great fit for application in brewery plants. The exceptional antimicrobial efficacy of performic acid at low temperature meets the requirement of cold temperature environment of brewery operations, while common biocides including peroxycarboxylic acids such as peracetic acids will suffer the efficacy lose under low temperatures. In addition, formic acid that always coexists with performic acid is a very efficient acidulant, which will help prevent/dissolve beer stone, thus eliminate the additional acid wash. As a further benefit the performic acid composition has very high performic acid to $H_2O_2$ ratio, which practically eliminates the $O_2$ that could potentially introduced to the liquid being processed (i.e. beer) and interfere with the organoleptic effects and negative taste effects.

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which does not depart from the spirit or scope of the present inventive discovery. Such modifications are also intended to fall within the scope of the appended claims.

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

What is claimed is:

1. A method for forming peroxyformic acid comprising:
   contacting a formic acid source with a hydrogen peroxide source to form a resulting aqueous composition comprising a peracid that comprises peroxyformic acid, and from about 0.0001 wt-% to about 20 wt-% of a corrosion inhibitor;
   wherein the contacting is conducted in the presence of a mineral acid catalyst, and
   wherein before said contacting, the ratio between the concentration of said formic acid source (w/v) and the concentration of said hydrogen peroxide source (w/v) is at least about 4 or higher, and the ratio between the concentration of said peracid (w/w) and the concentration of hydrogen peroxide source (w/w) in said formed resulting aqueous composition reaches at least about 4 or higher within about 1 hour of said contacting.

2. The method of claim 1, wherein before the contacting, the formic acid source is provided in a composition that comprises formic acid or a substance that generates formic acid upon contact with an aqueous composition.

3. The method of claim 2, wherein before the contacting, the composition is an aqueous solution that comprises formic acid.

4. The method of claim 2, wherein the substance is a salt of formate or an ester of formate.

5. The method of claim 1, wherein before the contacting, the hydrogen peroxide source is provided in a composition that comprises hydrogen peroxide or a substance that generates hydrogen peroxide upon contact with an aqueous composition.

6. The method of claim 3, wherein before the contacting, the composition is an aqueous solution that comprises hydrogen peroxide.

7. The method of claim 5, wherein the substance comprises a precursor of hydrogen peroxide comprising sodium percarbonate, sodium perborate, urea hydrogen peroxide, PVP-hydrogen peroxide, or combinations thereof.

8. The method of claim 1, wherein the formic acid provided in a first aqueous composition is contacted with (a) the hydrogen peroxide provided in a second aqueous composition to form peroxyformic acid in the resulting aqueous composition, or (b) with a substance that generates hydrogen peroxide upon contact with an aqueous composition provided in a second solid composition to form peroxyformic acid in the resulting aqueous composition.

9. The method of claim 1, wherein the amount of corrosion inhibitor in the resulting aqueous composition is from about 0.0001 wt-% to about 10 wt-%.

10. The method of claim 9, wherein the corrosion inhibitor comprises a phosphate ester, a derivative of the phosphate ester, trimeric C19 unsaturated fatty acid, a quat amine, a derivative of the quat amine, an imidazoline, a derivative of the imidazoline, an alkyl pyridine, a derivative of the alkyl pyridine, a phosphonium salt or a derivative of the phosphonium salt.

11. The method of claim 1, wherein a formic acid source provided in a first solid composition is contacted with hydrogen peroxide provided in a second aqueous composition to form peroxyformic acid in the resulting aqueous composition.

12. The method of claim 1, wherein the formic acid source provided in a first solid composition and the hydrogen peroxide source provided in a second solid composition are contacted with a third aqueous composition to form peroxyformic acid in the resulting aqueous composition.

13. The method of claim 1, wherein the formic acid source and the hydrogen peroxide source are provided in a first solid composition, and the first solid composition is contacted with a second aqueous composition to form peroxyformic acid in the resulting aqueous composition.

14. The method of claim 1, wherein before the contacting, the ratio between the concentration of the formic acid source (w/v) and the concentration of the hydrogen peroxide source (w/v) is from about 100 to about 4, and wherein the ratio between the concentration of the peracid (w/w) and the concentration of hydrogen peroxide source (w/w) in the formed aqueous composition reaches from about 1500 to about 4 within about 1 hour of the contacting.

15. The method of claim 1, wherein the ratio between the concentration of the peracid (w/w) and the concentration of hydrogen peroxide (w/w) in the formed aqueous composition reaches from about 5 to about 40 within about 30 minutes of the contacting.

16. The method of claim 9, wherein the formed aqueous composition comprises about 5% (w/w) or less hydrogen peroxide.

17. The method of claim 3, wherein the formic acid and the hydrogen peroxide are contacted in the absence of a $C_2$-$C_{22}$ carboxylic acid and a $C_2$-$C_{22}$ percarboxylic acid and the peracid in the formed aqueous composition comprises peroxyformic acid only.

18. The method of claim 1, wherein the formic acid and hydrogen peroxide are contacted in the presence of a $C_2$-$C_{22}$ carboxylic acid and the peracid in the formed aqueous composition comprises peroxyformic acid and the $C_2$-$C_{22}$ percarboxylic acid.

19. The method of claim 1, which is conducted at a temperature ranging from about −2° C. to about 70° C.

20. The method of claim 1, wherein the mineral acid catalyst comprises sulfuric acid, nitric acid, phosphoric acid, pyrophosphoric acid, polyphosphoric acid, phosphonic acid or combinations thereof.

21. The method of claim 1, which is conducted in the presence of a cation acid exchange resin system.

22. The method of claim 1, wherein the resulting aqueous composition comprises a stabilizing agent, wherein the stabilizing agent is a phosphonate salt(s) and/or a heterocyclic dicarboxylic acid.

23. The method of claim 1, which further comprises a step of reducing the concentration of the hydrogen peroxide in the resulting aqueous composition.

24. The method of claim 23, wherein the concentration of the hydrogen peroxide in the resulting aqueous composition is reduced using a catalase or a peroxidase.

25. The method of claim 1, which is used to generate peroxyformic acid in situ for the application of the formed peroxyformic acid.

26. A peroxyformic acid composition formed by the method comprising:
contacting formic acid with hydrogen peroxide to form a resulting aqueous composition comprising a peracid that comprises peroxyformic acid, and from about 0.0001 wt-% to about 20 wt-% of a corrosion inhibitor;
wherein the contacting is conducted in the presence of a mineral acid catalyst, and
wherein before said contacting, the ratio between the concentration of said formic acid (w/v) and the concentration of said hydrogen peroxide (w/v) is about 4 or higher, and the ratio between the concentration of said peracid (w/w) and the concentration of hydrogen peroxide (w/w) in said formed resulting aqueous composition reaches about 4 or higher at least within 1 hour of said contacting.

27. The peroxyformic acid composition of claim 26, wherein the amount of corrosion inhibitor in the resulting aqueous composition is from about 0.0001 wt-% to about 10 wt-%.

28. The peroxyformic acid composition of claim 27, wherein the corrosion inhibitor comprises a phosphate ester, a derivative of the phosphate ester, trimeric C19 unsaturated fatty acid, a quat amine, a derivative of the quat amine, an imidazoline, a derivative of the imidazoline, an alkyl pyridine, a derivative of the alkyl pyridine, a phosphonium salt, a derivative of the phosphonium salt or combinations thereof.

29. The peroxyformic acid composition of claim 26, wherein before the contacting, the ratio between the concentration of the formic acid (w/v) and the concentration of the hydrogen peroxide (w/v) is from about 100 to about 4, and wherein the ratio between the concentration of the peracid (w/w) and the concentration of hydrogen peroxide (w/w) in the formed aqueous composition reaches from about 1500 to about 4 within about 1 hour of the contacting.

30. The peroxyformic acid composition of claim 26, wherein the resulting aqueous composition comprises from about 0.001% to about 20% peroxyformic acid, and about 5% (w/w) or less hydrogen peroxide.

31. The peroxyformic acid composition of claim 26, wherein the formic acid and the hydrogen peroxide are contacted in the absence of a $C_2$-$C_{22}$ carboxylic acid and a $C_2$-$C_{22}$ percarboxylic acid and the peracid in the formed aqueous composition comprises peroxyformic acid only.

32. The peroxyformic acid composition of claim 26, wherein the formic acid and hydrogen peroxide are contacted in the presence of a $C_2$-$C_{22}$ carboxylic acid and the peracid in the formed aqueous composition comprises peroxyformic acid and the $C_2$-$C_{22}$ percarboxylic acid.

33. The peroxyformic acid composition of claim 26, wherein the resulting aqueous composition comprises a stabilizing agent, wherein the stabilizing agent is a phosphonate salt(s) and/or a heterocyclic dicarboxylic acid.

34. A method for treating a target with a peroxyformic acid composition comprising:

contacting a target with an effective amount of peroxyformic acid composition to form a treated target composition, wherein said treated target composition comprises from about 0.1 ppm to about 5,000 ppm of said peroxyformic acid, and from about 0.0001 wt-% to about 20 wt-% of a corrosion inhibitor; and said contacting lasts for sufficient time to stabilize or reduce microbial population by at least a 2 log reduction in and/or on said target or said treated target composition.

35. The method of claim 34, wherein said peroxyformic acid composition is generated in situ by the method comprising contacting formic acid with hydrogen peroxide to form a resulting aqueous composition comprising a peracid that comprises peroxyformic acid, wherein the contacting is conducted in the presence of a mineral acid catalyst, and wherein before said contacting, the ratio between the concentration of said formic acid (w/v) and the concentration of said hydrogen peroxide (w/v) is about 4 or higher, and the ratio between the concentration of said peracid (w/w) and the concentration of hydrogen peroxide (w/w) in said formed resulting aqueous composition reaches about 4 or higher at least within 1 hour of said contacting.

\* \* \* \* \*